(12) United States Patent
Matubayasi et al.

(10) Patent No.: US 11,126,761 B2
(45) Date of Patent: Sep. 21, 2021

(54) FREE ENERGY CALCULATION DEVICE, METHOD, PROGRAM, AND RECORDING MEDIUM WITH THE PROGRAM RECORDED THEREON

(71) Applicants: Osaka University, Suita (JP); Toray Industries, Inc., Tokyo (JP)

(72) Inventors: Nobuyuki Matubayasi, Suita (JP); Tomohide Masuda, Kamakura (JP); Ryuji Tanimura, Kamakura (JP)

(73) Assignees: Osaka University, Suita (JP); Toray Industries, Inc., Tokyo (JP)

( * ) Notice: Subject to any disclaimer, the term of this patent is extended or adjusted under 35 U.S.C. 154(b) by 253 days.

(21) Appl. No.: 15/515,362

(22) PCT Filed: Sep. 30, 2015

(86) PCT No.: PCT/JP2015/077847
§ 371 (c)(1),
(2) Date: Mar. 29, 2017

(87) PCT Pub. No.: WO2016/052662
PCT Pub. Date: Apr. 7, 2016

(65) Prior Publication Data
US 2017/0220717 A1    Aug. 3, 2017

(30) Foreign Application Priority Data
Sep. 30, 2014   (JP) .............................. JP2014-202658

(51) Int. Cl.
*G06F 17/18* (2006.01)
*G06F 30/20* (2020.01)
(Continued)

(52) U.S. Cl.
CPC .............. *G06F 30/20* (2020.01); *G06F 17/18* (2013.01); *G16B 5/00* (2019.02); *G06F 2111/10* (2020.01)

(58) Field of Classification Search
CPC ....................................................... G06F 17/18
(Continued)

(56) References Cited

U.S. PATENT DOCUMENTS

2014/0222398 A1    8/2014 Yang et al.

FOREIGN PATENT DOCUMENTS

| EP | 2782033 A1 | 9/2014 |
|----|------------|--------|
| JP | 2001-501210 A | 1/2001 |

(Continued)

OTHER PUBLICATIONS

"High-Temperature Equation of State by a Perturbation Method. I. Nonpolar Gases," The Journal of Chemical Physics, vol. 22, No. 8 (1954), pp. 1420-1426.
(Continued)

*Primary Examiner* — Thai Q Phan
(74) *Attorney, Agent, or Firm* — DLA Piper LLP (US)

(57) ABSTRACT

A device, a method, a program, and a recording medium with the program recorded thereon to calculate a difference in free energy between different molecules at a high speed with a high accuracy. The device, the method, the program, and the recording medium with the program recorded thereon calculate ΔG based on the following numerical formula (1):

$$\Delta G = \int \phi P(\phi) d\phi + RT \int P(\phi) \log\left(\frac{P(\phi)}{P_0(\phi)}\right) d\phi + \int \Delta v(\phi) P(\phi) d\phi. \quad (1)$$

15 Claims, 4 Drawing Sheets

(51) Int. Cl.
 *G16B 5/00* (2019.01)
 *G06F 111/10* (2020.01)

(58) Field of Classification Search
 USPC .................................................. 703/2, 6, 8
 See application file for complete search history.

(56) References Cited

FOREIGN PATENT DOCUMENTS

| | | |
|---|---|---|
| JP | 2012-190423 A | 10/2012 |
| WO | 2013/142630 A1 | 9/2013 |

OTHER PUBLICATIONS

"Some Topics in the Theory of Fluids," The Journal of Chemical Physics, vol. 39, No. 11 (1963), pp. 2808-2812.

"Theory of solutions in the energetic representation. I. Formulation," The Journal of Chemical Physics, vol. 113, No. 15 (2000), pp. 6070-6081.

"Theory of solutions in the energy representation. II. Functional for the chemical potential," The Journal of Chemical Physics, vol. 117, No. 8 (2002), pp. 3605-3616.

"Theory of solutions in the energy representation. III. Treatment of the molecular flexibility," The Journal of Chemical Physics, vol. 119, No. 18 (2003), pp. 9686-9702.

Nobuyuki Matsubayashi, "Yoeki-nai no Nanoscale Kozotai no Jiyu Energy Kaiseki," The Electrochemical Society of Japan, Mar. 29, 2009, p. 65.

Extended European Search Report dated Jul. 5, 2018, of counterpart EP Application No. 15845958.6.

Tatsuhiko Miyata et al: "Free energy calculation using molecular dynamics simulation combined with the three dimensional reference interaction site model theory. I. Free energy perturbation and thermodynamic integration along a coupling parameter", *Journal of Chemical Physics*, vol. 133, No. 4, Jul. 28, 2010, p. 044114.

FREE ENERGY CALCULATION DEVICE, METHOD, PROGRAM, AND RECORDING MEDIUM WITH THE PROGRAM RECORDED THEREON

TECHNICAL FIELD

This disclosure relates to a device, a method, a program, and a recording medium with the program recorded thereon, for calculating a difference in free energy between different molecules at a high speed with a high accuracy.

BACKGROUND

Due to development of three-dimensional structure analysis technologies such as X-ray crystal structure analysis or nuclear magnetic resonance (NMR) and genetic engineering technology, three-dimensional structures of proteins as targets for drug discovery and development have been elucidated one after another. Along with this, developments of a molecular structure of a ligand to activate or inhibit a biological function of a protein has been performed actively based on the three-dimensional structures of the protein.

Particularly important technologies in development of a molecular structure of a ligand based on a three-dimensional structure of a protein include binding affinity prediction by calculating a difference in binding free energy between the protein and different ligands for the protein using computer simulation such as a molecular dynamics method or a Monte Carlo method. The binding free energy between a protein and a ligand is a physical quantity strictly correlated with a binding constant as an indicative of binding affinity between the protein and the ligand. A difference in binding free energy between different ligands for the same protein is a physical quantity strictly correlated with a ratio of binding constants between the different ligands and the protein. Therefore, a difference in binding affinity between different ligands for the same protein can be determined by a difference in binding free energy. That is, if it is possible to calculate a difference in binding free energy between different ligands for the same protein at a high speed with a high accuracy, prior to synthesis of a ligand and a binding strength experiment, by changing a functional group of the ligand and a backbone structure thereof, a molecular structure of the ligand can be designed such that binding free energy between a protein and a ligand is reduced, and acceleration and higher efficiency in drug discovery and development can be expected. In general, drug discovery and development require a free energy calculation method having a high speed at a level capable of calculating in practical calculation time of a few days or less, and having a high accuracy at a level capable of reproducing binding free energy or a difference in binding free energy obtained by a binding affinity experiment in an average error of ±1 kcal/mol or less.

Examples of a representative free energy calculation method include the free energy perturbation method (The Journal of Chemical Physics, 22(8), 1420-1426 (1954)), the particle insertion method (The Journal of Chemical Physics, 39(11), 2808-2812 (1963)), and the energy representation method (The Journal of Chemical Physics, 113(15), 6070-6081 (2000), The Journal of Chemical Physics, 117(8), 3605-3616 (2002) and The Journal of Chemical Physics, 119(18), 9686-9702 (2003)).

The free energy perturbation method is a calculation method of determining a difference in free energy between an initial state of a calculation target and a final state of a calculation target by gradually changing parameters for an intermolecular interaction between a ligand and a surrounding environment of the ligand such as water or a protein, introducing many virtual intermediate states connecting an initial state of a calculation target and a final state thereof, and determining and summing a difference in free energy between adjacent states. In general, the free energy perturbation method can reproduce a difference in binding free energy between different ligands for the same protein obtained by a binding affinity experiment with a high accuracy. However, the free energy perturbation method requires a long computing time, and is not a practical calculation method disadvantageously.

The particle insertion method is a method not requiring introduction of an intermediate state between an initial state containing no ligand but constituted by a solvent, a protein, or the like and a final state in which a ligand is bound to a protein to form a complex when binding free energy is calculated. The particle insertion method includes a step of generating many final states by repeating a sampling step of selecting position coordinates at random in an initial state and adding a ligand to the position coordinates. However, in general, a ligand interacts with a specific amino acid residue constituting a protein in a specific active site of a protein, and forms a complex in which the ligand and the protein are bound to each other. Therefore, the probability of generating a proper complex in which a ligand and a protein are bound to each other by addition of the ligand to randomly selected position coordinates is very low. Therefore, it is practically impossible to generate a large number of the complexes, and binding free energy cannot be calculated.

The energy representation method has a calculation accuracy almost equal to the free energy perturbation method, and is a method capable of calculating free energy at a high speed. However, when binding free energy is calculated, in a calculation process thereof, like the particle insertion method, the energy representation method includes a step of generating many final states constituted by a complex in which a ligand is bound to a protein and a solvent by repeating a sampling step of selecting position coordinates at random in an initial state containing no ligand but constituted by a solvent, a protein or the like and adding a ligand to the position coordinates. Therefore, binding free energy cannot be calculated.

In conventional free energy calculation methods, it is difficult to calculate binding free energy at a high speed with a high accuracy. In particular, the free energy perturbation method needs to introduce many intermediate states connecting an initial state and a final state, and has a long calculation time disadvantageously. In the particle insertion method or the energy representation method requiring to introduce no intermediate states, it is impossible to generate many complexes in which a ligand and a protein are bound to each other by adding the ligand to randomly selected position coordinates in an initial state containing no ligand but constituted by a solvent, a protein or the like, and binding free energy cannot be calculated disadvantageously. Therefore, it could be helpful is to provide a device, a method, a program, and a recording medium with the program recorded thereon, for calculating a difference in free energy between different molecules at a high speed with a high accuracy.

SUMMARY

We provide a calculation device including a control unit for calculating, with respect to change represented by reaction formula (1):

$$A+B \to AB \qquad (1)$$

wherein A represents an atomic assembly consisting of structure a or containing structure a, B represents a fragment consisting of one or more atoms, and AB represents an atomic assembly consisting of atomic assembly A and fragment B connected to structure a of the atomic assembly A, a difference $\Delta G$ between the sum of free energy of atomic assembly A before the change and free energy of fragment B, and free energy of atomic assembly AB after the change, in which the control unit includes:

a first atomic assembly model creation unit for creating a first atomic assembly model modeling atomic assembly A before the change;

a first coordinates acquisition unit for acquiring coordinates of atomic assembly A in each of first to i th states $F_1$ to $F_i$ (wherein i is an integer of two or more) by computer simulation with respect to the first atomic assembly model created by the first atomic assembly model creation unit;

a second coordinates acquisition unit for acquiring coordinates of atomic assembly AB generated by connection of fragment B to atomic assembly A in each of states $F_1$ to $F_i$ based on the coordinates of atomic assembly A acquired by the first coordinates acquisition unit;

a first interaction energy $\phi$ frequency distribution creation unit for calculating interaction energy $\phi$ between structure a and fragment B connected to the structure a based on the coordinates of atomic assembly AB acquired by the second coordinates acquisition unit, and creating a frequency distribution indicating a frequency in each class of interaction energy $\phi$;

a first interaction energy $\phi$ appearance probability calculation unit for calculating an appearance probability $P_0(\phi)$ in each class of interaction energy $\phi$ based on the frequency distribution created by the first interaction energy $\phi$ frequency distribution creation unit;

a first interaction energy $\varepsilon$ frequency distribution creation unit for calculating interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the second coordinates acquisition unit, and creating a frequency distribution indicating a frequency in each class of interaction energy $\varepsilon$ in each class of interaction energy $\phi$ in the frequency distribution created by the first interaction energy $\phi$ frequency distribution creation unit;

a first interaction energy $\varepsilon$ appearance probability calculation unit for calculating an appearance probability $P_0'(\varepsilon;\phi)$ in each class of interaction energy $\varepsilon$ in each class of interaction energy $\phi$ based on the frequency distribution created by the first interaction energy $\varepsilon$ frequency distribution creation unit;

a second atomic assembly model creation unit for creating a second atomic assembly model modeling atomic assembly AB after the change;

a third coordinates acquisition unit for acquiring coordinates of atomic assembly AB in each of first to j th states $G_1$ to $G_j$ (wherein j is an integer of two or more) by computer simulation with respect to the second atomic assembly model created by the second atomic assembly model creation unit;

a second interaction energy $\phi$ frequency distribution creation unit for calculating interaction energy $\phi$ between structure a and fragment B connected to the structure a based on the coordinates of atomic assembly AB acquired by the third coordinates acquisition unit, and creating a frequency distribution indicating a frequency in each class of interaction energy $\phi$;

a second interaction energy $\phi$ appearance probability calculation unit for calculating an appearance probability $P(\phi)$ in each class of interaction energy $\phi$ based on the frequency distribution created by the second interaction energy $\phi$ frequency distribution creation unit;

a second interaction energy $\varepsilon$ frequency distribution creation unit for calculating interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the third coordinates acquisition unit, and creating a frequency distribution indicating a frequency in each class of interaction energy $\varepsilon$;

a second interaction energy $\varepsilon$ appearance probability calculation unit for calculating an appearance probability $P'(\varepsilon)$ in each class of interaction energy $\varepsilon$ based on the frequency distribution created by the second interaction energy $\varepsilon$ frequency distribution creation unit;

a $\int \Delta v(\phi) P(\phi) d\phi$ calculation unit for calculating a free energy change amount $\int \Delta v(\phi) P(\phi) d\phi$, wherein $\Delta v(\phi)$ represents a free energy change amount caused by interaction energy $\varepsilon$ in each class of interaction energy $\phi$, caused by interaction energy $\varepsilon$ based on $P(\phi)$ calculated by the second interaction energy $\phi$ appearance probability calculation unit, $P_0'(\varepsilon;\phi)$ calculated by the first interaction energy $\varepsilon$ appearance probability calculation unit, and $P'(\varepsilon)$ calculated by the second interaction energy $\varepsilon$ appearance probability calculation unit; and a $\Delta G$ calculation unit for calculating $\Delta G$ based on $P_0(\phi)$ calculated by the first interaction energy $\phi$ appearance probability calculation unit, $P(\phi)$ calculated by the second interaction energy $\phi$ appearance probability calculation unit, $\int \Delta v(\phi) P(\phi) d\phi$ calculated by the $\int \Delta v(\phi) P(\phi) d\phi$ calculation unit, and numerical formula (1):

$$\Delta G = \int \phi P(\phi) d\phi + RT \int P(\phi) \log\left(\frac{P(\phi)}{P_0(\phi)}\right) d\phi + \int \Delta v(\phi) P(\phi) d\phi \qquad (1)$$

wherein R represents a gas constant, and T represents an absolute temperature at which the change represented by reaction formula (1) occurs.

In an aspect of the calculation device (hereinafter, referred to as "aspect 1A"), the second coordinates acquisition unit creates a third atomic assembly model modeling atomic assembly C consisting of structure a and fragment B connected to the structure a or containing structure a and fragment B connected to the structure a, acquires coordinates of atomic assembly C in each of first to k th states $H_1$ to $H_k$ (wherein k is an integer of two or more) by computer simulation with respect to the created third atomic assembly model, and selects a selected atomic group consisting of one or more atoms selected from atoms constituting structure a, rotates and/or translates coordinates of a selected atomic group of atomic assembly C in one or more states selected from states $H_1$ to $H_k$ with respect to coordinates of a selected atomic group of atomic assembly A in each of states $F_1$ to $F_i$, thereby creates coordinates of atomic assembly C having the minimum sum of squares of distances between corresponding atoms between the selected atomic group of atomic assembly A and the selected atomic group of atomic assembly C, superimposes atomic assembly C in one or more states selected from states $H_1$ to $H_k$ on atomic assembly A based on the created coordinates of atomic assembly C, and acquires one or more coordinates of atomic assembly AB generated by connection of fragment B to atomic assembly A based on coordinates of atomic assembly A and one or more coordinates of fragment B of atomic assembly C superimposed on atomic assembly A.

In an aspect of the calculation device (hereinafter, referred to as "aspect 2A"), the $\int \Delta v(\phi) P(\phi) d\phi$ calculation unit calculates a free energy change amount $\int \Delta v(\phi) P(\phi) d\phi$ caused by interaction energy $\varepsilon$ based on $P(\phi)$ calculated by the second interaction energy $\phi$ appearance probability calculation unit, $P_0'(\varepsilon;\phi)$ calculated by the first interaction energy $\varepsilon$ appearance probability calculation unit, and $P'(\varepsilon)$ calculated by the second interaction energy $\varepsilon$ appearance probability calculation unit by the energy representation method.

In an aspect of the calculation device (hereinafter, referred to as "aspect 3A"), fragment B is constituted by an atom(s) containing a point charge(s) as a virtual atom(s), and the second coordinates acquisition unit adds the point charge(s) of fragment B to a charge parameter(s) of an atom(s) constituting structure a of atomic assembly A.

Two or more of the aspects 1A to 3A can be combined.

In addition, we provide a calculation method of calculating, with respect to change represented by reaction formula (1):

$$A+B \to AB \quad (1)$$

wherein A represents an atomic assembly consisting of structure a or containing structure a, B represents a fragment consisting of one or more atoms, and AB represents an atomic assembly consisting of atomic assembly A and fragment B connected to structure a of the atomic assembly A, a difference $\Delta G$ between the sum of free energy of atomic assembly A before the change and free energy of fragment B, and free energy of atomic assembly AB after the change using a computer, in which a control unit of the computer performs:

a first atomic assembly model creation step for creating a first atomic assembly model modeling atomic assembly A before the change;

a first coordinates acquisition step for acquiring coordinates of atomic assembly A in each of first to i th states $F_1$ to $F_i$ (wherein i is an integer of two or more) by computer simulation with respect to the first atomic assembly model created by the first atomic assembly model creation step;

a second coordinates acquisition step for acquiring coordinates of atomic assembly AB generated by connection of fragment B to atomic assembly A in each of states $F_1$ to $F_i$ based on the coordinates of atomic assembly A acquired by the first coordinates acquisition step;

a first interaction energy $\phi$ frequency distribution creation step for calculating interaction energy $\phi$ between structure a and fragment B connected to the structure a based on the coordinates of atomic assembly AB acquired by the second coordinates acquisition step, and creating a frequency distribution indicating a frequency in each class of interaction energy $\phi$;

a first interaction energy $\phi$ appearance probability calculation step for calculating an appearance probability $P_0(\phi)$ in each class of interaction energy $\phi$ based on the frequency distribution created by the first interaction energy $\phi$ frequency distribution creation step;

a first interaction energy $\varepsilon$ frequency distribution creation step for calculating interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the second coordinates acquisition step, and creating a frequency distribution indicating a frequency in each class of interaction energy $\varepsilon$ in each class of interaction energy $\phi$ in the frequency distribution created by the first interaction energy $\phi$ frequency distribution creation step;

a first interaction energy $\varepsilon$ appearance probability calculation step for calculating an appearance probability $P_0'(\varepsilon;\phi)$ in each class of interaction energy $\varepsilon$ in each class of interaction energy $\phi$ based on the frequency distribution created by the first interaction energy $\varepsilon$ frequency distribution creation step;

a second atomic assembly model creation step for creating a second atomic assembly model modeling atomic assembly AB after the change;

a third coordinates acquisition step for acquiring coordinates of atomic assembly AB in each of first to j th states $G_1$ to $G_j$ (wherein j is an integer of two or more) by computer simulation with respect to the second atomic assembly model created by the second atomic assembly model creation step;

a second interaction energy $\phi$ frequency distribution creation step for calculating interaction energy $\phi$ between structure a and fragment B connected to the structure a based on the coordinates of atomic assembly AB acquired by the third coordinates acquisition step, and creating a frequency distribution indicating a frequency in each class of interaction energy $\phi$;

a second interaction energy $\phi$ appearance probability calculation step for calculating an appearance probability $P(\phi)$ in each class of interaction energy $\phi$ based on the frequency distribution created by the second interaction energy $\phi$ frequency distribution creation step;

a second interaction energy $\varepsilon$ frequency distribution creation step for calculating interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the third coordinates acquisition step, and creating a frequency distribution indicating a frequency in each class of interaction energy $\varepsilon$;

a second interaction energy $\varepsilon$ appearance probability calculation step for calculating an appearance probability $P'(\varepsilon)$ in each class of interaction energy $\varepsilon$ based on the frequency distribution created by the second interaction energy $\varepsilon$ frequency distribution creation step;

a $\int \Delta v(\phi) P(\phi) d\phi$ calculation step for calculating a free energy change amount $\int \Delta v(\phi) P(\phi) d\phi$, wherein $\Delta v(\phi)$ represents a free energy change amount caused by interaction energy $\varepsilon$ in each class of interaction energy $\phi$, caused by interaction energy $\varepsilon$ based on $P(\phi)$ calculated by the second interaction energy $\phi$ appearance probability calculation step, $P_0'(\varepsilon;\phi)$ calculated by the first interaction energy $\varepsilon$ appearance probability calculation step, and $P'(\varepsilon)$ calculated by the second interaction energy $\varepsilon$ appearance probability calculation step; and a $\Delta G$ calculation step for calculating $\Delta G$ based on $P_0(\phi)$ calculated by the first interaction energy $\phi$ appearance probability calculation step, $P(\phi)$ calculated by the second interaction energy $\phi$ appearance probability calculation step, ∫Δv(φ)P(φ)dφ calculated by the ∫Δv(φ)P(φ)dφ calculation step, and numerical formula (1):

$$\Delta G = \int \phi P(\phi)d\phi + RT \int P(\phi)\log\left(\frac{P(\phi)}{P_0(\phi)}\right)d\phi + \int \Delta v(\phi)P(\phi)d\phi \quad (1)$$

wherein R represents a gas constant, and T represents an absolute temperature at which the change represented by reaction formula (1) occurs.

In an aspect of the calculation method (hereinafter, referred to as "aspect 1B"), in the second coordinates acquisition step, the control unit of the computer creates a third atomic assembly model modeling atomic assembly C consisting of structure a and fragment B connected to the structure a or containing structure a and fragment B connected to the structure a, acquires coordinates of atomic assembly C in each of first to k th states $H_1$ to $H_k$ (wherein k is an integer of two or more) by computer simulation with respect to the created third atomic assembly model, and selects a selected atomic group consisting of one or more atoms selected from atoms constituting structure a, rotates and/or translates coordinates of a selected atomic group of atomic assembly C in one or more states selected from states $H_1$ to $H_k$ with respect to coordinates of a selected atomic group of atomic assembly A in each of states $F_1$ to $F_i$, thereby creates coordinates of atomic assembly C having the minimum sum of squares of distances between corresponding atoms between the selected atomic group of atomic assembly A and the selected atomic group of atomic assembly C, superimposes atomic assembly C in one or more states selected from states $H_1$ to $H_k$ on atomic assembly A based on the created coordinates of atomic assembly C, and acquires one or more coordinates of atomic assembly AB generated by connection of fragment B to atomic assembly A based on coordinates of atomic assembly A and one or more coordinates of fragment B of atomic assembly C superimposed on atomic assembly A.

In an aspect of the calculation method (hereinafter, referred to as "aspect 2B"), in the ∫Δv(φ)P(φ)dφ calculation step, the control unit of the computer calculates a free energy change amount ∫Δv(φ)P(φ)dφ caused by interaction energy ε based on P(φ) calculated by the second interaction energy φ appearance probability calculation step, $P_0'(\varepsilon;\phi)$ calculated by the first interaction energy ε appearance probability calculation step, and P'(ε) calculated by the second interaction energy ε appearance probability calculation step by the energy representation method.

In an aspect of the calculation method (hereinafter, referred to as "aspect 3B"), fragment B is constituted of an atom(s) containing a point charge(s) as a virtual atom(s), and in the second coordinates acquisition step, the control unit of the computer adds the point charge(s) of fragment B to a charge parameter(s) of an atom(s) constituting structure a of atomic assembly A.

Two or more of the aspects 1B to 3B can be combined.

In addition, we provide a program of calculating, with respect to change represented by reaction formula (1):

wherein A represents an atomic assembly consisting of structure a or containing structure a, B represents a fragment consisting of one or more atoms, and AB represents an atomic assembly consisting of atomic assembly A and fragment B connected to structure a of the atomic assembly A, a difference ΔG between the sum of free energy of atomic assembly A before the change and free energy of fragment B, and free energy of atomic assembly AB after the change, in which the program causes a control unit of a computer to function as:

a first atomic assembly model creation unit for creating a first atomic assembly model modeling atomic assembly A before the change;

a first coordinates acquisition unit for acquiring coordinates of atomic assembly A in each of first to i th states $F_1$ to $F_i$ (wherein i is an integer of two or more) by computer simulation with respect to the first atomic assembly model created by the first atomic assembly model creation unit;

a second coordinates acquisition unit for acquiring coordinates of atomic assembly AB generated by connection of fragment B to atomic assembly A in each of states $F_1$ to $F_i$ based on the coordinates of atomic assembly A acquired by the first coordinates acquisition unit;

a first interaction energy φ frequency distribution creation unit for calculating interaction energy φ between structure a and fragment B connected to the structure a based on the coordinates of atomic assembly AB acquired by the second coordinates acquisition unit, and creating a frequency distribution indicating a frequency in each class of interaction energy φ;

a first interaction energy φ appearance probability calculation unit for calculating an appearance probability $P_0(\phi)$ in each class of interaction energy φ based on the frequency distribution created by the first interaction energy φ frequency distribution creation unit;

a first interaction energy ε frequency distribution creation unit for calculating interaction energy ε between a part or the whole of an atomic assembly generated by removing structure aB consisting of structure a and fragment B connected to the structure a from atomic assembly AB, and fragment B based on the coordinates of atomic assembly AB acquired by the second coordinates acquisition unit, and creating a frequency distribution indicating a frequency in each class of interaction energy ε in each class of interaction energy φ in the frequency distribution created by the first interaction energy φ frequency distribution creation unit;

a first interaction energy ε appearance probability calculation unit for calculating an appearance probability $P_0'(\varepsilon;\phi)$ in each class of interaction energy ε in each class of interaction energy φ based on the frequency distribution created by the first interaction energy ε frequency distribution creation unit;

a second atomic assembly model creation unit for creating a second atomic assembly model modeling atomic assembly AB after the change;

a third coordinates acquisition unit for acquiring coordinates of atomic assembly AB in each of first to j th states $G_1$ to $G_j$ (wherein j is an integer of two or more) by computer simulation with respect to the second atomic assembly model created by the second atomic assembly model creation unit;

a second interaction energy φ frequency distribution creation unit for calculating interaction energy φ between structure a and fragment B connected to the structure a based on the coordinates of atomic assembly AB acquired by the third coordinates acquisition unit, and creating a frequency distribution indicating a frequency in each class of interaction energy φ;

a second interaction energy φ appearance probability calculation unit for calculating an appearance probability P(φ) in each class of interaction energy φ based on the frequency distribution created by the second interaction energy φ frequency distribution creation unit;

a second interaction energy ε frequency distribution creation unit for calculating interaction energy ε between a part or the whole of an atomic assembly generated by removing structure aB consisting of structure a and fragment B connected to the structure a from atomic assembly AB, and fragment B based on the coordinates of atomic assembly AB acquired by the third coordinates acquisition unit, and creating a frequency distribution indicating a frequency in each class of interaction energy ε;

a second interaction energy ε appearance probability calculation unit for calculating an appearance probability P'(ε) in each class of interaction energy ε based on the frequency distribution created by the second interaction energy ε frequency distribution creation unit;

a ∫Δv(φ)P(φ)dφ calculation unit for calculating a free energy change amount ∫Δv(φ)P(φ)dφ, wherein Δv(φ) represents a free energy change amount caused by interaction energy ε in each class of interaction energy φ, caused by interaction energy ε based on P(φ) calculated by the second interaction energy φ appearance probability calculation unit, $P_0'(ε;φ)$ calculated by the first interaction energy ε appearance probability calculation unit, and P'(ε) calculated by the second interaction energy ε appearance probability calculation unit; and a ΔG calculation unit for calculating ΔG based on $P_0(φ)$ calculated by the first interaction energy φ appearance probability calculation unit, P(φ) calculated by the second interaction energy φ appearance probability calculation unit, ∫Δv(φ)P(φ)dφ calculated by the ∫Δv(φ)P(φ)dφ calculation unit, and numerical formula (1):

$$\Delta G = \int \phi P(\phi)d\phi + RT \int P(\phi)\log\left(\frac{P(\phi)}{P_0(\phi)}\right)d\phi + \int \Delta v(\phi)P(\phi)d\phi \quad (1)$$

wherein R represents a gas constant, and T represents an absolute temperature at which the change represented by reaction formula (1) occurs.

In an aspect of the program (hereinafter, referred to as "aspect 1C"), the second coordinates acquisition unit creates a third atomic assembly model modeling atomic assembly C consisting of structure a and fragment B connected to the structure a or containing structure a and fragment B connected to the structure a, acquires coordinates of atomic assembly C in each of first to k th states $H_1$ to $H_k$ (wherein k is an integer of two or more) by computer simulation with respect to the created third atomic assembly model, and selects a selected atomic group consisting of one or more atoms selected from atoms constituting structure a, rotates and/or translates coordinates of a selected atomic group of atomic assembly C in one or more states selected from states $H_1$ to $H_k$ with respect to coordinates of a selected atomic group of atomic assembly A in each of states $F_1$ to $F_j$, thereby creates coordinates of atomic assembly C having the minimum sum of squares of distances between corresponding atoms between the selected atomic group of atomic assembly A and the selected atomic group of atomic assembly C, superimposes atomic assembly C in one or more states selected from states $H_1$ to $H_k$ on atomic assembly A based on the created coordinates of atomic assembly C, and acquires one or more coordinates of atomic assembly AB generated by connection of fragment B to atomic assembly A based on coordinates of atomic assembly A and one or more coordinates of fragment B of atomic assembly C superimposed on atomic assembly A.

In an aspect of the program (hereinafter, referred to as "aspect 2C"), the ∫Δv(φ)P(φ)dφ calculation unit calculates a free energy change amount ∫Δv(φ)P(φ)dφ caused by interaction energy ε based on P(φ) calculated by the second interaction energy φ appearance probability calculation unit, $P_0'(ε;φ)$ calculated by the first interaction energy ε appearance probability calculation unit, and P'(ε) calculated by the second interaction energy ε appearance probability calculation unit by the energy representation method.

In an aspect of the program (hereinafter, referred to as "aspect 3C"), fragment B is constituted by an atom(s) containing a point charge(s) as a virtual atom(s), and the second coordinates acquisition unit adds the point charge(s) of fragment B to a charge parameter(s) of an atom(s) constituting structure a of atomic assembly A.

Two or more of the aspects 1C to 3C can be combined.

Furthermore, we provide a computer-readable recording medium with the program recorded thereon.

By acquiring coordinates of atomic assembly AB generated by connection of fragment B to atomic assembly A based on coordinates of atomic assembly A, coordinates of atomic assembly AB can be acquired efficiently. This can improve a sampling efficiency from an ensemble generated by computer simulation significantly as compared with the particle insertion method or the energy representation method. In addition, improvement of the sampling efficiency makes it possible to calculate numerical formula (1) satisfying a classical statistical mechanics theory with a statistically correct accuracy, and makes it possible to secure a high calculation accuracy. Furthermore, an intermediate state connecting an initial state and a final state is not required. Therefore, calculation time can be reduced largely as compared with the free energy perturbation method. Therefore, a difference in binding free energy between different molecules can be calculated at a high speed with a high accuracy, and acceleration and higher efficiency in novel drug discovery and development are possible.

Figure 1:
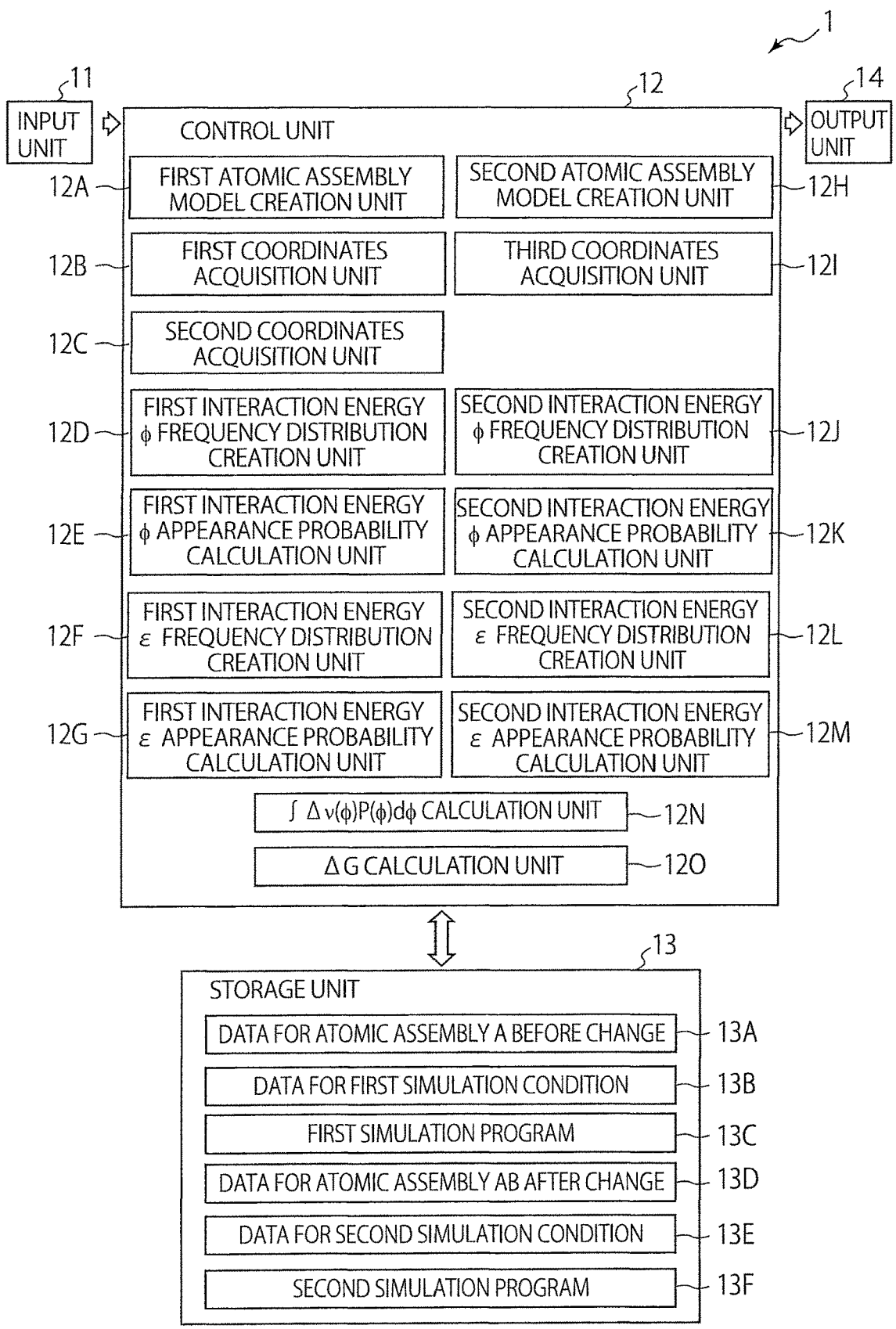
FIG. 1 is a functional block diagram illustrating a configuration of a calculation device according to an example.

REFERENCE SIGNS LIST 1 calculation device
11 input unit
12 control unit
12A first atomic assembly model creation unit
12B first coordinates acquisition unit
12C second coordinates acquisition unit 12D first interaction energy ϕ frequency distribution creation unit
12E first interaction energy ϕ appearance probability calculation unit
12F first interaction energy ε frequency distribution creation unit
12G first interaction energy ε appearance probability calculation unit
12H second atomic assembly model creation unit
12I third coordinates acquisition unit
12J second interaction energy ϕ frequency distribution creation unit
12K second interaction energy ϕ appearance probability calculation unit
12L second interaction energy ε frequency distribution creation unit
12M second interaction energy ε appearance probability calculation unit
12N ∫Δν(ϕ)P(ϕ)dϕ calculation unit
12O ΔG calculation unit
13 storage unit
13A data for atomic assembly A before the change
13B data for first simulation condition
13C first simulation program
13D data for atomic assembly AB after the change
13E data for second simulation condition
13F second simulation program
14 output unit

DETAILED DESCRIPTION

In general, in the classical statistical mechanics theory, regarding change represented by reaction formula (1), a difference between the sum of free energy of an atomic assembly A before the change and free energy of a fragment B, and free energy of an atomic assembly AB after the change is represented by numerical formula (2).

Here, atomic assembly A before the change and fragment B are in a thermal equilibrium state, and atomic assembly AB after the change is also in a thermal equilibrium state. In the following numerical formulae (2) to (5), an integral sign (∫) represents an integral sign for each integration variable collectively.

Meanwhile, P(ϕ) that is an appearance probability (that is, an energy distribution) of interaction energy ϕ between structure a in atomic assembly AB after the change and fragment B connected to the structure a is represented by numerical formula (3). $P_0(\phi)$ that is an appearance probability (that is, an energy distribution) of interaction energy ϕ between structure a in atomic assembly AB generated by connection of fragment B to atomic assembly A before the change and fragment B connected to the structure a is represented by numerical formula (4). A ratio therebetween can be represented by numerical formula (5). Numerical formula (1) can be introduced by modifying numerical formula (5). Here, in numerical formulae (3) and (4), $$\delta(\phi - (\Xi(\psi, K) - \Psi(\psi) - W(K)))$$

is a delta function of Dirac, and is a function to obtain 1 when ϕ is equal to $$\Xi(\psi, K) - \Psi(\psi) - W(K)$$

and to obtain zero when ϕ is not equal thereto.

$$\Delta G = -RT \log \left( \frac{\int \exp\left(-\frac{\Xi(\psi, K) + \sum_i v(\psi, K, x_i) + U(X)}{RT}\right) d\psi dK dX}{\int \exp\left(-\frac{\Psi(\psi) + W(K) + \sum_i u(K, x_i) + U(X)}{RT}\right) d\psi dK dX} \right) \quad (2)$$

$$P(\phi) = \frac{\int \delta(\phi - (\Xi(\psi, K) - \Psi(\psi) - W(K))) \exp\left(-\frac{\Xi(\psi, K) + \sum_i v(\psi, K, x_i) + U(X)}{RT}\right) d\psi dK dX}{\int \exp\left(-\frac{\Xi(\psi, K) + \sum_i v(\psi, K, x_i) + U(X)}{RT}\right) d\psi dK dX} \quad (3)$$

$$P_0(\phi) = \frac{\int \delta(\phi - (\Xi(\psi, K) - \Psi(\psi) - W(K))) \exp\left(-\frac{\Psi(\psi) + W(K) + \sum_i u(K, x_i) + U(X)}{RT}\right) d\psi dK dX}{\int \exp\left(-\frac{\Psi(\psi) + W(K) + \sum_i u(K, x_i) + U(X)}{RT}\right) d\psi dK dX} \quad (4)$$

ψ: set of coordinates of atoms constituting fragment B
K: set of coordinates of atoms constituting structure a
X: set of coordinates of all the atoms constituting atomic assembly generated by removing structure aB consisting of structure a and fragment B connected to the structure a from atomic assembly AB after change (that is, environment around structure aB in atomic assembly AB after change) or set of coordinates of all the atoms constituting atomic assembly generated by removing structure a from atomic assembly A before change (that is, environment around structure a in atomic assembly A before change)
$x_i$: set of coordinates of i th molecule constituting atomic assembly (for example, set of coordinates of atoms constituting i th water molecule in a case where atomic assembly AB contains a plurality of water molecules and the number is given to each of the water molecules) in atomic assembly generated by removing structure aB consisting of structure a and fragment B connected to the structure a from atomic assembly AB after change (that is, environment around structure aB in atomic assembly AB after change) or atomic assembly generated by removing structure a from atomic assembly A before change (that is, environment around structure a in atomic assembly A before change)
Ξ: interaction energy between atoms constituting structure aB consisting of structure a and fragment B connected to the structure a
Ψ: interaction energy between atoms constituting fragment B
W: interaction energy between atoms constituting structure a
U: interaction energy between atoms constituting atomic assembly generated by removing structure aB consisting of structure a and fragment B connected to the structure a from atomic assembly AB after change (that is, environment around structure aB in atomic assembly AB after change) or between atoms constituting atomic assembly generated by removing structure a from atomic assembly A before change (that is, environment around structure a in atomic assembly A before change)

v: interaction energy between structure aB consisting of structure a and fragment B connected to the structure a and environment around the structure aB (that is, atomic assembly generated by removing the structure aB from atomic assembly AB) in atomic assembly AB after change u: interaction energy between structure a and environment around the structure a (that is, atomic assembly generated by removing the structure a from atomic assembly A before change) in atomic assembly A before change R: gas constant T: absolute temperature at which change represented by reaction formula (1) occurs "Interaction energy" in $\Xi$, $\Psi$, W, U, v, and u means energy caused by interaction for interatomic bond involving a bond length, a bond angle, a twist angle, or the like, and energy caused by non-bonding interaction such as van der Waals interaction or electrostatic interaction or the like.

$$\frac{P(\phi)}{P_0(\phi)} = = \exp\left(\frac{\Delta G}{RT}\right)\exp\left(-\frac{\phi}{RT}\right) \quad (5)$$

$$\frac{\int \delta(\phi - (\Xi(\psi, K) - \Psi(\psi) - W(K)))\exp\left(-\frac{\Psi(\psi) + W(K) + \sum_i v(\psi, K, x_i) + U(X)}{RT}\right)d\psi dKdX}{\int \delta(\phi - (\Xi(\psi, K) - \Psi(\psi) - W(K)))\exp\left(-\frac{\Psi(\psi) + W(K) + \sum_i v(\psi, K, x_i) + U(X)}{RT}\right)d\psi dKdX} =$$

$$\exp\left(\frac{\Delta G}{RT}\right)\exp\left(-\frac{\phi}{RT}\right)\exp\left(-\frac{\Delta v(\phi)}{RT}\right)$$

The first term of numerical formula (1) represents an average value of interaction energy $\phi$ between structure a in atomic assembly AB after the change and fragment B connected to the structure a.

The first and second terms in numerical formula (1) represent a free energy change amount caused by generation of connection between fragment B and structure a of atomic assembly A in the change represented by reaction formula (1).

$\Delta v(\phi)$ in the third term in numerical formula (1) represents a free energy change amount in the change represented by reaction formula (1) when the interaction energy between structure a and fragment B connected to the structure a is $\phi$, and represents a free energy change amount caused by an interaction between fragment B and a part or the whole of an atomic assembly generated by removing structure aB consisting of structure a and fragment B connected to the structure a from atomic assembly AB.

In the second term in numerical formula (1), as for $P(\phi)$ which is an appearance probability of interaction energy $\phi$ between structure a in atomic assembly AB after the change and fragment B connected to the structure a, and $P_0(\phi)$ which is an appearance probability of interaction energy $\phi$ between structure a in atomic assembly AB generated by connection of fragment B to atomic assembly A before the change and fragment B connected to the structure a, it is necessary that $P(\phi)/P_0(\phi)$ as a ratio between $P(\phi)$ and $P_0(\phi)$ does not diverge. That is, when $\phi$ has an appearance probability within a range of $0<P(\phi)\leq 1$, $P_0(\phi)$ also needs to have an appearance probability within a range of $0<P_0(\phi)\leq 1$.

The third term $\int \Delta v(\phi)P(\phi)d\phi$ in numerical formula (1) represents a free energy change amount caused by interaction energy $\varepsilon$ in the change represented by reaction formula (1), and can be calculated by applying a conventional energy representation method using numerical formula (6) below. Notation on the left side in numerical formula (6) represents a distribution function like notation in the conventional energy representation method. Here, when fragment B contains a virtual atom(s) such as a point charge(s) described below, for example, when atomic assembly AB is anisole ($C_6H_5OCH_3$) and fragment B is formed of a methoxy group ($-OCH_3$) and a point charge (virtual atom having a charge parameter contained in the benzene ring carbon atom to which the methoxy group is connected), removing fragment B from atomic assembly AB means removing the methoxy group and a charge parameter contained in the point charge from the anisole. That is, atomic assembly A is an atomic assembly represented by $C_6H_5$, and an atomic assembly in which the charge parameter contained in a benzene ring carbon atom to which the methoxy group is connected in atomic assembly AB is zero. For example, when fragment B is formed of a methoxy group ($-OCH_3$) and a point charge (virtual atom having a charge parameter contained in the benzene ring carbon atom to which the methoxy group is connected), and atomic assembly A is an atomic assembly in which a partial charge contained in the benzene ring carbon atom to which the methoxy group in fragment B is connected is zero, represented by $C_6H_5$, connection of fragment B to atomic assembly A means forming a covalent bond between an oxygen atom of the methoxy group in fragment B and the benzene ring carbon atom, and adding a partial charge (charge parameter) contained in the point charge of fragment B to the charge parameter of a benzene ring carbon atom to which the oxygen atom of the methoxy group is connected. A charge parameter contained in an atom may be referred to as a partial charge. In addition, for example, removing a charge parameter(s) contained in a point charge(s) of fragment B from a charge parameter(s) of an atom(s) constituting atomic assembly AB may be referred to as removing the point charge(s) of fragment B from atomic assembly AB. Similarly, adding a charge parameter(s) contained in a point charge(s) of fragment B to a charge parameter(s) of an atom(s) constituting atomic assembly AB may be referred to as adding the point charge(s) of fragment B to atomic assembly AB or adding the point charge(s) of fragment B to the charge parameter(s) of an atom(s) constituting atomic assembly AB.

$\int \Delta v(\phi)P(\phi)d\phi$ in the third term in numerical formula (1) can be calculated without calculating $\Delta v(\phi)$ based on $P(\phi)$ which is an appearance probability in each class of interaction energy $\phi$ in atomic assembly AB after the change, $P_0'(\varepsilon;\phi)$ which is an appearance probability in each class of interaction energy $\varepsilon$ in each class of interaction energy $\phi$ in atomic assembly AB generated by connection of fragment B to atomic assembly A before the change, and $P'(\varepsilon)$ which is an appearance probability in each class of interaction energy $\varepsilon$ in atomic assembly AB after the change. In addition, for example, $\int \Delta v(\phi)P(\phi)d\phi$ can be calculated by calculating a free energy change amount $\Delta v(\phi)$ caused by interaction energy $\varepsilon$ in each class of interaction energy $\phi$, and using the calculated $\Delta v(\phi)$ and $P(\phi)$ that is an appearance probability in each class of interaction energy $\phi$ in atomic assembly AB after the change.

$$\hat{\rho}(\varepsilon) = \sum_i \delta(\varepsilon - (v(\psi, K, x_i) - u(K, x_i))) \quad (6)$$

As described in detail below, a sampling efficiency can be improved significantly by adding an atom(s) constituting fragment B to an atom(s) constituting atomic assembly A. Therefore, a method of calculating $\Delta v(\phi)$ is not particularly limited, but, for example, the conventional particle insertion method or energy representation method can be used. Note that a difference $\Delta G$ in free energy in numerical formula (1) can be applied to calculation of any difference in free energy such as a difference in solvation free energy or a difference in binding free energy.

$\Delta G$ is a free energy change amount in change represented by reaction formula (1):

$$A+B \rightarrow AB \quad (1)$$

wherein A represents an atomic assembly consisting of structure a or containing structure a, B represents a fragment consisting of one or more atoms, and AB represents an atomic assembly consisting of atomic assembly A and fragment B connected to structure a of the atomic assembly A, that is, a difference $(G_2-G_1)$ between the sum $G_1$ of free energy of atomic assembly A before the change and free energy of fragment B, and free energy $G_2$ of atomic assembly AB after the change. Atomic assembly A does not interact with fragment B before the change.

Each of atomic assembly A and atomic assembly AB is atomic assembly constituted by one or more atoms. Each of atomic assembly A and atomic assembly AB may contain one or more atoms not connected to another atom. The atom(s) includes an ion(s). In addition, the atom(s) includes a virtual atom(s) (nonexistent atom(s)). Examples of an interatomic connection constituting each of atomic assembly A and atomic assembly AB include a covalent bond, a coordination bond, a hydrogen bond, an electrostatic interaction, and a hydrophobic interaction. Each of atomic assembly A and atomic assembly AB may be constituted by one kind of interatomic connection (for example, a covalent bond) or a combination of two or more kinds of interatomic connections (for example, a combination of a covalent bond and one or more kinds of other interatomic connections).

Each of atomic assembly A and atomic assembly AB may be constituted by one or more kinds of molecules.

Examples of the molecule include a ligand(s), a protein(s) to which the ligand(s) is bound, and a solvent molecule(s) such as a water molecule(s). When atomic assembly A is constituted by one kind of molecule, atomic assembly AB is also constituted by one kind of molecule. When atomic assembly A is constituted of two or more kinds of molecules, atomic assembly AB is also constituted by two or more kinds of molecules. Examples of when each of atomic assembly A and atomic assembly AB is constituted by two or more kinds of molecules include when each of atomic assembly A and atomic assembly AB contains a ligand(s), and further contains a protein(s) to which the ligand(s) is bound and/or a solvent molecule(s) such as a water molecule(s). When each of atomic assembly A and atomic assembly AB contains a ligand(s), and further contains a protein(s) to which the ligand(s) is bound, the ligand(s) and the protein(s) may form a complex. Examples of a bond type(s) between a ligand and a protein in the complex include a coordination bond, a hydrogen bond, an electrostatic interaction, a covalent bond, and a hydrophobic interaction. When each of atomic assembly A and atomic assembly AB contains a ligand(s) or a complex(es) formed of a ligand(s) and a protein(s), examples of a bond type(s) between the ligand(s) or the complex(es) and a solvent molecule(s) such as a water molecule(s) include a coordination bond, a hydrogen bond, an electrostatic interaction, a covalent bond, and a hydrophobic interaction.

Atomic assembly A is formed of structure a or contains structure a. When atomic assembly A is constituted of one molecule, structure a may be the whole of the structure of the molecule (in this case, atomic assembly A is formed of structure a), or may be a part of the structure of the molecule (in this case, atomic assembly A contains structure a). When atomic assembly A is constituted of two or more molecules, structure a may be the whole of the structure of the two or more molecules (in this case, atomic assembly A is formed of structure a), or may be a part of the structure of the two or more molecules (in this case, atomic assembly A contains structure a). When atomic assembly A contains a complex (es) formed of a protein(s) and a ligand(s), examples of a part of the structure of the complex(es) include the whole or a part of the structure of the ligand(s), the whole or a part of the structure of the protein(s), a portion formed of the whole or a part of the ligand(s) and a part of the protein(s), and a portion formed of the whole or a part of a receptor(s) and a part of the ligand(s).

Atomic assembly A corresponds to an atomic assembly obtained by removing fragment B from atomic assembly AB. For example, when atomic assembly AB is anisole ($C_6H_5OCH_3$) and fragment B is a methoxy group ($—OCH_3$), atomic assembly A is $C_6H_5$. In addition, for example, when atomic assembly AB is anisole ($C_6H_5OCH_3$) and fragment B is formed of a methoxy group ($—OCH_3$) and a point charge (virtual atom having a charge parameter contained in a benzene ring carbon atom to which the methoxy group is connected), atomic assembly A is obtained by removing the methoxy group and the point charge from the anisole. That is, atomic assembly A is an atomic assembly represented by $C_6H_5$, and an atomic assembly in which the charge parameter contained in the benzene ring carbon atom to which the methoxy group was connected in atomic assembly AB is zero.

Atomic assembly AB is formed of atomic assembly A and fragment B connected to structure a of the atomic assembly A. Atomic assembly AB corresponds to an atomic assembly in which fragment B is connected to atomic assembly A. For example, when atomic assembly A has a structure obtained by removing a methoxy group and a point charge (partial charge contained in the benzene ring carbon atom to which the methoxy group is connected) from anisole, and fragment B is formed of a methoxy group and the point charge, atomic assembly AB is anisole.

The number of atoms constituting structure a is not particularly limited as long as being one or more, but is preferably three or more, and more preferably five or more. When the number of atoms constituting structure a is three or more, connection of fragment B to structure a of atomic assembly A can be performed efficiently. Therefore, a sampling efficiency can be improved. In addition, an upper limit value of the number of atoms constituting structure a is not particularly limited.

The kind of an atom constituting structure a is not particularly limited. Examples of an atom constituting structure a include a carbon atom, a hydrogen atom, a nitrogen atom, and an oxygen atom. Structure a may be constituted of one kind of atom or two or more kinds of atoms.

A bond type(s) between atoms constituting structure a is not particularly limited. Examples of the bond type(s) between atoms constituting structure a include a covalent bond, a coordination bond, a hydrogen bond, an electrostatic interaction, and a hydrophobic interaction. Structure a may be constituted of one kind of interatomic connection (for example, a covalent bond) or a combination of two or more kinds of connections (for example, a combination of a covalent bond and one or more kinds of other connections).

An atom constituting structure a may contain one or more virtual atoms (nonexistent atoms). Structure a may be constituted only by an existent atom(s), only by a virtual atom(s), or by a combination of an existent atom(s) and a virtual atom(s). Examples of the virtual atom include an atom in which a valence shell does not contain eight electrons formally. It is known that an atom corresponding to a typical element belonging to groups 1, 2, and 13 to 18 in the periodic table usually satisfies the octet rule by taking an electron arrangement formally having eight electrons in a valence shell thereof and exists in a chemically stable state. Examples of another virtual atom include a point charge not having an interaction for a bond involving a bond length, a bond angle, a twist angle or the like or a van der Waals interaction with another atom(s) (that is, having a van der Waals potential of zero) but having an electrostatic interaction(s) with another atom(s) (that is, having a charge parameter and a Coulomb potential), an atom having no electrostatic interactions with another atom(s) (that is, having a Coulomb potential of zero) but having an interaction(s) for a bond caused by a bond length, a bond angle, a twist angle or the like and a van der Waals interaction with another atom(s), an atom existing in an ionic state, and a dummy atom not having any of an interaction(s) for a bond caused by a bond length, a bond angle, a twist angle or the like, a van der Waals interaction, and an electrostatic interaction with another atom(s). Energy caused by a van der Waals interaction is referred to as a van der Waals potential, and energy caused by an electrostatic interaction is referred to as a Coulomb potential.

The number of atoms constituting fragment B is not particularly limited as long as being one or more. An upper limit value of the number of atoms constituting fragment B is not particularly limited, but is usually 25, and preferably 10.

The kind of an atom(s) constituting fragment B is not particularly limited. Examples of an atom(s) constituting fragment B include a carbon atom, a hydrogen atom, a nitrogen atom, and an oxygen atom. Fragment B may be constituted of one kind of atom or two or more kinds of atoms.

A bond type(s) between atoms constituting fragment B is not particularly limited. Examples of the bond type(s) between atoms constituting fragment B include a covalent bond, a coordination bond, a hydrogen bond, an electrostatic interaction, and a hydrophobic interaction. Fragment B may be constituted of one kind of interatomic bond (for example, a covalent bond) or a combination of two or more kinds of bonds (for example, a combination of a covalent bond and one or more kinds of other bonds).

An atom constituting fragment B may contain one or more virtual atoms (nonexistent atoms). Fragment B may be constituted only of an existent atom(s), only a virtual atom(s), or a combination of an existent atom(s) and a virtual atom(s). Examples of the virtual atom(s) include similar specific examples to structure a. When fragment B contains a point charge(s) as a virtual atom(s) and is constituted a combination of an existent atom(s) and a virtual atom(s), there is no covalent bond(s) between the existent atom(s) and the virtual atom(s), and there are no interactions for the bond caused by the bond length, the bond angle, the twist angle, or the like between the existent atom(s) and the virtual atom(s). In computer simulation, an electrostatic interaction between a virtual atom(s) (point charge) and an existent atom(s) in fragment B is preferably calculated. However, it does not matter whether the electrostatic interaction is calculated or not as long as being unified in a process of calculating free energy. When it is assumed that there is a covalent bond(s) between a virtual atom(s) (point charge(s)) and an existent atom(s) in fragment B and there are three or more covalent bonds between the atoms, it is preferable to calculate an electrostatic interaction(s) between the virtual atom(s) (point charge(s)) and the existent atom(s) considering a so-called "1-4 interaction" in computer simulation such as molecular dynamics simulation. For example, when structure aB is anisole ($C_6H_5OCH_3$) and fragment B is formed of a methoxy group ($-OCH_3$) and a point charge (virtual atom having a charge parameter contained in the benzene ring carbon atom to which the methoxy group is connected), it is preferable to calculate the electrostatic interaction between the point charge and each of the hydrogen atoms of the methoxy group.

A calculation device according to an example is described based on the drawings.

As illustrated in FIG. 1, a calculation device 1 includes an input unit 11, a control unit 12, a storage unit 13, and an output unit 14 connected to one another through a system bus. The calculation device 1 can be implemented by using a general-purpose computer as basic hardware.

For example, the input unit 11 is constituted of a pointing device such as a keyboard or a mouse operated by an operator, and inputs various operation signals such as an instruction by an operator (for example, an instruction to execute a program or an instruction to display a result of processing) or input of data required for processing. The control unit 12 causes the storage unit 13 to store the input data.

For example, the control unit 12 is constituted of CPU, RAM, ROM or the like, and calculates ΔG based on various data stored in the storage unit 13, various programs or the like. At this time, by executing a calculation program for calculating ΔG, the control unit 12 functions as a first atomic assembly model creation unit 12A, a first coordinates acquisition unit 12B, a second coordinates acquisition unit 12C, a first interaction energy ϕ frequency distribution creation unit 12D, a first interaction energy ϕ appearance probability calculation unit 12E, a first interaction energy ε frequency distribution creation unit 12F, a first interaction energy appearance probability calculation unit 12G, a second atomic assembly model creation unit 12H, a third coordinates acquisition unit 12I, a second interaction energy ϕ frequency distribution creation unit 12J, a second interaction energy ϕ appearance probability calculation unit 12K, a second interaction energy ε frequency distribution creation unit 12L, a second interaction energy ε appearance probability calculation unit 12M, a ∫Δv(ϕ)P(ϕ)dϕ calculation unit 12N, and a ΔG calculation unit 12O. Note that CPU of the control unit 12 may include a plurality of arithmetic cores, and each of the arithmetic cores may function as various unit by execution of a calculation program to calculate ΔG. According to such a configuration, a plurality of calculations can be processed in parallel, and time required to calculate ΔG can be thereby reduced.

For example, the storage unit 13 is constituted of a storage such as RAM or a hard disc, and stores various data, various programs and the like. Examples of the data and program stored in the storage unit 13 include data 13A for atomic assembly A before the change, data 13B for a first simulation condition, a first simulation program 13C, data 13D for atomic assembly AB after the change, data 13E for a second simulation condition, and a second simulation program 13F. In this example, the first simulation program 13C and the second simulation program 13F are described as separate programs, but the first simulation program 13C and the second simulation program 13F may be one program.

For example, the output unit 14 is constituted of a display or the like, and outputs a result acquired or calculated by various units (for example, ΔG calculated by the ΔG calculation unit 12O).

The first atomic assembly model creation unit 12A creates a first atomic assembly model modeling atomic assembly A before the change. The control unit 12 causes the storage unit 13 to store data for the first atomic assembly model created by the first atomic assembly model creation unit 12A (for example, coordinates of each of atoms constituting atomic assembly A, the kind thereof, a mass thereof, a partial charge thereof, and interatomic bond information).

When creating the first atomic assembly model, the first atomic assembly model creation unit 12A uses the data 13A for atomic assembly A before the change that is stored in the storage unit 13. For example, the data 13A for atomic assembly A before the change is stored in the storage unit 13 in a form of a file which can read by the control unit 12. The data 13A for atomic assembly A before the change is not particularly limited as long as the first atomic assembly model modeling atomic assembly A before the change can be created. Examples of the data 13A for atomic assembly A before the change include coordinates of each of atoms constituting atomic assembly A, the kind thereof, a mass thereof, a partial charge thereof, and interatomic bond information.

The first atomic assembly model is not particularly limited as long as computer simulation is possible. Examples of the atomic assembly model include an all-atom model, a beads spring model, and a united atom model. Note that the beads spring model is a model in which a monomer unit constituting atomic assembly A is assumed to be one bead (segment) and the beads are connected with a virtual spring(s), and that the united atom model is a model in which a hydrogen atom is included in a heavy atom (for example, a carbon atom) and is handled as one atom (mass point).

The first coordinates acquisition unit 12B acquires coordinates of atomic assembly A in each of first to i th states $F_1$ to $F_i$ (wherein i is an integer of two or more) by a snapshot output as a result of computer simulation with respect to the first atomic assembly model created by the first atomic assembly model creation unit 12A. The snapshot includes coordinates of all the atoms constituting atomic assembly A. That is, the snapshot in each of states $F_1$ to $F_i$ includes coordinates of all the atoms constituting atomic assembly A in each of states $F_1$ to $F_i$. Hereinafter, coordinates of atomic assembly A in states $F_1, F_2, \ldots,$ and $F_i$ may be referred to as coordinates $R_A(F_1), R_A(F_2), \ldots,$ and $R_A(F_i)$, respectively. The control unit 12 causes the storage unit 13 to store coordinates of all the atoms constituting atomic assembly A, acquired by the first coordinates acquisition unit 12B.

Computer simulation performed by the first coordinates acquisition unit 12B is not particularly limited as long as being based on a statistical mechanics theory. Examples of representative computer simulation include a molecular dynamics method, a Monte Carlo method, and a method obtained by combining the molecular dynamics method or the Monte Carlo method and a first-principle calculation.

The first coordinates acquisition unit 12B performs computer simulation based on the data for the first atomic assembly model, the data 13B for the first simulation condition, the first simulation program 13C and the like that are stored in the storage unit 13. The data 13B for the first simulation condition is stored in the storage unit 13 in a form of a file that can read by the control unit 12.

The simulation condition is not particularly limited as long as computer simulation can be performed. Examples of the simulation condition include a temperature condition, a pressure condition, the kind of a potential parameter(s) and a value(s) thereof, the kind of an ensemble to be generated, a boundary condition, and an output condition such as the number of snapshots.

Examples of the potential parameter(s) include a parameter(s) for an interatomic bond(s) involving a bond length, a bond angle, a twist angle or the like, a van der Waals interaction that acts between atoms, and an electrostatic interaction.

Examples of the potential parameters include the known potential parameters such as Amber, GAFF, CHARMm (registered trademark), CGenFF (CHARMm36), DISCOVER, GROMOS, DREIDING, or OPLS.

For example, when Amber is used as the potential parameter, a parameter value(s) for a bond length, a bond angle, van der Waals or the like is determined based on an atom type assigned to each of the atoms constituting atomic assembly A and a combination of the atom types of the atoms.

The potential parameters can be grouped into potential parameters for atomic bonds and non-bonding potential parameters not involved in presence or absence of a bond. When calculation accuracy is considered, it is preferable to determine the potential parameters by a method described below.

It is preferable to determine the potential parameters for an atomic bond by quantum chemical calculation based on first principle calculation. As the quantum chemical calculation, it is preferable to use a Hartree Fock method (hereinafter, referred to as "HF method"), and it is more preferable to use a density functional theory using B3LYP as a functional (hereinafter referred to as a "B3LYP method"). When the HF method or the B3LYP method is used, it is necessary to specify a basis function to develop one electron orbital. When calculation time and calculation accuracy are considered, 6-31G(d) basis function, 6-31G(d,p) basis function, and 6-31+G(d,p) basis function can be used preferably.

The non-bonding potential parameters can be further grouped into parameters for van der Waals potentials and parameters for Coulomb potentials. The former are preferably determined to reproduce experimental values of a density and vaporization heat. Each of the latter parameters is the partial charge belonging to an atom, and they are preferably determined to reproduce electrostatic potentials (ESP) determined from quantum chemical calculation. As a method for reproducing ESP, a known MK method or CHelpG method can be used preferably.

For the above quantum chemical calculation, various quantum chemical calculation program packages available for a fee or free of charge can be used. For example, a general-purpose program commercially available or published under a product name such as "Gaussian98 (registered trademark)", "Gaussian03 (registered trademark)", "Gaussian09 (registered trademark)", or "GAMESS" can be used preferably.

When a method obtained by combining the molecular dynamics method and first-principle calculation is used as computer simulation, first-principle calculation may be performed with respect to all the atoms constituting atomic assembly A, or first-principle calculation may be performed with respect to a part of the atoms constituting atomic assembly A and a molecular force field method may be performed with respect to the remaining atoms constituting atomic assembly A. The former case does not require bond information for each atom, a potential parameter(s), or an atom type(s). In the latter case, it is only necessary to adjust bond information, a potential parameter(s), an atom type or the like for each atom appropriately according to an atomic range to which first-principle calculation is applied.

Examples of an ensemble to be generated by computer simulation include an NVE ensemble (the particle number N, volume V, and energy E are constant), an NVT ensemble (the particle number N, volume V, and temperature T are constant), and an NPT ensemble (the particle number N, pressure P, and volume V are constant). Note that the ensemble is a set of microscopic states that can be taken by a system (statistical set).

Examples of a boundary condition include a periodic boundary condition. When the periodic boundary condition is applied to molecular dynamics simulation, an image cell is arranged around a basic cell.

A temperature condition is set to a temperature at which the change represented by reaction formula (1) occurs. Note that the temperature is an absolute temperature represented by a unit of Kelvin (K).

The first coordinates acquisition unit 12B acquires coordinates of atomic assembly A in each of states $F_1$ to $F_i$ contained in an ensemble generated by computer simulation. Each of states $F_1$ to $F_i$ is a microscopic state generated by performing computer simulation. States $F_1$ to $F_i$ may be a part or the whole of the microscopic state generated by computer simulation.

A value of i is not particularly limited as long as being two or more, and can be selected appropriately according to the kind of free energy as a calculation target (for example, solvation free energy or binding free energy). When the free energy as a calculation target is solvation free energy, a value of i is preferably 10000 or more, more preferably 100000 or more, and still more preferably 1000000 or more. When the free energy as a calculation target is binding free energy, a value of i is preferably 100000 or more, and more preferably 1000000 or more. An upper limit value of i is not particularly limited, but is usually 10000000, and preferably 5000000.

When molecular dynamics simulation is used as computer simulation, a state of atomic assembly A changes over time from an initial state (time $T_0$) to state $F_1$ (time $T_1$), state $F_2$ (time $T_2$), ..., and state $F_i$ (time $T_i$). Coordinates of atomic assembly A in each of states $F_1$ to $F_i$ are acquired along time series. Acquired coordinates of atomic assembly A in each of states $F_1$ to $F_i$ (time $T_1$ to $T_i$) (each time) are associated with each state (each time) in which the coordinates were acquired, and are caused to be stored in the storage unit 13 by the control unit 12.

When Monte Carlo method simulation is used as computer simulation, states $F_1$ to $F_i$ are created by generating random numbers, and coordinates of atomic assembly A in each of states $F_1$ to $F_i$ are acquired. Acquired coordinates of atomic assembly A in each of states $F_1$ to $F_i$ are associated with each state in which the coordinates were acquired, and are caused to be stored in the storage unit 13 by the control unit 12.

When molecular dynamics simulation is used as computer simulation, the first coordinates acquisition unit 12B preferably performs energy minimization calculation before performing molecular dynamics simulation with respect to the first atomic assembly model. For example, the energy minimization calculation can be performed based on a function of the first simulation program 13C stored in the storage unit 13. By the energy minimization calculation, distortion of an unnatural structure contained in an initial structure of an atomic assembly model can be removed, and it is possible to avoid divergence of time integral in an initial stage of computer simulation.

When molecular dynamics simulation is used as computer simulation, the first coordinates acquisition unit 12B preferably equilibrates the first atomic assembly model (preferably an atomic assembly model after energy minimization calculation) to acquire coordinates of atomic assembly A in states $F_1$ to $F_i$ after the equilibration. For example, the first coordinates acquisition unit 12B performs computer simulation with respect to the first atomic assembly model (preferably, an atomic assembly model after energy minimization calculation). For example, when a fluctuation width of a certain physical quantity value reaches a constant value or when a certain time passes, the first coordinates acquisition unit 12B determines that the atomic assembly model has been equilibrated and acquires coordinates of atomic assembly A in states $F_1$ to $F_i$ after the equilibration.

The second coordinates acquisition unit 12C acquires coordinates of atomic assembly AB generated by connection of fragment B to atomic assembly A in each of states $F_1$ to $F_i$ based on the coordinates of atomic assembly A acquired by the first coordinates acquisition unit 12B.

Coordinates of atomic assembly AB acquired by the second coordinates acquisition unit 12C contain coordinates of all the atoms constituting atomic assembly AB. Hereinafter, coordinates of atomic assembly AB generated by connection of fragment B to atomic assembly A in state $F_x$ (x=1, 2, ..., i) may be noted by "$R_{AB}(F_x)$". Acquired coordinates of atomic assembly AB are associated with a state of atomic assembly A as a base thereof, and are caused to be stored in the storage unit 13 by the control unit 12. That is, coordinates $R_{AB}(F_1)$, $R_A(F_2)$, ..., and $R_{AB}(F_i)$ of atomic assembly AB are associated with states $F_1$, $F_2$, ..., and $F_i$, respectively, and are caused to be stored in the storage unit 13 by the control unit 12.

Atomic assembly AB generated by connection of fragment B to atomic assembly A in state $F_x$ (x=1, 2, ..., i) may be one kind of atomic assembly or two or more kinds of atomic assemblies. That is, coordinates $R_{AB}(F_x)$ may mean coordinates of atomic assembly AB generated by connection of each of the first, second, ..., and p th fragments B having different relative positions with respect to structure a to atomic assembly A in state $F_x$. p is an integer of two or more selected independently from a value of x. Therefore, p may be the same value to each other while x=1, 2, ..., i, or may be a different value from each other while x=1, 2, ..., i. The first, second, ..., and p th fragments B may be noted by "fragment $B_1$", "fragment $B_2$", ..., and "fragment $B_p$", respectively. Coordinates of atomic assembly AB generated by connection of the fragments $B_1$, $B_2$, ..., and $B_p$ to atomic assembly A in state $F_x$ may be noted by "$R_{AB}(F_x,B_1)$", "$R_{AB}(F_x,B_2)$", ..., and "$R_{AB}(F_x,B_p)$", respectively.

Coordinates of atomic assembly AB generated by connection of the fragments B to atomic assembly A in state $F_x$ may be acquired by generating atomic assembly AB actually or without generating atomic assembly AB actually. In the latter case, for example, a relative position of fragment B to be connected to atomic assembly A in state $F_x$ with respect to structure a is determined, and coordinates $R_{AB}(F_x)$ of atomic assembly AB generated by connection of fragment B to atomic assembly A in state $F_x$ can be acquired based on coordinates of atomic assembly A in state $F_x$ and the determined relative position of fragment B with respect to structure a.

A relative position of fragment B to be connected to atomic assembly A in state $F_x$ with respect to structure a is not particularly limited. However, from a viewpoint of reducing a frequency of generation of atomic assembly AB having a structure in which an atom(s) constituting atomic assembly A collides with an atom(s) constituting fragment B, it is preferable to impose a constraint condition to limit coordinates of an atom(s)constituting fragment B with respect to coordinates of an atom(s) constituting structure a.

The constraint condition is not particularly limited as long as being able to limit coordinates of an atom(s) constituting fragment B with respect to coordinates of an atom(s) constituting structure a. For example, the constraint condition may be a condition to limit coordinates of a part of atoms constituting fragment B with respect to coordinates of an atom(s) constituting structure a, or a condition to limit coordinates of all the atoms constituting fragment B with respect to coordinates of an atom(s) constituting structure a.

In an example, the second coordinates acquisition unit 12C performs the following processing repeatedly at x=1 to i:

processing W101 to define a relative position condition (for example, a distance or an angle with respect to one or more atoms constituting structure a) of atom b selected from atoms constituting fragment B with respect to structure a for fragment B to be connected to atomic assembly A in state $F_x$;

processing W102 to acquire coordinates of atom b based on the defined relative position condition;

processing W103 to acquire coordinates $R_{Ab}(F_x)$ of atomic assembly Ab generated by connection of atom b to atomic assembly A in state $F_x$ based on the acquired coordinates of atom b and coordinates $R_A(F_x)$ of atomic assembly A in state $F_x$; and processing W104 to generate coordinates of an atom(s) other than atom b, constituting fragment B by computer simulation, a known conformation generation method, or the like based on the coordinates of atom b, and to acquire coordinates $R_{AB}(F_x)$ of atomic assembly AB generated by connection of fragment B to atomic assembly A in state $F_x$. Coordinates $R_{AB}(F_1)$ to $R_{AB}(F_i)$ of atomic assembly AB generated by connection of fragment B having a limited relative position with respect to structure a can be thereby acquired for atomic assembly A in each of states $F_1$ to $F_i$.

In processing W101, the second coordinates acquisition unit 12C may define the first, second, . . . , and p th relative position conditions which are different from one another for fragment B to be connected to atomic assembly A in state $F_x$. p is an integer of two one or more selected independently from a value of x. Therefore, p may be the same value to each other while x=1, 2, . . . , i, or may be a different value from each other while x=1, 2, . . . , i.

In processing W101, when the first, second, . . . , and p th relative position conditions which are different from one another are defined for fragment B to be connected to atomic assembly A in state $F_x$, the second coordinates acquisition unit 12C performs processing W102 to W104 repeatedly for each of the first to p th relative position conditions. Coordinates $R_{AB}(F_x,B_1)$, $R_{AB}(F_x,B_2)$, . . . , and $R_{AB}(F_x,B_p)$ of atomic assembly AB generated by connection of the fragments $B_1, B_2, \ldots,$ and $B_p$ having different relative positions with respect to structure a can be thereby acquired for atomic assembly A in state $F_x$.

In another example, the second coordinates acquisition unit 12C performs the following processing:

processing W201 to create a third atomic assembly model modeling atomic assembly C consisting of structure a and fragment B connected to the structure a or containing structure a and fragment B connected to the structure a; and processing W202 to acquire coordinates of atomic assembly C (hereinafter, coordinates of atomic assembly C in states $H_1, H_2, \ldots,$ and $H_k$ may be noted by "$R_C(H_1)$", "$R_C(H_2)$", . . . , and "$R_C(H_k)$", respectively) in each of first to k th states $H_1$ to $H_k$ (wherein k is an integer of two or more) by computer simulation with respect to the created third atomic assembly model, and then performs the following processing repeatedly at x=1 to i:

processing W203 to select a selected atomic group consisting of one or more atoms selected from atoms constituting structure a (note that not only when two or more atoms are selected but also when one atom is selected is referred to as a "selected atomic group" for convenience), to rotate and/or translate coordinates of a selected atomic group of atomic assembly C in one or more states selected from states $H_1$ to $H_k$ with respect to coordinates of a selected atomic group of atomic assembly A in state $F_x$, thereby to create coordinates of atomic assembly C having the minimum sum of squares of distances between corresponding atoms between the selected atomic group of atomic assembly A and the selected atomic group of atomic assembly C (to fit coordinates of the selected atomic group of atomic assembly C to coordinates of the selected atomic group of atomic assembly A), and to superimpose atomic assembly C in one or more states selected from states $H_1$ to $H_k$ on atomic assembly A based on the created coordinates of atomic assembly C; and processing W204 to acquire coordinates of atomic assembly AB generated by connection of fragment B to atomic assembly A in state $F_x$ based on coordinates $R_A(F_x)$ of atomic assembly A in state $F_x$ and one or more coordinates of fragment B in atomic assembly C superimposed on atomic assembly A in state $F_x$. Coordinates $R_{AB}(F_1)$ to $R_{AB}(F_i)$ of atomic assembly AB generated by connection of fragment B having the limited relative position with respect to structure a can be thereby acquired for atomic assembly A in each of states $F_1$ to $F_i$.

Atomic assembly C may be constituted only of a molecule C' consisting of structure a and fragment B connected to the structure a (in this case, surrounding of the molecule C' is in vacuum), or by the molecule C' consisting of structure a and fragment B connected to the structure a and one or more kinds of other molecules (for example, a solvent molecule(s) such as a water molecule(s)).

In processing W201, the second coordinates acquisition unit 12C creates a third atomic assembly model modeling atomic assembly C. The control unit 12 causes the storage unit 13 to store data for the third atomic assembly model created by the second coordinates acquisition unit 12C (for example, coordinates of each of atoms constituting atomic assembly C, the kind thereof, a mass thereof, a partial charge thereof, and interatomic bond information).

When creating the third atomic assembly model, the second coordinates acquisition unit 12C uses data (not illustrated) for atomic assembly C that is stored in the storage unit 13. For example, the data for atomic assembly C is stored in the storage unit 13 in a form of a file that can read by the control unit 12. The data for atomic assembly C is not particularly limited as long as the third atomic assembly model modeling atomic assembly C can be created. Examples of the data for atomic assembly C include data for the molecule C' (for example, coordinates of each of atoms constituting the molecule C', the kind thereof, a mass thereof, a partial charge thereof, and interatomic bond information) and data for a surrounding environment of the molecule C' (for example, presence or absence of a solvent molecule positioned around the molecule C', the kind thereof, the number thereof, and coordinates of an atom constituting a solvent molecule).

The third atomic assembly model is not particularly limited as long as computer simulation is possible. Examples of the atomic assembly model include an all-atom model, a beads spring model, and a united atom model.

Computer simulation with respect to the third atomic assembly model is not particularly limited as long as being based on a statistical mechanics theory. Examples of representative computer simulation include a molecular dynamics method, a Monte Carlo method, and a method obtained by combining the molecular dynamics method or the Monte Carlo method and first-principle calculation. Computer simulation with respect to the third atomic assembly model can be performed in a similar manner to computer simulation with respect to the first atomic assembly model.

When molecular dynamics simulation is used as computer simulation, the second coordinates acquisition unit 12C preferably performs energy minimization calculation before performing molecular dynamics simulation with respect to the third atomic assembly model. For example, the energy minimization calculation can be performed based on a function of the first simulation program 13C stored in the storage unit 13. By the energy minimization calculation, distortion of an unnatural structure contained in an initial structure of an atomic assembly model is removed, and it is possible to avoid divergence of time integral in an initial stage of computer simulation.

When a molecular dynamics method is used as computer simulation, the second coordinates acquisition unit 12C preferably equilibrates the third atomic assembly model (preferably an atomic assembly model after energy minimization calculation) to acquire coordinates of atomic assembly C in states $H_1$ to $H_k$ after the equilibration. For example, the second coordinates acquisition unit 12C performs computer simulation with respect to the third atomic assembly model (preferably, an atomic assembly model after energy minimization calculation). For example, when a fluctuation width of a certain physical quantity value reaches a constant value or when a certain time passes, the second coordinates acquisition unit 12C determines that the atomic assembly model has been equilibrated and acquires coordinates of atomic assembly C in states $H_1$ to $H_k$ after the equilibration.

In processing W203, the second coordinates acquisition unit 12C may select p sets of coordinates having different relative positions of fragment B with respect to structure a from coordinates of atomic assembly C in states $H_1$ to $H_k$ with respect to coordinates $R_A(F_x)$ of atomic assembly A in state $F_x$. p is an integer of two or more selected independently from a value of x. Therefore, p may be the same value to each other while x=1, 2, . . . , i, or may be a different value from each other while x=1, 2, . . . , i.

In processing W203, when p sets of coordinates having different relative positions of fragment B with respect to structure a are selected from coordinates of atomic assembly C in states $H_1$ to $H_k$, the second coordinates acquisition unit 12C performs processing W203 to W204 repeatedly for each of the p sets of coordinates. Coordinates $R_{AB}(F_x,B_1)$, $R_{AB}(F_x,B_2)$, . . . , and $R_{AB}(F_x,B_p)$ of atomic assembly AB generated by connection of the fragments $B_1, B_2, \ldots,$ and $B_p$ having different relative positions with respect to structure a can be thereby acquired for atomic assembly A in state $F_x$.

In processing W203, as a method to rotate and/or translate coordinates of atomic assembly C in one or more states selected from states $H_1$ to $H_k$ with respect to coordinates $R_A(F_x)$ of atomic assembly A in state $F_x$ based on coordinates of a selected atomic group, and thereby to superimpose atomic assembly C in one or more states selected from states $H_1$ to $H_k$ on atomic assembly A, a least squares method is preferable. By using the least squares method, while a relative position relation between an atom(s) constituting a selected atomic group and an atom(s) constituting fragment B among coordinates of atomic assembly C in one or more states selected from states $H_1$ to $H_k$ is maintained, coordinates of an atom (s) constituting fragment B among coordinates of atomic assembly C in one or more states selected from states $H_1$ to $H_k$ can be added to coordinates $R_A(F_x)$ of atomic assembly A in state $F_x$. A frequency of generation of a structure in which an atom(s) constituting fragment B collides with an atom(s) constituting structure a can be thereby reduced, and fragment B can be connected to atomic assembly A. That is, a sampling efficiency can be improved, and a calculation result can be obtained with a statistically high accuracy.

A specific method of performing the least squares method is not particularly limited. For example, the least squares method can be performed as follows. When coordinates of a selected atomic group among coordinates of atomic assembly A in states $F_1$ to $F_i$ are noted by "$(x_{s\_A:n}, y_{s\_A:n}, z_{s\_A:n})$", and coordinates of a selected atomic group among coordinates of atomic assembly C in one state selected from states $H_1$ to $H_k$ are noted by "$(x_{C:n}, y_{C:n}, z_{C:n})$", by rotating and/or translating coordinates of the selected atomic group of atomic assembly C under a condition to maintain relative coordinates (internal coordinates) between atoms in the selected atomic group among coordinates of atomic assembly C, $(x_{T:n}, y_{T:n}, z_{T:n})$ are determined to minimize numerical formula (7). Here, n given as a subscript of coordinates is given to each of atoms constituting a selected atomic group, and each of coordinates $(x_{s\_A:n}, y_{s\_A:n}, z_{s\_A:n})$ and $(x_{T:n}, y_{T:n}, z_{T:n})$ represent coordinates of each of atoms constituting a selected atomic group. In addition, Cn in numerical formula (7) can be set for each of atoms constituting a selected atomic group in atomic assembly A and atomic assembly C, and is a real number of zero or more. By a relative ratio of Cn set for each of atoms constituting a selected atomic group, it is possible to set importance of coincidence of coordinates of atoms constituting a selected atomic group by the least squares method based on numerical formula (7). For example, when atoms constituting a selected atomic group contains both a heavy atom(s) (an atom(s) other than a hydrogen atom(s)) and a hydrogen atom(s), by setting Cn of the heavy atom(s) to a larger value(s) than a value(s) of the hydrogen atom(s), coincidence in the coordinates of the heavy atoms of selected atomic groups in atomic assembly A and atomic assembly C can be obtained intensively.

$$rmsd = \sum_n C_n \sqrt{(x_{S\_A:n} - x_{T:n})^2 + (y_{S\_A:n} - y_{T:n})^2 + (z_{S\_A:n} - z_{T:n})^2} \quad (7)$$

Subsequently, by rotating and/or translating an atom(s) constituting atomic assembly C such that coordinates of an atom(s) constituting a selected atomic group in atomic assembly C coincides with the coordinates $(x_{T:n}, y_{T:n}, z_{T:n})$ obtained by the least squares method, while relative coordinates (internal coordinates) between atoms constituting atomic assembly C are maintained, coordinates of an atom(s) constituting atomic assembly C is moved. By setting coordinates of an atom (s)(excluding a virtual atom(s) such as a point charge(s)) constituting fragment B in atomic assembly C to coordinates of an atom(s) constituting fragment B in atomic assembly AB, coordinates $R_{AB}(F_1)$ to $R_{AB}(F_i)$ of atomic assembly AB can be acquired.

When fragment B contains a point charge(s) (virtual atom(s)), the second coordinates acquisition unit 12C preferably adds the point charge(s) of fragment B to a charge parameter(s) of an atom(s) constituting structure a of atomic assembly A. In computer simulation, when an atom(s) constituting fragment B except for a virtual atom(s) is connected to an atom(s) constituting structure a of atomic assembly A, it may be necessary to change a partial charge(s) (charge parameter(s)) of an atom(s) constituting structure a of atomic assembly A. For example, when an atom(s) constituting fragment B except for a virtual atom(s) constitutes an electron withdrawing group or an electron donating group and where an atom(s) constituting structure a of atomistic assembly A is connected to the atom constituting fragment B, when a bond is generated between the atom constituting structure a of atomic assembly A and the atom constituting fragment B except for the virtual atom(s), usually, among the atoms constituting structure a of atomic assembly A, a partial charge (charge parameter) of an atom connected to fragment B and/or an atom(s) around the atom connected to fragment B (for example, among atoms constituting atomic assembly A, an atom connected to an atom connected to an atom constituting fragment B except for a virtual atom(s)) changes. A method in which an atom(s) constituting structure a, having a partial charge(s) (charge parameter(s)) changed depending on presence or absence of a bond with fragment B is handled as an atom(s) (existent atom(s)) constituting fragment B, and is not handled as an atom(s) constituting structure a is considered. However, by containing a point charge(s) having an equal charge(s) to the change amount of the partial charge(s) (charge parameter(s)) of the atom(s) as an atom(s) (virtual atom(s)) constituting fragment B, a change between atomic assembly AB (final state) and atomic assembly A (initial state) can be reduced. Therefore, calculation accuracy can be improved.

The first interaction energy $\phi$ frequency distribution creation unit 12D calculates interaction energy $\phi$ between structure a and fragment B connected to the structure a based on the coordinates of atomic assembly AB acquired by the second coordinates acquisition unit 12C, and creates a frequency distribution indicating a frequency in each class of interaction energy $\phi$. The control unit 12 causes the storage unit 13 to store the calculated interaction energy $\phi$ and the created frequency distribution. Each class of interaction energy $\phi$ is associated with coordinates of atomic assembly AB as a base of calculation thereof, and is caused to be stored in the storage unit 13 by the control unit 12.

Interaction energy $\phi$ is calculated for each of coordinates $R_{AB}(F_1)$ to $R_{AB}(F_i)$ of atomic assembly AB. For example, interaction energy $\phi$ can be calculated based on a function of the first simulation program 13C stored in the storage unit 13. When interaction energy $\phi$ is calculated, a simulation program and a potential parameter(s) used are not particularly limited. However, coordinates of atomic assembly AB are determined by computer simulation performed by the first coordinates acquisition unit 12B. Therefore, it is preferable to use the same simulation program and potential parameter(s) as those used in computer simulation performed by the first coordinates acquisition unit 12B.

For example, a frequency distribution indicating a frequency in each class of interaction energy $\phi$ can be created as a histogram in which the horizontal axis indicates each class of interaction energy $\phi$ and the vertical axis indicates a frequency in each class of interaction energy $\phi$.

For example, each class of interaction energy $\phi$ can be created with interaction energy $\phi$ positioned in the center while an interaction energy section [$\phi$−$\Delta\phi$/2 to $\phi$+$\Delta\phi$/2] with an interaction energy interval $\Delta\phi$ is used as a class interval. $\Delta\phi$ in each interaction energy section may be constant in all the sections, or may be changed appropriately according to an interaction energy section. To perform calculation in the second term in numerical formula (1), a $P_0(\phi)$ class interval $\Delta\phi$ is preferably the same as a $P(\phi)$ class interval $\Delta\phi$, and the $P(\phi)$ class interval $\Delta\phi$ is preferably caused to be the same as the $P_0(\phi)$ class interval $\Delta\phi$. The number of division of interaction energy $\phi$, that is, the number of the class interval $\Delta\phi$ is not particularly limited, but is preferably from 50 to 500, and more preferably from 250 to 500.

The second term in numerical formula (1) includes a calculation process of dividing an appearance probability $P(\phi)$ of interaction energy $\phi$ by an appearance probability $P_0(\phi)$ of interaction energy $\phi$. Therefore, when there is an interaction energy section in which $P(\phi)$ is not zero and $P_0(\phi)$ is zero, the second term in numerical formula (1) diverges, and free energy calculation based on numerical formula (1) is not possible. Therefore, in all the interaction energy sections [$\phi$−$\Delta\phi$/2 to $\phi$+$\Delta\phi$/2], it is preferable to set $\Delta\phi$ for each interaction energy section appropriately such that $P_0(\phi)$ is constant. By setting $\Delta\phi$ for each interaction energy section appropriately and causing the $P(\phi)$ class interval $\Delta\phi$ to be the same as the $P_0(\phi)$ class interval $\Delta\phi$, a calculation result can be obtained with a statistically high accuracy.

The first interaction energy $\phi$ appearance probability calculation unit 12E calculates an appearance probability $P_0(\phi)$ in each class of interaction energy $\phi$ based on the frequency distribution created by the first interaction energy $\phi$ frequency distribution creation unit 12D. The control unit 12 causes the storage unit 13 to store the calculated $P_0(\phi)$.

By normalizing a frequency distribution indicating a frequency in each class of interaction energy $\phi$, the first interaction energy $\phi$ appearance probability calculation unit 12E can calculate an appearance probability $P_0(\phi)$ in each class of interaction energy $\phi$. Here, normalization means dividing a frequency in each class of interaction energy $\phi$ in a frequency distribution by the sum of frequencies in classes of interaction energy $\phi$.

The first interaction energy $\epsilon$ frequency distribution creation unit 12F calculates interaction energy $\epsilon$ between a part or the whole of an atomic assembly generated by removing structure aB consisting of structure a and fragment B connected to the structure a from atomic assembly AB, and fragment B based on the coordinates of atomic assembly AB acquired by the second coordinates acquisition unit 12C, and creates a frequency distribution indicating a frequency in each class of interaction energy $\epsilon$ in each class of interaction energy $\phi$ in the frequency distribution created by the first interaction energy $\phi$ frequency distribution creation unit 12D. The control unit 12 causes the storage unit 13 to store the calculated interaction energy $\epsilon$ and the created frequency distribution.

In an example, the first interaction energy $\epsilon$ frequency distribution creation unit 12F calculates interaction energy $\epsilon$ between a part or the whole of an atomic assembly generated by removing structure aB consisting of structure a and fragment B connected to the structure a from atomic assembly AB, and fragment B for each of coordinates $R_{AB}(F_1)$ to $R_{AB}(F_i)$ of atomic assembly AB based on the coordinates of atomic assembly AB acquired by the second coordinates acquisition unit 12C, then extracts interaction energy ε between a part or the whole of an atomic assembly generated by removing structure aB consisting of structure a and fragment B connected to the structure a from atomic assembly AB, and fragment B in each class of interaction energy φ based on the frequency distribution created by the first interaction energy φ frequency distribution creation unit 12D, and creates a frequency distribution indicating a frequency in each class of interaction energy ε in each class of interaction energy φ in the frequency distribution created by the first interaction energy φ frequency distribution creation unit 12D.

In another example, the first interaction energy ε frequency distribution creation unit 12F extracts coordinates of atomic assembly AB belonging to each class of interaction energy φ from the coordinates of atomic assembly AB acquired by the second coordinates acquisition unit 12C based on the frequency distribution created by the first interaction energy φ frequency distribution creation unit 12D, then calculates interaction energy ε between a part or the whole of an atomic assembly generated by removing structure aB consisting of structure a and fragment B connected to the structure a from atomic assembly AB, and fragment B in each class of interaction energy φ based on the extracted coordinates of atomic assembly AB, and creates a frequency distribution indicating a frequency in each class of interaction energy ε in each class of interaction energy φ in the frequency distribution created by the first interaction energy φ frequency distribution creation unit 12D.

When atomic assembly AB is constituted of a ligand(s) and a solvent molecule(s) (for example, a water molecule(s)), and structure aB consisting of structure a and fragment B connected to the structure a is the ligand(s), interaction energy ε between a part or the whole of an atomic assembly generated by removing structure aB consisting of structure a and fragment B connected to the structure a from atomic assembly AB, and fragment B means an interaction energy between fragment B and each water molecule present around fragment B. When atomic assembly AB is constituted of a ligand(s), a protein(s), and a water molecule(s), and structure aB consisting of structure a and fragment B connected to the structure a is the ligand, interaction energy ε between a part or the whole of an atomic assembly generated by removing structure aB consisting of structure a and fragment B connected to the structure a from atomic assembly AB, and fragment B means an interaction energy between fragment B and each water molecule, and an interaction energy between fragment B and the protein(s). Specific examples of interaction energy ε, exemplified here are applied not only to interaction energy ε calculated by the first interaction energy ε frequency distribution creation unit 12F but also to interaction energy ε calculated by the second interaction energy ε frequency distribution creation unit 12L.

Interaction energy ε is calculated for all the classes of interaction energy φ included in the frequency distribution (for example, histogram) created by the first interaction energy φ frequency distribution creation unit 12D. For example, interaction energy ε can be calculated based on a function of the first simulation program 13C stored in the storage unit 13. When interaction energy ε is calculated, a simulation program and a potential parameter(s) used are not particularly limited. However, coordinates of atomic assembly AB are determined by computer simulation performed by the first coordinates acquisition unit 12B. Therefore, it is preferable to use the same simulation program and potential parameter(s) as those used in computer simulation performed by the first coordinates acquisition unit 12B.

The frequency distribution indicating a frequency in each class of interaction energy ε is created for interaction energy ε in each class of interaction energy φ. For example, a frequency distribution indicating a frequency in each class of interaction energy ε can be created as a histogram in which the horizontal axis indicates each class of interaction energy ε and the vertical axis indicates a frequency in each class of interaction energy ε.

For example, each class of interaction energy ε can be created with interaction energy ε positioned in the center while an interaction energy section [ε−Δε/2 to ε+Δε/2] with an interaction energy interval Δε is used as a class interval. Δε in each interaction energy section may be constant in all the sections, or may be changed appropriately according to an interaction energy section. The number of division of interaction energy ε, that is, the number of the class intervals Δε is not particularly limited because of depending on the number of snapshots obtained by simulation, the number of water molecules or the like around fragment B, an energy section width of interaction energy ε or the like. However, the number is preferably 500 to 5000, and more preferably 2000 to 5000.

The first interaction energy ε appearance probability calculation unit 12G calculates an appearance probability $P_0'(\varepsilon;\phi)$ in each class of interaction energy ε in each class of interaction energy φ based on a frequency distribution created by the first interaction energy ε frequency distribution creation unit 12F. The control unit 12 causes the storage unit 13 to store the calculated $P_0'(\varepsilon;\phi)$. Note that "φ" in $P_0'(\varepsilon;\phi)$ is a notation to clarify that an appearance probability $P_0'(\varepsilon;\phi)$ in each class of interaction energy ε is calculated for each class of interaction energy φ.

By normalizing a frequency distribution indicating a frequency in each class of interaction energy ε, the first interaction energy ε appearance probability calculation unit 12G can calculate an appearance probability $P_0'(\varepsilon;\phi)$ in each class of interaction energy ε. Here, normalization means dividing a frequency in each class of interaction energy ε in a frequency distribution by the sum of frequencies in classes of interaction energy ε.

The second atomic assembly model creation unit 12H creates a second atomic assembly model modeling atomic assembly AB after the change. The control unit 12 causes the storage unit 13 to store data for the second atomic assembly model created by the second atomic assembly model creation unit 12H (for example, coordinates of each of atoms constituting atomic assembly AB, the kind thereof, a mass thereof, a partial charge thereof, and interatomic bond information).

When creating the second atomic assembly model, the second atomic assembly model creation unit 12H uses the data 13D for atomic assembly AB after the change that is stored in the storage unit 13. For example, the data 13D for atomic assembly AB after the change is stored in the storage unit 13 in a form of a file that can read by the control unit 12. The data 13D for atomic assembly AB after the change is not particularly limited as long as the second atomic assembly model modeling atomic assembly AB after the change can be created. Examples of the data 13D for atomic assembly AB after the change include coordinates of each of atoms constituting atomic assembly AB, the kind thereof, a mass thereof, a partial charge thereof, and interatomic bond information.

The second atomic assembly model is not particularly limited as long as computer simulation is possible.

Examples of the atomic assembly model include an all-atom model, a beads spring model, and a united atom model. The beads spring model is a model in which a monomer unit constituting atomic assembly AB is assumed to be one bead (segment) and the beads are connected with a virtual spring(s), and that the united atom model is a model in which a hydrogen atom is included in a heavy atom (for example, a carbon atom) and is handled as one atom (mass point).

The third coordinates acquisition unit 12I acquires coordinates of atomic assembly AB in each of first to j th states $G_1$ to $G_j$ (wherein j is an integer of two or more) by a snapshot output as a result of computer simulation with respect to the second atomic assembly model created by the second atomic assembly model creation unit 12H. Here, the snapshot includes coordinates of all the atoms constituting atomic assembly AB. That is, the snapshot in each of states $G_1$ to $G_j$ includes coordinates of all the atoms constituting atomic assembly AB in each of states $G_1$ to $G_j$. Hereinafter, coordinates of atomic assembly AB in states $G_1, G_2, \ldots,$ and $G_j$ may be referred to as coordinates $R_{AB}(G_1), R_{AB}(G_2), \ldots, $ and $R_{AB}(G_j)$, respectively. The control unit 12 causes the storage unit 13 to store the coordinates of atomic assembly AB, acquired by the third coordinates acquisition unit.

Computer simulation performed by the third coordinates acquisition unit 12I is not particularly limited as long as being based on a statistical mechanics theory. Examples of representative computer simulation include a molecular dynamics method, a Monte Carlo method, and a method obtained by combining the molecular dynamics method or the Monte Carlo method and first-principle calculation.

The third coordinates acquisition unit 12I performs computer simulation based on data for the second atomic assembly model, the data 13E for the second simulation condition, the second simulation program 13F and the like that stored in the storage unit 13. The data 13E for the simulation condition is stored in the storage unit 13 in a form of a file that can read by the control unit 12.

The simulation condition is not particularly limited as long as computer simulation can be performed. Specific description of computer simulation is similar to that of computer simulation performed by the first coordinates acquisition unit 12B, and will be omitted.

The third coordinates acquisition unit 12I acquires coordinates of atomic assembly AB in each of states $G_1$ to $G_j$ contained in an ensemble generated by computer simulation. Each of states $G_1$ to $G_j$ is a microscopic state generated by performing computer simulation. States $G_1$ to $G_j$ may be a part or the whole of the microscopic state generated by computer simulation.

A value of j is not particularly limited as long as being two or more, and can be selected appropriately according to the kind of free energy as a calculation target (for example, solvation free energy or binding free energy). When the free energy as a calculation target is solvation free energy, a value of j is preferably 10000 or more, and more preferably 100000 or more. When the free energy as a calculation target is binding free energy, a value of j is preferably 100000 or more, and more preferably 1000000 or more. An upper limit value of j is not particularly limited, but is usually 10000000, and preferably 5000000.

When a molecular dynamics method is used as computer simulation, a state of atomic assembly AB changes over time from an initial state (time $T_0$) to state $G_1$ (time $T_1$), state $G_2$ (time $T_2$), \ldots, and state $G_j$ (time $T_j$). Coordinates of atomic assembly AB in each of states $G_1$ to $G_j$ are acquired along time series. Acquired coordinates of atomic assembly AB in each of states $G_1$ to $G_j$ (time $T_1$ to $T_j$) (each time) are associated with each state (each time) in which the coordinates were acquired, and are caused to be stored in the storage unit 13 by the control unit 12.

When a Monte Carlo method is used as computer simulation, states $G_1$ to $G_j$ are created by generating random numbers, and coordinates of atomic assembly AB in each of states $G_1$ to $G_j$ are acquired. Acquired coordinates of atomic assembly AB in each of states $G_1$ to $G_j$ are associated with each state in which the coordinates were acquired, and are caused to be stored in the storage unit 13 by the control unit 12.

When a molecular dynamics method is used as computer simulation, the third coordinates acquisition unit 12I preferably performs energy minimization calculation before performing molecular dynamics simulation with respect to the second atomic assembly model. For example, the energy minimization calculation can be performed based on a function of the second simulation program 13F stored in the storage unit 13. By the energy minimization calculation, distortion of an unnatural structure contained in an initial structure of an atomic assembly model is removed, and it is possible to avoid divergence of time integral in an initial stage of computer simulation.

When a molecular dynamics method is used as computer simulation, the third coordinates acquisition unit 12I preferably equilibrates the second atomic assembly model (preferably, an atomic assembly model after energy minimization calculation) to acquire coordinates of atomic assembly AB in states $G_1$ to $G_j$ after the equilibration. For example, the third coordinates acquisition unit 12I performs computer simulation with respect to the second atomic assembly model (preferably, an atomic assembly model after energy minimization calculation). For example, when a certain physical quantity reaches a threshold value or when a certain time passes, the third coordinates acquisition unit 12I determines that the atomic assembly model has been equilibrated and acquires coordinates of atomic assembly AB in states $G_1$ to $G_j$ after the equilibration.

The second interaction energy φ frequency distribution creation unit 12J calculates interaction energy φ between structure a and fragment B connected to the structure a based on the coordinates of atomic assembly AB acquired by the third coordinates acquisition unit 12I, and creates a frequency distribution indicating a frequency in each class of interaction energy φ. Each class of interaction energy φ is associated with coordinates of atomic assembly AB as a base of calculation thereof, and is caused to be stored in the storage unit 13 by the control unit 12.

Interaction energy φ is calculated for each of coordinates $R_{AB}(G_1)$ to $R_{AB}(G_j)$ of atomic assembly AB. For example, interaction energy φ can be calculated based on a function of the second simulation program 13F. When interaction energy φ is calculated, a simulation program and a potential parameter(s) used are not particularly limited. However, coordinates of atomic assembly AB are determined by computer simulation performed by the third coordinates acquisition unit 12I. Therefore, it is preferable to use the same simulation program and potential parameter(s) as those used in computer simulation performed by the third coordinates acquisition unit 12I.

For example, a frequency distribution indicating a frequency in each class of interaction energy φ can be created as a histogram in which the horizontal axis indicates each class of interaction energy φ and the vertical axis indicates a frequency in each class of interaction energy φ.

For example, each class of interaction energy φ can be created with interaction energy φ positioned in the center while an interaction energy section [$\phi-\Delta\phi/2$ to $\phi+\Delta\phi/2$] with an interaction energy interval $\Delta\phi$ is used as a class interval. $\Delta\phi$ in each interaction energy section may be constant in all the sections, or may be changed appropriately according to an interaction energy section. To perform calculation in the second term in numerical formula (1), a $P_0(\phi)$ class interval $\Delta\phi$ is preferably the same as a $P(\phi)$ class interval $\Delta\phi$, and the $P(\phi)$ class interval $\Delta\phi$ is more preferably caused to be the same as the $P_0(\phi)$ class interval $\Delta\phi$. The number of division of interaction energy $\phi$, that is, the number of the class interval $\Delta\phi$ is not particularly limited, but is preferably 50 to 500, and more preferably 250 to 500.

The second term in numerical formula (1) includes a calculation process for dividing an interaction energy appearance probability $P(\phi)$ by an interaction energy appearance probability $P_0(\phi)$. Therefore, when there is an interaction energy section in which $P(\phi)$ is not zero and the interaction energy appearance probability $P_0(\phi)$ is zero, the second term in numerical formula (1) diverges, and free energy calculation based on numerical formula (1) is not possible. Therefore, in all the interaction energy sections [$\phi-\Delta\phi/2$ to $\phi+\Delta\phi/2$], it is preferable to set $\Delta\phi$ for each interaction energy section appropriately such that $P_0(\phi)$ is constant. By setting $\Delta\phi$ for each interaction energy section appropriately and causing the $P(\phi)$ class interval $\Delta\phi$ to be the same as the $P_0(\phi)$ class interval $\Delta\phi$, a calculation result can be obtained with a statistically high accuracy.

The second interaction energy $\phi$ appearance probability calculation unit 12K calculates an appearance probability $P(\phi)$ in each class of interaction energy $\phi$ based on a frequency distribution created by the second interaction energy $\phi$ frequency distribution creation unit 12J. The control unit 12 causes the storage unit 13 to store the calculated $P(\phi)$.

By normalizing a frequency distribution indicating a frequency in each class of interaction energy $\phi$, the second interaction energy $\phi$ appearance probability calculation unit 12K can calculate an appearance probability $P(\phi)$ in each class of interaction energy $\phi$. Here, normalization means dividing a frequency in each class of interaction energy $\phi$ in a frequency distribution by the sum of frequencies in classes of interaction energy $\phi$.

The second interaction energy $\varepsilon$ frequency distribution creation unit 12L calculates interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the third coordinates acquisition unit 12I, and creates a frequency distribution indicating a frequency in each class of interaction energy $\varepsilon$. The control unit 12 causes the storage unit 13 to store the calculated interaction energy $\varepsilon$ and the created frequency distribution.

The second interaction energy $\varepsilon$ frequency distribution creation unit 12L may calculate interaction energy $\varepsilon$ with or without associating interaction energy $\varepsilon$ with each class of interaction energy $\phi$ in the frequency distribution created by the second interaction energy $\phi$ frequency distribution creation unit 12J. When interaction energy $\varepsilon$ is calculated by being associated with each class of interaction energy $\phi$, interaction energy $\varepsilon$ is calculated for all the classes of interaction energy $\phi$ included in the frequency distribution (for example, histogram) created by the second interaction energy $\phi$ frequency distribution creation unit 12J, and the frequency distribution indicating a frequency in each class of interaction energy $\varepsilon$ is created for interaction energy $\varepsilon$ in each class of interaction energy $\phi$.

When interaction energy $\varepsilon$ is calculated without being associated with each class of interaction energy $\phi$, the second interaction energy $\varepsilon$ frequency distribution creation unit 12L calculates interaction energy $\varepsilon$ between a part or the whole of an atomic assembly generated by removing structure aB consisting of structure a and fragment B connected to the structure a from atomic assembly AB, and fragment B for each of the coordinates $R_{AB}(G_1)$ to $R_{AB}(G_j)$ of atomic assembly AB, based on the coordinates of atomic assembly AB acquired by the third coordinates acquisition unit 12I, and creates a frequency distribution indicating a frequency in each class of interaction energy $\varepsilon$.

When interaction energy $\varepsilon$ is calculated by being associated with each class of interaction energy $\phi$, the second interaction energy $\varepsilon$ frequency distribution creation unit 12L calculates interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the third coordinates acquisition unit 12I, and creates a frequency distribution indicating a frequency in each class of interaction energy $\varepsilon$ in each class of interaction energy $\phi$ in the frequency distribution created by the second interaction energy $\phi$ frequency distribution creation unit 12J.

In an example, the second interaction energy $\varepsilon$ frequency distribution creation unit 12L calculates interaction energy $\varepsilon$ between a part or the whole of an atomic assembly generated by removing structure aB consisting of structure a and fragment B connected to the structure a from atomic assembly AB, and fragment B based on the coordinates of atomic assembly AB acquired by the third coordinates acquisition unit 12I for each of coordinates $R_{AB}(G_1)$ to $R_{AB}(G_j)$ of atomic assembly AB, then extracts interaction energy $\varepsilon$ between a part or the whole of an atomic assembly generated by removing structure aB consisting of structure a and fragment B connected to the structure a from atomic assembly AB, and fragment B in each class of interaction energy $\phi$ based on the frequency distribution created by the second interaction energy $\phi$ frequency distribution creation unit 12J, and creates a frequency distribution indicating a frequency in each class of interaction energy $\varepsilon$ in each class of interaction energy $\phi$ in the frequency distribution created by the second interaction energy $\phi$ frequency distribution creation unit 12J.

In another example, the second interaction energy $\varepsilon$ frequency distribution creation unit 12L extracts coordinates of atomic assembly AB belonging to each class of interaction energy $\phi$ from the coordinates of atomic assembly AB acquired by the third coordinates acquisition unit 12I based on the frequency distribution created by the second interaction energy $\phi$ frequency distribution creation unit 12J, then calculates interaction energy $\varepsilon$ between a part or the whole of an atomic assembly generated by removing structure aB consisting of structure a and fragment B connected to the structure a from atomic assembly AB, and fragment B in each class of interaction energy $\phi$ based on the extracted coordinates of atomic assembly AB, and creates a frequency distribution indicating a frequency in each class of interaction energy $\varepsilon$ in each class of interaction energy $\phi$ in the frequency distribution created by the second interaction energy $\phi$ frequency distribution creation unit 12J.

For example, interaction energy $\varepsilon$ can be calculated based on a function of the second simulation program 13F. When interaction energy $\varepsilon$ is calculated, a simulation program and a potential parameter used are not particularly limited. However, coordinates of atomic assembly AB are determined by computer simulation performed by the third coordinates acquisition unit 12I. Therefore, it is preferable to use the same simulation program and potential parameter(s)r as those used in computer simulation performed by the third coordinates acquisition unit 12I.

For example, a frequency distribution indicating a frequency in each class of interaction energy $\varepsilon$ can be created as a histogram in which the horizontal axis indicates each class of interaction energy $\varepsilon$ and the vertical axis indicates a frequency in each class of interaction energy $\varepsilon$.

For example, each class of interaction energy $\varepsilon$ can be created with interaction energy $\varepsilon$ positioned in the center while an interaction energy section $[\varepsilon-\Delta\varepsilon/2$ to $\varepsilon+\Delta\varepsilon/2]$ with an interaction energy interval $\Delta\varepsilon$ is used as a class interval. $\Delta\varepsilon$ in each interaction energy section may be constant in all the sections, or may be changed appropriately according to an interaction energy section. In addition, a $P_0'(\varepsilon;\phi)$ class interval $\Delta\varepsilon$ is preferably the same as a $P'(\varepsilon)$ class interval $\Delta\varepsilon$. The number of division of interaction energy $\varepsilon$, that is, the number of the class intervals $\Delta\varepsilon$ is not particularly limited because of depending on the number of snapshots obtained by simulation, the number of water molecules around fragment B, an energy section width of interaction energy $\varepsilon$ or the like. However, the number is preferably 500 to 5000, and more preferably 2000 to 5000.

The second interaction energy $\varepsilon$ appearance probability calculation unit 12M calculates an appearance probability $P'(\varepsilon)$ in each class of interaction energy $\varepsilon$ based on a frequency distribution created by the second interaction energy $\varepsilon$ frequency distribution creation unit 12L. The control unit 12 causes the storage unit 13 to store the calculated $P'(\varepsilon)$.

By normalizing a frequency distribution indicating a frequency in each class of interaction energy $\varepsilon$, the second interaction energy $\varepsilon$ appearance probability calculation unit 12M can calculate an appearance probability $P'(\varepsilon)$ in each class of interaction energy $\varepsilon$. Here, normalization means dividing a frequency in each class of interaction energy $\varepsilon$ in a frequency distribution by the sum of frequencies in classes of interaction energy $\varepsilon$.

When the second interaction energy $\varepsilon$ frequency distribution creation unit 12L calculates interaction energy $\varepsilon$ without associating interaction energy $\varepsilon$ with each class of interaction energy $\phi$ in the frequency distribution created by the second interaction energy $\phi$ frequency distribution creation unit 12J, the second interaction energy $\varepsilon$ appearance probability calculation unit 12M calculates an appearance probability $P'(\varepsilon)$ in each class of interaction energy $\varepsilon$ without associating the appearance probability $P'(\varepsilon)$ with each class of interaction energy $\phi$ based on the frequency distribution created by the second interaction energy $\varepsilon$ frequency distribution creation unit 12L.

When the second interaction energy $\varepsilon$ frequency distribution creation unit 12L calculates interaction energy $\varepsilon$ by associating interaction energy $\varepsilon$ with each class of interaction energy $\phi$ in the frequency distribution created by the second interaction energy $\phi$ frequency distribution creation unit 12J, the second interaction energy $\varepsilon$ appearance probability calculation unit 12M calculates an appearance probability $P'(\varepsilon;\phi)$ in each class of interaction energy $\varepsilon$ in each class of interaction energy $\phi$ based on the frequency distribution created by the second interaction energy $\varepsilon$ frequency distribution creation unit 12L. Note that "$\phi$" in $P'(\varepsilon;\phi)$ is a notation to clarify that an appearance probability $P'(\varepsilon;\phi)$ in each class of interaction energy $\varepsilon$ is calculated for each class of interaction energy $\phi$.

The $\int\Delta v(\phi)P(\phi)d\phi$ calculation unit 12N calculates a free energy change amount $\int\Delta v(\phi)P(\phi)d\phi$ caused by interaction energy $\varepsilon$ based on $P(\phi)$ calculated by the second interaction energy $\phi$ appearance probability calculation unit 12K, $P_0'(\varepsilon;\phi)$ calculated by the first interaction energy $\varepsilon$ appearance probability calculation unit 12G, and $P'(\varepsilon)$ calculated by the second interaction energy $\varepsilon$ appearance probability calculation unit 12M.

"$\Delta v(\phi)$" in "$\int\Delta v(\phi)P(\phi)d\phi$" indicates a free energy change amount caused by interaction energy $\varepsilon$ in each class of interaction energy $\phi$. When atomic assembly AB is constituted of a ligand(s) and a solvent molecule(s) (for example, a water molecule(s)), and structure aB consisting of structure a and fragment B connected to the structure a is the ligand(s), the free energy change amount caused by interaction energy $\varepsilon$ means a free energy change amount caused by an interaction energy between fragment B and a water molecule(s) present around fragment B. When atomic assembly AB is constituted of a ligand(s), a protein(s), and a water molecule(s), and structure aB consisting of structure a and fragment B connected to the structure a is the ligand(s), the free energy change amount caused by interaction energy $\varepsilon$ means the sum of a free energy change amount caused by an interaction energy between fragment B and the water molecule(s) and a free energy change amount caused by an interaction energy between fragment B and the protein(s).

The $\int\Delta v(\phi)P(\phi)d\phi$ calculation unit 12N preferably calculates a free energy change amount $\int\Delta v(\phi)P(\phi)d\phi$ caused by interaction energy $\varepsilon$ based on $P(\phi)$ calculated by the second interaction energy $\phi$ appearance probability calculation unit 12K, $P_0'(\varepsilon;\phi)$ calculated by the first interaction energy $\varepsilon$ appearance probability calculation unit 12G, and $P'(\varepsilon)$ calculated by the second interaction energy $\varepsilon$ appearance probability calculation unit 12M by the energy representation method.

In an example, the $\int\Delta v(\phi)P(\phi)d\phi$ calculation unit 12N does not calculate $\Delta v(\phi)$, but calculates $\int\Delta v(\phi)P(\phi)d\phi$ based on $P(\phi)$ calculated by the second interaction energy $\phi$ appearance probability calculation unit 12K, $P_0'(\varepsilon;\phi)$ calculated by the first interaction energy $\varepsilon$ appearance probability calculation unit 12G, and $P'(\varepsilon)$ calculated by the second interaction energy $\varepsilon$ appearance probability calculation unit 12M by the energy representation method. $P'(\varepsilon)$ used here is an appearance probability in each class of interaction energy $\varepsilon$ calculated without being associated with each class of interaction energy $\phi$.

In another example, the $\int\Delta v(\phi)P(\phi)d\phi$ calculation unit 12N calculates a free energy change amount $\Delta v(\phi)$ caused by interaction energy $\varepsilon$ in each class of interaction energy $\phi$ based on $P_0'(\varepsilon;\phi)$ calculated by the first interaction energy $\varepsilon$ appearance probability calculation unit 12G and $P'(\varepsilon;\phi)$ calculated by the second interaction energy $\varepsilon$ appearance probability calculation unit 12M, and calculates $\int\Delta v(\phi)P(\phi)d\phi$ based on the calculated $\Delta v(\phi)$ and $P(\phi)$ calculated by the second interaction energy $\phi$ appearance probability calculation unit 12K. At this time, the $\int\Delta v(\phi)P(\phi)d\phi$ calculation unit 12N preferably calculates a free energy change amount $\Delta v(\phi)$ caused by interaction energy $\varepsilon$ in each class of interaction energy $\phi$ based on $P_0'(\varepsilon;\phi)$ calculated by the first interaction energy $\varepsilon$ appearance probability calculation unit 12G and $P'(\varepsilon;\phi)$ calculated by the second interaction energy $\varepsilon$ appearance probability calculation unit 12M by the energy representation method.

The $\Delta G$ calculation unit 12O calculates $\Delta G$ based on $P_0(\phi)$ calculated by the first interaction energy $\phi$ appearance probability calculation unit 12E, $P(\phi)$ calculated by the second interaction energy ɸ appearance probability calculation unit 12K, ∫Δv(ɸ)P(ɸ)dɸ calculated by the ∫Δv(ɸ)P(ɸ)dɸ calculation unit 12N, and numerical formula (1):

$$\Delta G = \int \phi P(\phi)d\phi + RT \int P(\phi)\log\left(\frac{P(\phi)}{P_0(\phi)}\right)d\phi + \int \Delta v(\phi)P(\phi)d\phi \quad (1)$$

wherein R represents a gas constant, and T represents an absolute temperature at which the change represented by reaction formula (1) occurs.

Hereinafter, a calculation processing procedure according to an example is described based on the drawings.

Figure 2:
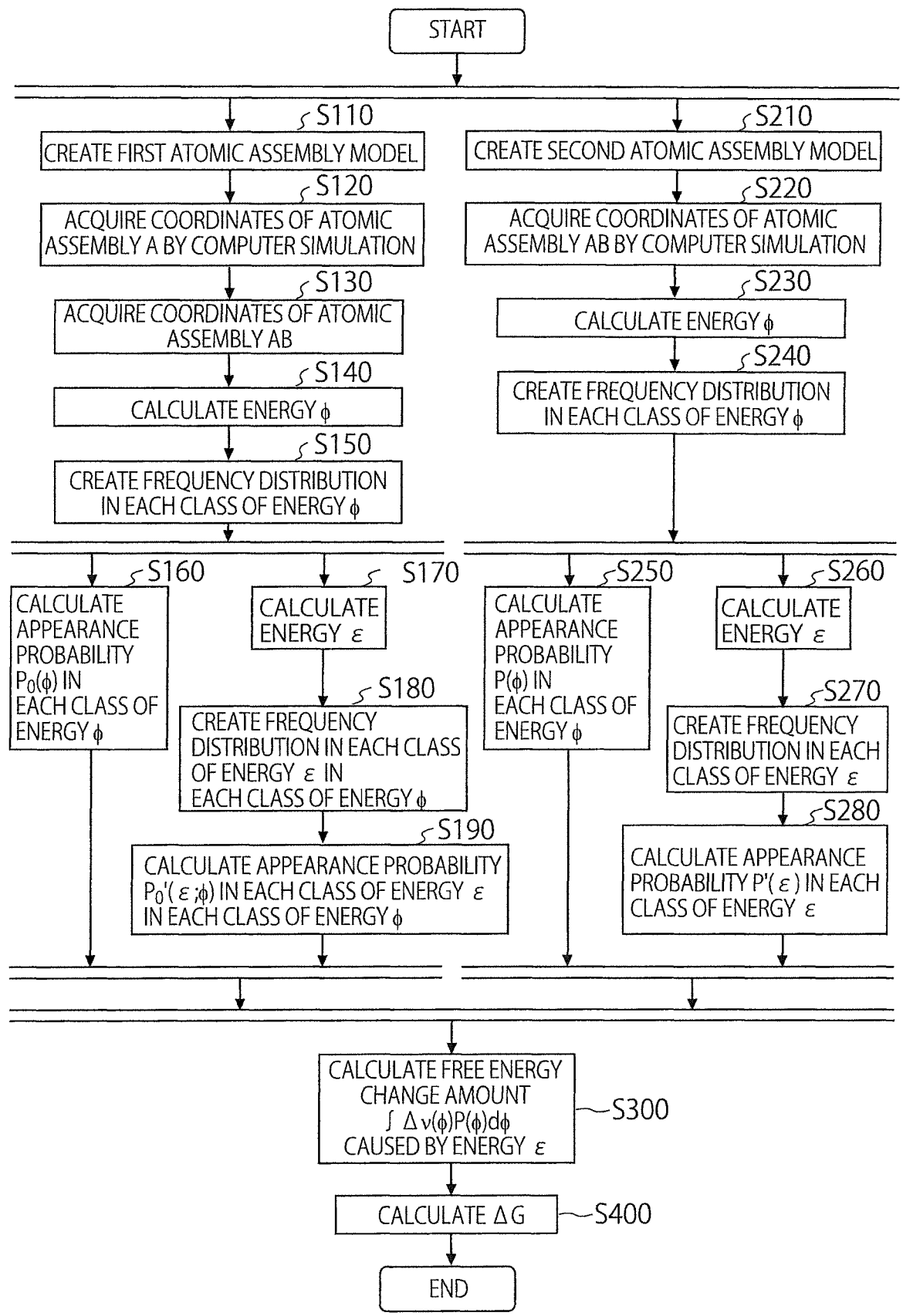
FIG. 2 is a flowchart illustrating a processing procedure of the calculation device according to the example.

FIG. 2 is a flowchart illustrating a processing procedure of the calculation device 1 according to this example.

When the control unit 12 performs calculation processing for atomic assembly A before the change (steps S110 to 190) and calculation processing for atomic assembly AB after the change (steps S210 to 280), the control unit 12 may perform one processing and then may perform the other processing, or may perform both the processing in parallel.

Hereinafter, steps S110 to S150 are described.

The control unit 12 performs steps S110 to S150 sequentially.

In step S110, the control unit 12 creates the first atomic assembly model modeling atomic assembly A before the change using the data 13A for atomic assembly A before the change that is stored in the storage unit 13. The control unit 12 causes the storage unit 13 to store the created data for the first atomic assembly model. In step S110, the control unit 12 functions as the first atomic assembly model creation unit 12A.

In step S120, the control unit 12 acquires coordinates of atomic assembly A in each of first to i th states $F_1$ to $F_i$ (wherein i is an integer of two or more) by computer simulation with respect to the first atomic assembly model using data for the first atomic assembly model, the data 13B for the first simulation condition, the first simulation program 13C and the like that are stored in the storage unit 13. In step S120, the control unit 12 functions as the first coordinates acquisition unit 12B.

Figure 3:
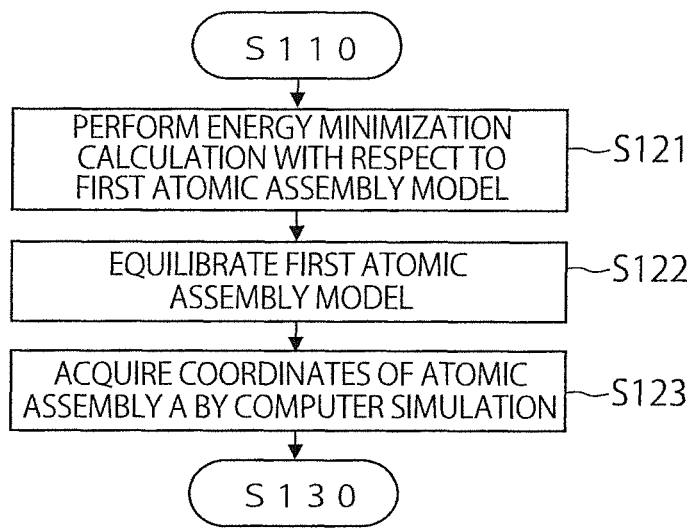
FIG. 3 is a flowchart illustrating an example of a processing procedure in step S120.

FIG. 3 illustrates an example of step S120 performed by the control unit 12 when a molecular dynamics method is used as computer simulation. In this example, after step S110, the control unit 12 performs energy minimization calculation with respect to the first atomic assembly model (step S121), and subsequently equilibrates the first atomic assembly model (step S122) to acquire coordinates of atomic assembly A in each of states $F_1$ to $F_i$ after the equilibration by computer simulation with respect to the first atomic assembly model after the equilibration. In step S122, for example, when a certain physical quantity in the first atomic assembly model reaches a threshold value or when a certain time passes after start of computer simulation, the control unit 12 determines that the first atomic assembly model has been equilibrated.

In step S130, the control unit 12 acquires coordinates of atomic assembly AB generated by connection of fragment B to atomic assembly A in each of states $F_1$ to $F_i$ based on the coordinates of atomic assembly A acquired in step S120. In step S130, the control unit 12 functions as the second coordinates acquisition unit 12C.

Figure 4:
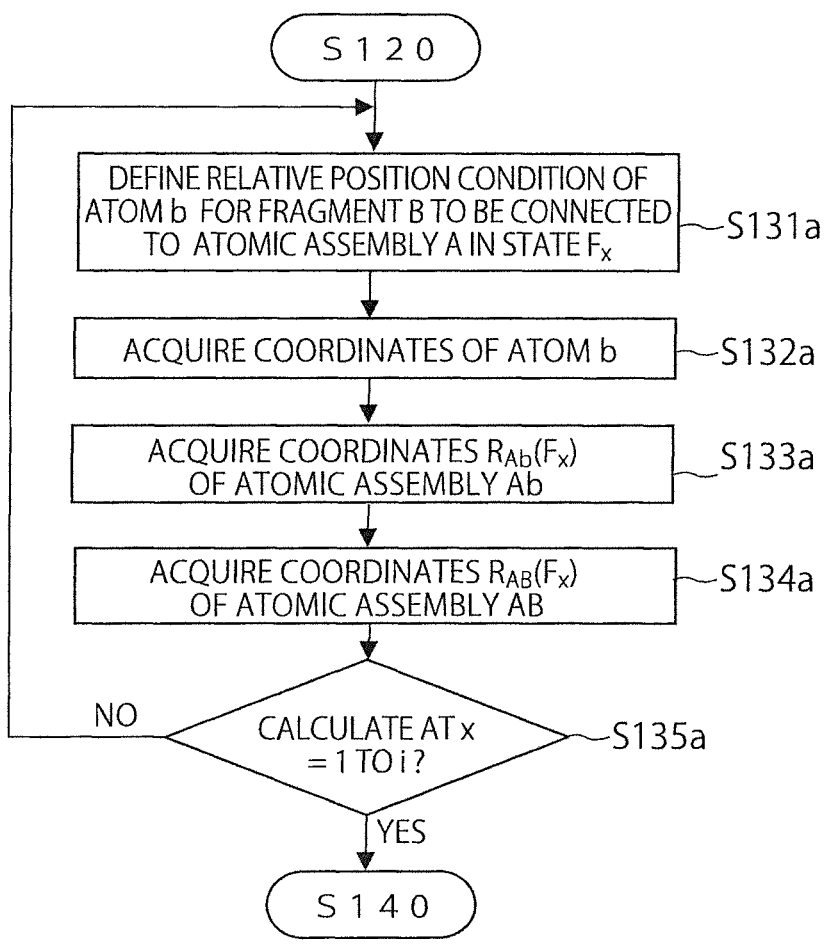
FIG. 4 is a flowchart illustrating an example of a processing procedure in step S130.

FIG. 4 illustrates an example of step S130 performed by the control unit 12. In this example, the control unit 12 performs the following steps after step S120:

step S131a to define a relative position condition (for example, a distance(s) or an angle(s) with respect to one or more atoms constituting structure a) of atom b selected from atoms constituting fragment B with respect to structure a for fragment B to be connected to atomic assembly A in state $F_x$;

step S132a to acquire coordinates of atom b based on the defined relative position condition;

step S133a to acquire coordinates $R_{Ab}(F_x)$ of atomic assembly Ab generated by connection of atom b to atomic assembly A in state $F_x$ based on the acquired coordinates of atom b and coordinates $R_A(F_x)$ of atomic assembly A in state $F_x$; and step S134a to generate coordinates of an atom(s) other than atom b, constituting fragment B by computer simulation, known conformation generation methods, or the like based on coordinates of atom b, and to acquire coordinates $R_{AB}(F_x)$ of atomic assembly AB generated by connection of fragment B to atomic assembly A in state $F_x$. In step S135a, the control unit 12 determines whether steps S131a to S134a have been performed at x=1, 2, ..., i. In a case of "NO", the control unit 12 performs steps S131a to S134a repeatedly. That is, the control unit 12 performs steps S131a to S134a repeatedly at x=1, 2, ..., i until determination of "YES" is obtained in step S135a. Coordinates $R_{AB}(F_1)$ to $R_{AB}(F_i)$ of atomic assembly AB generated by connection of fragment B having a limited relative position with respect to structure a can be thereby acquired for atomic assembly A in each of states $F_1$ to $F_i$.

In step S131a, the control unit 12 may define the first, second, ..., and p th relative position conditions which are different from one another for fragment B to be connected to atomic assembly A in state $F_x$. p is an integer of two or more selected independently from a value of x. Therefore, p may be the same value to each other while x=1, 2, ..., i, or may be a different value from each other while x=1, 2, ..., i.

In step S131a, when the first, second, ..., and p th relative position conditions which are different from one another are defined for fragment B to be connected to atomic assembly A in state $F_x$, the control unit 12 performs steps S132a to S134a repeatedly for each of the first to p th relative position conditions. Coordinates $R_{AB}(F_x,B_1)$, $R_{AB}(F_x,B_2)$, ..., and $R_{AB}(F_x,B_p)$ of atomic assembly AB generated by connection of the fragments $B_1$, $B_2$, ..., and $B_p$ having different relative positions with respect to structure a can be thereby acquired for atomic assembly A in state $F_x$.

Figure 5:
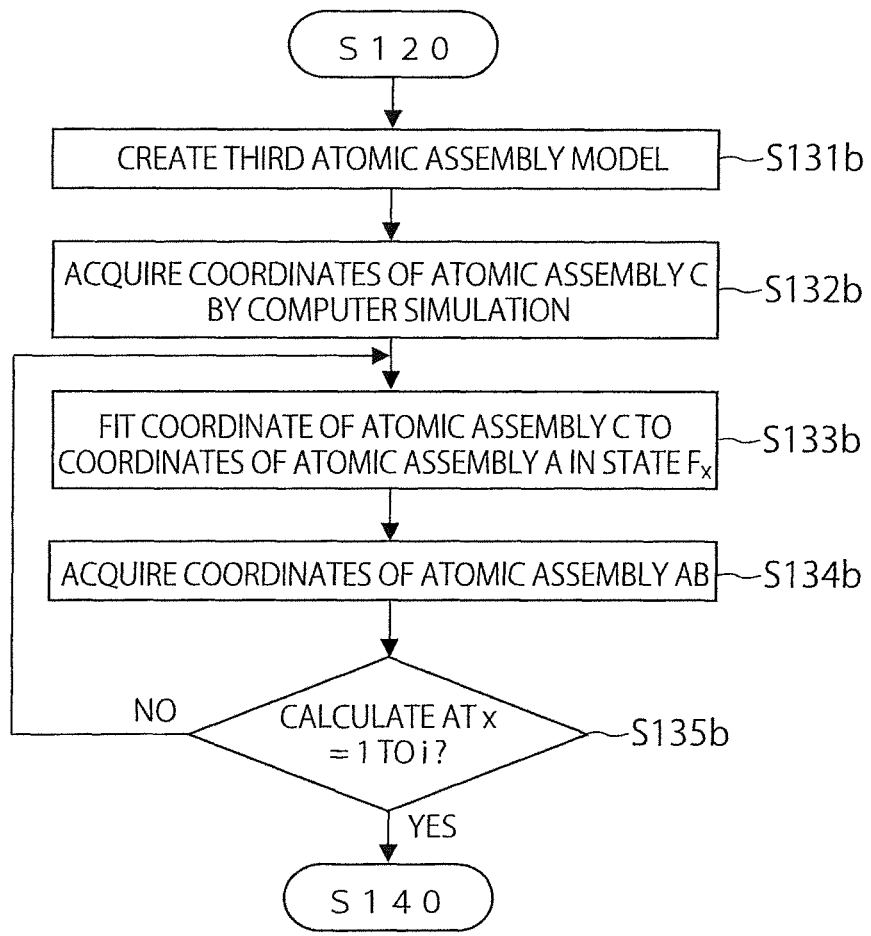
FIG. 5 is a flowchart illustrating another example of a processing procedure in step S130.

FIG. 5 illustrates a preferable example of step S130 performed by the control unit 12. In this example, after step S120, the control unit 12 performs the following steps:

step S131b to create a third atomic assembly model modeling atomic assembly C consisting of structure a and fragment B connected to the structure a or containing structure a and fragment B connected to the structure a; and step S132b to acquire coordinates of atomic assembly C in each of first to k th states $H_1$ to $H_k$ (wherein k is an integer of two or more) by computer simulation with respect to the created third atomic assembly model, and then performs the following processing repeatedly at x=1 to i:

step S133b to select a selected atomic group consisting of one or more atoms selected from atoms constituting structure a (note that not only a case where two or more atoms are selected but also a case where one atom is selected is referred to as a "selected atomic group" for convenience), to rotate and/or translate coordinates of a selected atomic group of atomic assembly C in one or more states selected from states $H_1$ to $H_k$ with respect to coordinates of a selected atomic group of atomic assembly A in state $F_x$, thereby to create coordinates of atomic assembly C having the minimum sum of squares of distances between corresponding atoms between the selected atomic group of atomic assembly A and the selected atomic group of atomic assembly C (to fit coordinates of the selected atomic group of atomic assembly C to coordinates of the selected atomic group of atomic assembly A), and to superimpose atomic assembly C in one or more states selected from states $H_1$ to $H_k$ on atomic assembly A based on the created coordinates of atomic assembly C; and step S134b to acquire coordinates of atomic assembly AB generated by connection of fragment B to atomic assembly A in state $F_x$ based on coordinates of atomic assembly A in state $F_x$ and one or more coordinates of fragment B in atomic assembly C superimposed on atomic assembly A. In step S135b, the control unit 12 determines whether steps S133b and S134b have been performed at x=1, 2, . . . , i. In a case of "NO", the control unit 12 performs steps S133b and S134b repeatedly. That is, the control unit 12 performs steps S133b and S134b repeatedly at x=1, 2, . . . , i until determination of "YES" is obtained in step S135b. Coordinates $R_{AB}(F_1)$ to $R_{AB}(F_i)$ of atomic assembly AB generated by connection of fragment B having a limited relative position with respect to structure a can be thereby acquired for atomic assembly A in each of states $F_1$ to $F_i$.

In step S133b, the control unit 12 may select p sets of coordinates having different relative positions of fragment B to structure a from coordinates of atomic assembly C in states $H_1$ to $H_k$. p is an integer of two or more selected independently from a value of x. Therefore, p may be the same value to each other while x=1, 2, . . . , i, or may be a different value from each other while x=1, 2, . . . , i.

In step S133b, when p sets of coordinates having different relative positions of fragment B to structure a are selected from coordinates of atomic assembly C in states $H_1$ to $H_k$, the control unit 12 performs steps S133b and S134b repeatedly for each of the p sets of coordinates. Coordinates $R_{AB}(F_x,B_1)$, $R_{AB}(F_x,B_2)$, . . . , and $R_{AB}(F_x,B_p)$ of atomic assembly AB generated by connection of the fragments $B_1$, $B_2$, . . . , and $B_p$ having different relative positions with respect to structure a can be thereby acquired for atomic assembly A in state $F_x$.

In step S140, the control unit 12 calculates interaction energy φ between structure a and fragment B connected to the structure a based on the coordinates of atomic assembly AB acquired in step S130, and, in step S150, creates a frequency distribution indicating a frequency in each class of interaction energy φ. In steps S140 and S150, the control unit 12 functions as the first interaction energy φ frequency distribution creation unit 12D.

Hereinafter, steps S160 to S190 are described.

After step S150, the control unit 12 performs processing for interaction energy φ (step S160) and processing for interaction energy ε (steps S170 to S190). At this time, the control unit 12 may perform steps S170 to S190 after performing step S160, may perform step S160 after performing steps S170 to S190, or may perform step S160 and steps S170 to S190 in parallel. In any case, the control unit 12 performs steps S170 to S190 sequentially.

In step S160, the control unit 12 calculates an appearance probability $P_0(φ)$ in each class of interaction energy φ based on the frequency distribution created in step S150. In step S160, the control unit 12 functions as the first interaction energy φ appearance probability calculation unit 12E.

In step S170, the control unit 12 calculates interaction energy ε between a part or the whole of an atomic assembly generated by removing structure aB consisting of structure a and fragment B connected to the structure a from atomic assembly AB, and fragment B based on the coordinates of atomic assembly AB acquired in step S130. In step S180, the control unit 12 creates a frequency distribution indicating a frequency in each class of interaction energy ε in each class of interaction energy φ of the frequency distribution created in step S150. In steps S170 and S180, the control unit 12 functions as the first interaction energy ε frequency distribution creation unit 12F.

In step S170, the control unit 12 calculates interaction energy ε between a part or the whole of an atomic assembly generated by removing structure aB consisting of structure a and fragment B connected to the structure a from atomic assembly AB, and fragment B for each of coordinates $R_{AB}(F_1)$ to $R_{AB}(F_i)$ of atomic assembly AB based on the coordinates of atomic assembly AB acquired in step S130, then extracts interaction energy ε between a part or the whole of an atomic assembly generated by removing structure aB from atomic assembly AB and fragment B in each class of interaction energy φ based on the coordinates of atomic assembly AB acquired in step S130 and the frequency distribution created in step S150, and may create a frequency distribution indicating a frequency in each class of interaction energy ε in each class of interaction energy φ of the frequency distribution created in step S150. Alternatively, the control unit 12 extracts coordinates of atomic assembly AB belonging to each class of interaction energy φ from the coordinates of atomic assembly AB acquired in step S130 based on the frequency distribution created in step S150, then calculates interaction energy ε between a part or the whole of an atomic assembly generated by removing structure aB consisting of structure a and fragment B connected to the structure a from atomic assembly AB, and fragment B in each class of interaction energy φ based on the extracted coordinates of atomic assembly AB, and may create a frequency distribution indicating a frequency in each class of interaction energy ε in each class of interaction energy φ in the frequency distribution created in step S150.

In step S190, the control unit 12 calculates an appearance probability $P_0'(ε;φ)$ in each class of interaction energy ε in each class of interaction energy φ based on the frequency distribution created in step S180. In step S190, the control unit 12 functions as the first interaction energy ε appearance probability calculation unit 12G.

Hereinafter, steps S210 to S240 are described.

The control unit 12 performs steps S210 to S240 sequentially.

In step S210, the control unit 12 creates the second atomic assembly model modeling atomic assembly AB after the change using the data 13D for atomic assembly AB after the change that is stored in the storage unit 13. The control unit 12 causes the storage unit 13 to store the created data for the second atomic assembly model. In step S210, the control unit 12 functions as the second atomic assembly model creation unit 12H.

In step S220, the control unit 12 acquires coordinates of atomic assembly AB in each of first to j th states $G_1$ to $G_j$ (wherein j is an integer of two or more) by computer simulation with respect to the second atomic assembly model using the data for the second atomic assembly model, the data 13E for the second simulation condition, the second simulation program 13F and the like that are stored in the storage unit 13.

In step S220, the control unit 12 functions as the third coordinates acquisition unit 12I.

Figure 6:
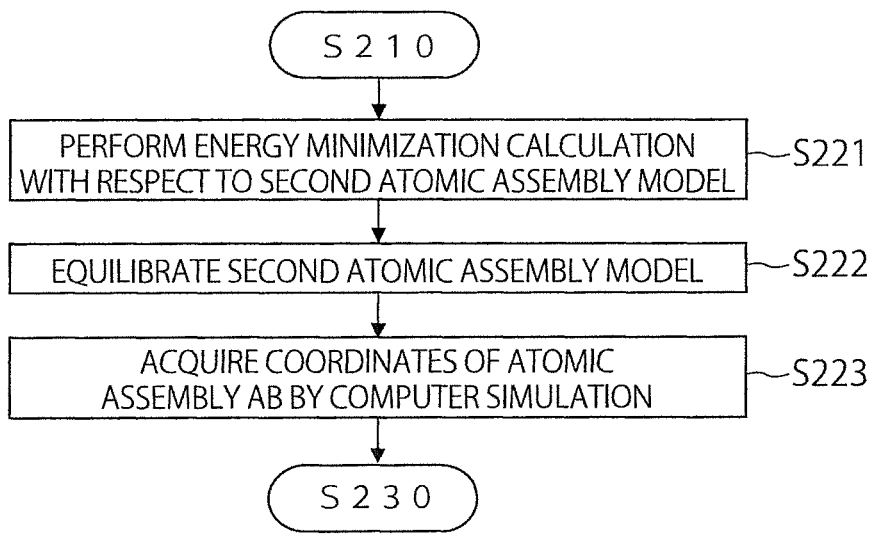
FIG. 6 is a flowchart illustrating an example of a processing procedure in step S220.

FIG. 6 illustrates an example of step S220 performed by the control unit 12 when a molecular dynamics method is used as computer simulation. In this example, after step S210, the control unit 12 performs energy minimization calculation with respect to the second atomic assembly model (step S221), and subsequently equilibrates the second atomic assembly model (step S222) to acquire coordinates of atomic assembly AB in each of states $G_1$ to $G_j$ after the equilibration by computer simulation with respect to the second atomic assembly model after the equilibration. In step S222, for example, when a certain physical quantity in the second atomic assembly model reaches a threshold value or when a certain time passes after start of computer simulation, the control unit 12 determines that the second atomic assembly model has been equilibrated.

In step S230, the control unit 12 calculates interaction energy ϕ between structure a and fragment B connected to the structure a based on the coordinates of atomic assembly AB acquired in step S220, and creates a frequency distribution indicating a frequency in each class of interaction energy ϕ in step S240. In steps S230 and S240, the control unit 12 functions as the second interaction energy ϕ frequency distribution creation unit 12J.

Hereinafter, steps S250 to S280 are described.

After step S240, the control unit 12 performs processing for interaction energy ϕ (step S250) and processing for interaction energy ε (steps S260 to S280). At this time, the control unit 12 may perform steps S260 to S280 after performing step S250, may perform step S250 after performing steps S260 to S280, or may perform step S250 and steps S260 to S280 in parallel. In any case, the control unit 12 performs steps S260 to S280 sequentially.

In step S250, the control unit 12 calculates an appearance probability P(ϕ) in each class of interaction energy ϕ based on the frequency distribution created in step S240. In step S250, the control unit 12 functions as the second interaction energy ϕ appearance probability calculation unit 12K.

In step S260, the control unit 12 calculates interaction energy ε between a part or the whole of an atomic assembly generated by removing structure aB consisting of structure a and fragment B connected to the structure a from atomic assembly AB, and fragment B based on the coordinates of atomic assembly AB acquired in step S220. In step S270, the control unit 12 creates a frequency distribution indicating a frequency in each class of interaction energy ε. In steps S260 and S270, the control unit 12 functions as the second interaction energy ε frequency distribution creation unit 12L.

In step S260, the control unit 12 may calculate interaction energy ε with or without associating interaction energy ε with each class of interaction energy ϕ in the frequency distribution created by step S240. When interaction energy ε is calculated by being associated with each class of interaction energy ϕ, interaction energy ε is calculated for all the classes of interaction energy ϕ included in the frequency distribution (for example, histogram) created in step S240, and the frequency distribution indicating a frequency in each class of interaction energy ε is created for interaction energy ε in each class of interaction energy ϕ.

When the control unit 12 calculates interaction energy ε without associating interaction energy ε with each class of interaction energy ϕ, the control unit 12 calculates interaction energy ε between a part or the whole of an atomic assembly generated by removing structure aB consisting of structure a and fragment B connected to the structure a from atomic assembly AB, and fragment B based on the coordinates of atomic assembly AB acquired in step S220 for each of coordinates $R_{AB}(G_1)$ to $R_{AB}(G_j)$ of atomic assembly AB, and creates a frequency distribution indicating a frequency in each class of interaction energy ε.

When the control unit 12 calculates interaction energy ε by associating interaction energy ε with each class of interaction energy ϕ, the control unit 12 calculates interaction energy ε between a part or the whole of an atomic assembly generated by removing structure aB consisting of structure a and fragment B connected to the structure a from atomic assembly AB, and fragment B based on the coordinates of atomic assembly AB acquired in step S220, and creates a frequency distribution indicating a frequency in each class of interaction energy ε in each class of interaction energy ϕ of the frequency distribution created in step S240.

In an example, the control unit 12 calculates interaction energy ε between a part or the whole of an atomic assembly generated by removing structure aB consisting of structure a and fragment B connected to the structure a from atomic assembly AB, and fragment B for each of coordinates $R_{AB}(G_1)$ to $R_{AB}(G_j)$ of atomic assembly AB based on the coordinates of atomic assembly AB acquired in step S220, then extracts interaction energy ε between a part or the whole of an atomic assembly generated by removing structure aB consisting of structure a and fragment B connected to the structure a from atomic assembly AB, and fragment B in each class of interaction energy ϕ based on the frequency distribution created in step S240, and creates a frequency distribution indicating a frequency in each class of interaction energy ε in each class of interaction energy ϕ in the frequency distribution created in step S240.

In another example, the control unit 12 extracts coordinates of atomic assembly AB belonging to each class of interaction energy ϕ from the coordinates of atomic assembly AB acquired in step S220 based on the frequency distribution created in step S240, then calculates interaction energy ε between a part or the whole of an atomic assembly generated by removing structure aB consisting of structure a and fragment B connected to the structure a from atomic assembly AB, and fragment B in each class of interaction energy ϕ based on the extracted coordinates of atomic assembly AB, and creates a frequency distribution indicating a frequency in each class of interaction energy ε in each class of interaction energy ϕ in the frequency distribution created in step S240.

When the control unit 12 calculates interaction energy ε without associating interaction energy ε with each class of interaction energy ϕ, in steps S260 and S270, the control unit 12 calculates interaction energy ε between a part or the whole of an atomic assembly generated by removing structure aB consisting of structure a and fragment B connected to the structure a from atomic assembly AB, and fragment B based on the coordinates of atomic assembly AB acquired in step S220 for each of coordinates $R_{AB}(G_1)$ to $R_{AB}(G_j)$ of atomic assembly AB, and creates a frequency distribution indicating a frequency in each class of interaction energy ε.

When the control unit 12 calculates interaction energy ε by associating interaction energy ε with each class of interaction energy ϕ, in steps S260 and S270, the control unit 12 calculates interaction energy ε between a part or the whole of an atomic assembly generated by removing structure aB consisting of structure a and fragment B connected to the structure a from atomic assembly AB, and fragment B based on the coordinates of atomic assembly AB acquired in step S220 for each of coordinates $R_{AB}(G_1)$ to $R_{AB}(G_j)$ of atomic assembly AB, then extracts interaction energy ε between a part or the whole of an atomic assembly generated by removing structure aB from atomic assembly AB and fragment B in each class of interaction energy □ based on the frequency distribution created in step S240, and may create a frequency distribution indicating a frequency in each class of interaction energy ε in each class of interaction energy φ of the frequency distribution created in step S240. Alternatively, the control unit 12 extracts coordinates of atomic assembly AB belonging to each class of interaction energy φ from the coordinates of atomic assembly AB acquired in step S220 based on the frequency distribution created in step S240, then calculates interaction energy ε between a part or the whole of an atomic assembly generated by removing structure aB from atomic assembly AB, and fragment B in each class of interaction energy φ based on the extracted coordinates of atomic assembly AB, and may create a frequency distribution indicating a frequency in each class of interaction energy ε in each class of interaction energy φ in the frequency distribution created in step S240.

In step S280, the control unit 12 calculates an appearance probability P'(ε) in each class of interaction energy ε based on the frequency distribution created in step S270. In step S280, the control unit 12 functions as the second interaction energy ε appearance probability calculation unit 12M.

In steps S260 and S270, when the control unit 12 calculates interaction energy ε without associating interaction energy ε with each class of interaction energy φ in the frequency distribution created in step S240, and creates a frequency distribution in each class of interaction energy ε, in step S280, the control unit 12 calculates an appearance probability P'(ε) in each class of interaction energy ε without associating the appearance probability P'(ε) with each class of interaction energy φ based on the frequency distribution created in step S270.

In steps S260 and S270, when the control unit 12 calculates interaction energy ε by associating interaction energy ε with each class of interaction energy φ in the frequency distribution created in step S240, and creates a frequency distribution in each class of interaction energy ε, in step S280, the control unit 12 calculates an appearance probability P'(ε;φ) in each class of interaction energy ε in each class of interaction energy φ based on the frequency distribution created in step S270.

Hereinafter, step S300 is described.

The control unit 12 performs calculation processing for atomic assembly A before the change (steps S110 to S190) and calculation processing for atomic assembly AB after the change (steps S210 to S280), and then performs calculation processing for a free energy change amount ∫Δv(φ)P(φ)dφ (step S300).

In step S300, the control unit 12 calculates a free energy change amount ∫Δv(φ)P(φ)dφ caused by interaction energy ε based on P(φ) calculated in step S250, $P_0'(ε;φ)$ calculated in step S190, and P'(ε) calculated in step S280. In step S300, the control unit 12 functions as the ∫Δv(φ)P(φ)dφ calculation unit 12N.

In an example, the control unit 12 does not calculate Δv(φ), but calculates ∫Δv(φ)P(φ)dφ based on P(φ) calculated in step S250, $P_0'(ε;φ)$ calculated in step S190, and P'(ε) calculated in step S280 by the energy representation method. P'(ε) used here is an appearance probability in each class of interaction energy ε calculated without being associated with each class of interaction energy φ.

In another example, the control unit 12 calculates a free energy change amount Δv(φ) caused by interaction energy ε in each class of interaction energy φ based on $P_0'(ε;φ)$ calculated in step S190 and P'(ε;φ) calculated in step S280, and calculates ∫Δv(φ)P(φ)dφ based on the calculated Δv(φ) and P(φ) calculated in step S250. At this time, the ∫Δv(φ)P(φ)dφ calculation unit 12N preferably calculates a free energy change amount Δv(φ) caused by interaction energy ε in each class of interaction energy φ based on $P_0'(ε;φ)$ calculated in step S190 and P'(ε;φ) calculated in step S280 by the energy representation method.

Hereinafter, step S400 is described.

The control unit 12 performs calculation processing for a free energy change amount ∫Δv(φ)P(φ)dφ (step S300), and then performs calculation processing for ΔG (step S400).

In step S400, the control unit 12 calculates ΔG based on $P_0(φ)$ calculated in step S160, P(φ) calculated in step S250, ∫Δv(φ)P(φ)dφ calculated in step S300, and numerical formula (1):

$$\Delta G = \int \phi P(\phi)d\phi + RT \int P(\phi)\log\left(\frac{P(\phi)}{P_0(\phi)}\right)d\phi + \int \Delta v(\phi)P(\phi)d\phi \quad (1)$$

wherein R represents a gas constant, and T represents an absolute temperature at which the change represented by reaction formula (1) occurs.

A function of the calculation device 1 according to this example can be implemented by using a computer-readable recording medium with a program to cause the control unit 12 to function as the first atomic assembly model creation unit 12A, the first coordinates acquisition unit 12B, the second coordinates acquisition unit 12C, the first interaction energy φ frequency distribution creation unit 12D, the first interaction energy φ appearance probability calculation unit 12E, the first interaction energy ε frequency distribution creation unit 12F, the first interaction energy ε appearance probability calculation unit 12G, the second atomic assembly model creation unit 12H, the third coordinates acquisition unit 12I, the second interaction energy φ frequency distribution creation unit 12J, the second interaction energy φ appearance probability calculation unit 12K, the second interaction energy ε frequency distribution creation unit 12L, the second interaction energy ε appearance probability calculation unit 12M, the ∫Δv(φ)P(φ)dφ calculation unit 12N, and the ΔG calculation unit 12O (that is, a program to cause the control unit 12 to perform steps S110 to S190, steps S210 to S280, step S300, and step S400) recorded thereon, and by installing the program in the computer. Examples of the computer-readable recording medium with a program recorded thereon include ROM, a floppy disk (registered trademark), a hard disk, an optical disk, a magnetooptical disk, CD-ROM, a magnetic tape, and a nonvolatile memory card.

This disclosure includes not only an example to implement a function of the calculation device 1 according to this example by execution of a program by a computer but also an example to implement a function of the calculation device 1 according to this example by association of a program with OS (operating system) running in a computer, another application software or the like. In addition, this disclosure also includes an example to implement a function of the calculation device 1 according to this example by execution of a part or the whole of actual processing by CPU or the like included in a function expansion board of a computer or a function expansion unit connected to the computer based on an instruction of a program after the program is stored in a memory provided in the function expansion board or the function expansion unit.

EXAMPLES

Hereinafter, specific aspects are described based on Examples. However, this disclosure is not limited thereto.

In the Examples, $\Delta\Delta G$ defined by $\Delta G2-\Delta G1$ in the following reaction formulae (2) and (3) was calculated.

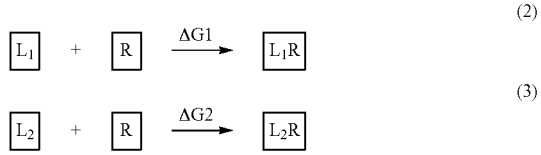
(2)
(3)

In reaction formulae (2) and (3), R represents a protein, □ surrounding R represents presence of water molecules around protein R, $L_1$ represents a ligand bound to protein R, □ surrounding $L_1$ represents presence of water molecules around ligand $L_1$, $L_1R$ represents a complex formed of protein R and ligand $L_1$ bound to the protein R, □ surrounding $L_1R$ represents presence of water molecules around complex $L_1R$, $L_2$ represents a ligand bound to protein R, different from ligand $L_1$, □ surrounding $L_2$ represents presence of water molecules around ligand $L_2$, $L_2R$ represents a complex formed of protein R and ligand $L_2$ bound to the protein R, and □ surrounding $L_2R$ represents presence of water molecules around complex $L_2R$. Note that in the left side of reaction formula (2), $L_1$ and R do not interact with each other, and that in the left side of reaction formula (3), $L_2$ and R do not interact with each other.

$\Delta\Delta G$ can be represented by $\Delta\Delta G=\Delta G4-\Delta G3$ with reference to the following reaction formula (4).

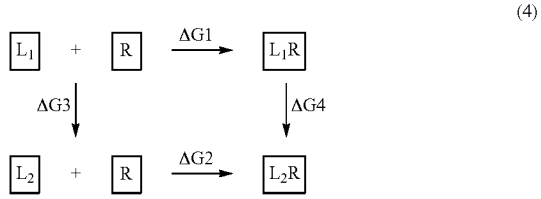
(4)

In the left side of reaction formula (4), protein R does not interact with ligand $L_1$ or $L_2$. Therefore, $\Delta G3$ is a difference in free energy between ligand $L_1$ having water molecules therearound and ligand $L_2$ having water molecules therearound.

$\Delta G4$ can be represented by $\Delta G4=\Delta G4a+\Delta G4b$ with reference to the following reaction formula (5).

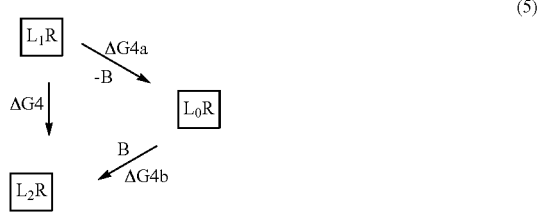
(5)

In reaction formula (5), both a fragment removed in a change of $L_1R \rightarrow L_0R$ and a fragment added in a change of $L_0R \rightarrow L_2R$ are represented by "B" for convenience, but the fragment removed in the change of $L_1R \rightarrow L_0R$ is actually different from the fragment added in the change of $L_0R \rightarrow L_2R$. Details of the fragment removed in the change of $L_1R \rightarrow L_0R$ and the fragment added in the change of $L_0R \rightarrow L_2R$ are described below.

In reaction formula (5), $L_0R$ represents a complex formed of protein R and ligand $L_0$ bound to the protein R, and □ surrounding $L_0R$ represents presence of water molecules around the complex $L_0R$.

$\Delta G3$ can be represented by $\Delta G3=\Delta G3a+\Delta G3b$ with reference to the following reaction formula (6).

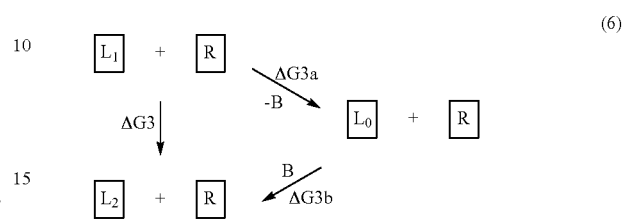
(6)

In reaction formula (6), both a fragment removed in a change of $L_1 \rightarrow L_0$ and a fragment added in a change of $L_0 \rightarrow L_2$ are represented by "B" for convenience, but the fragment removed in the change of $L_1 \rightarrow L_0$ is actually different from the fragment added in the change of $L_0 \rightarrow L_2$. Details of the fragment removed in the change of $L_1 \rightarrow L_0$ and the fragment added in the change of $L_0 \rightarrow L_2$ are described below.

In reaction formula (6), $L_0$ represents a ligand bound to protein R, different from ligand $L_1$ or ligand $L_2$, and □ surrounding $L_0$ represents presence of water molecules around ligand $L_0$. In reaction formula (6), R does not interact with any one of $L_1$, $L_2$, and $L_0$. Therefore, $\Delta G3$ in reaction formula (6) means a difference in free energy between ligand $L_1$ having water molecules therearound and ligand $L_2$ having water molecules therearound.

Example 1

(1) Calculation of $\Delta G4a$

Regarding change represented by the following reaction formula (7):

(7)

atomic assembly constituting complex $L_0R$ and water molecules present around the complex $L_0R$ before the change was referred to as "atomic assembly A", atomic assembly constituting complex $L_1R$ and water molecules present around the complex $L_1R$ after the change was referred to as "atomic assembly AB", and a difference $\Delta G4a'$ between the sum of free energy of atomic assembly A before the change and free energy of fragment B, and free energy of atomic assembly AB after the change was calculated based on numerical formula (1).

$\Delta G4a$ is a free energy change amount regarding change represented by the following reaction formula (8).

(8)

Therefore, a value obtained by multiplying $\Delta G4a'$ calculated based on numerical formula (1) by a minus corresponds to $\Delta G4a$.

As protein R, trypsin that is a kind of serine protease was selected.

As ligand $L_1$, benzamidine that is a trypsin inhibitor was selected. A chemical structure of ligand $L_1$ is as follows.

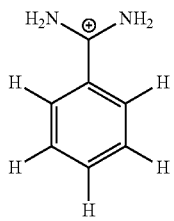

A partial charge of each of atoms constituting ligand $L_1$ is as follows. Four decimal places of the partial charge were rounded off to three decimal places. A partial charge described below is similar. Note that these partial charges were created by the MATCH program described below.

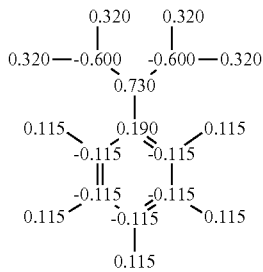

As ligand $L_0$, a molecule obtained by removing fragment B formed of a hydrogen atom connected to the benzene ring carbon atom at a para position of an amidine group and a point charge having a partial charge (−0.115) of the benzene ring carbon atom to which the hydrogen atom was connected from ligand $L_1$ was selected. A chemical structure of ligand $L_0$ is as follows.

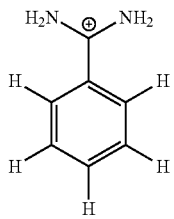

A partial charge of each of atoms constituting ligand $L_0$ is as follows.

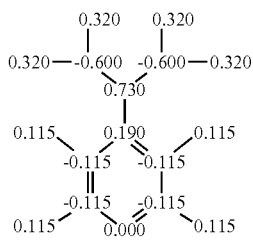

As fragment B, a hydrogen atom and a point charge (partial charge; −0.115) were selected. The hydrogen atom is connected to the benzene ring in ligand $L_1$, and the point charge has a partial charge (−0.115) contained in the carbon atom to which the hydrogen atom was connected in ligand $L_1$. By removing fragment B from ligand $L_1$, a molecule in which the partial charge of the carbon atom to which the hydrogen atom of fragment B was connected among the carbon atoms constituting the benzene ring is zero was obtained as ligand $L_0$. The structure of fragment B is as follows. Here, the point charge having a partial charge (−0.115) is not connected to the hydrogen atom. That is, there is no interaction caused by a bond length, a bond angle, a twist angle or the like. Therefore, hereinafter, a portion between the virtual atom and the hydrogen atom is illustrated by a broken line. In addition, when it was assumed that there was a covalent bond between the atom and the point charge, in a case where there were two or more other atoms between the atoms, an electrostatic interaction between the point charge of fragment B and an atom(s) other than the point charge in fragment B was generated. Also, in the following Examples, description is given similarly.

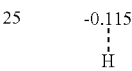

All the atoms constituting ligand $L_0$ were selected from the structures of ligands $L_0$ and $L_1$, and were referred to as "structure a". Therefore, ligand $L_0$ is formed of structure a, and ligand $L_1$ is formed of structure a and fragment B connected to the structure a.

In this Example, $\Delta G4a'$ was calculated by performing steps S110A to S190A, S210A to S280A, S300A, and S400A corresponding to steps S110 to S190, S210 to S280, S300, and S400 illustrated in FIG. 2 using the calculation device illustrated in FIG. 1. In step S120A, steps S121A to S123A corresponding to steps S121 to S123 illustrated in FIG. 3 were performed. In step S130A, steps S131A to S134A corresponding to steps S131b to S134b illustrated in FIG. 5 were performed. In step S220A, steps S221A to S223A corresponding to steps S221 to S223 illustrated in FIG. 6 were performed.

Input of Data for Complex $L_0R$ Contained in Atomic Assembly A Before Change and Complex $L_1R$ Contained in Atomic Assembly AB after Change As a preparatory step before performing steps S110A and S210A, the input unit 11 input data for complex $L_0R$ contained in atomic assembly A before the change and complex $L_1R$ contained in atomic assembly AB after the change (coordinates of each of atoms constituting complex $L_1R$, the kind thereof, a mass thereof, a partial charge thereof, interatomic bond information or the like, and coordinates of each of atoms constituting complex $L_0R$, the kind thereof, a mass thereof, a partial charge thereof, interatomic bond information or the like) in the control unit 12. Here, the kind of an atom means the kind of an element in the periodic table and an atomic type. An atomic type of each atom or a pair of atomic types between atoms is given to correspond to a value of a potential parameter at one to one. The control unit 12 caused the storage unit 13 to store the input data.

Data for complex $L_1R$ contained in atomic assembly AB after the change was obtained by using a three-dimensional structure data file (3PTB_AB) created by removing oxygen atoms attributed to water molecules included in the three-dimensional structure data file (PDB code: 3PTB) downloaded from the three-dimensional structure database protein data bank (PDB) using the integrated computational chemistry system molecular operating environment (MOE) provided by Chemical Computing Group (CCG) Co., Ltd., and then adding hydrogen atoms and coordinates of the hydrogen atoms to the three-dimensional structure data file using the "protonate 3D" function mounted on MOE, and by using the "automatic PSF builder" function mounted on the visualization software visual molecular dynamics (VMD). Note that the three-dimensional structure data (PDB code: 3PTB) included coordinates data for calcium, and the calcium was handled as an ion or a part of the protein. In addition, data for complex $L_0R$ contained in atomic assembly A before the change was created using the "automatic PSF builder" function of VMD based on the three-dimensional structure data file (3PTB_A) created by removing atoms other than the point charge as a virtual atom constituting fragment B from the three-dimensional structure data file (3PTB_AB) using the "builder" function of MOE.

Note that the three-dimensional structure data file (3PTB_AB) includes coordinates data for complex $L_1R$. Data for ligand $L_1$ is selected from the three-dimensional structure data file (3PTB_AB) using MOE, a three-dimensional structure data file (3PTB_$L_1$) for ligand $L_1$ is created, and data for ligand $L_1$ can be obtained by the "automatic PSF builder" function of VMD. Similarly, data for ligand $L_0$ was obtained by creating a three-dimensional structure data file (3PTB_$L_0$) for ligand $L_0$ from the three-dimensional structure data file (3PTB_A) and setting the partial charge of the benzene ring carbon atom connected to the atom (that is, a hydrogen atom) constituting fragment B except for the virtual atom to zero.

Input of Data for Simulation Condition

In a preparatory step before performing steps S110A and S210A described below, the input unit 11 input simulation conditions for energy minimization calculation (the number of calculations of a force applied to each atom, the kind of a potential parameter(s) and a value(s) thereof, a boundary condition, a switching function and a cut-off radius for van der Waals potential and Coulomb potential calculation, a long-distance interaction in Coulomb potential calculation, a condition for a 1-4 interaction and the like) and simulation conditions for molecular dynamics simulation (simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a 1-4 interaction, an output condition such as the number of snapshots and the like) in the control unit 12. The control unit 12 caused the storage unit 13 to store the input data.

CHARMm22 was used as the kind of a potential parameter of each of atoms constituting protein R. Charmm general forcefield (CGenFF) was used as the kind of a potential parameter(s) of each of atoms constituting ligand $L_0$ and the kind of a potential parameter(s) of each of atoms constituting ligand $L_1$. TIP3P was used as the kind of a potential parameter(s) of each of atoms constituting water molecules. Note that a potential parameter(s) of each of atoms constituting ligand $L_0$ and a potential parameter(s) of each of atoms constituting ligand $L_1$ were determined using the MATCH program.

Step S110A: Creation of First Atomic Assembly Model

In step S110A, the control unit 12 read the three-dimensional structure data file (3PTB_A) stored in the storage unit 13 using visualization software VMD, then created a rectangular type basic cell in which 9492 water molecules had been generated around complex $L_0R$ formed of protein R and ligand $L_0$ bound to the protein R using a "solvate" function mounted on the VMD, and created the first atomic assembly model modeling atomic assembly A before the change. The control unit 12 caused the storage unit 13 to store data for the created first atomic assembly model (coordinates of each of atoms constituting atomic assembly A, the kind thereof, a mass thereof, a partial charge thereof, interatomic bond information and the like). Here, the kind of an atom means the kind of an element in the periodic table and an atomic type to designate a potential parameter(s) used in computer simulation.

Step S120A: Acquisition of Coordinates of Atomic Assembly A by Computer Simulation In step S120A, the control unit 12 performed the following steps S121A to S123A.

Step S121A: Energy Minimization Calculation with Respect to First Atomic Assembly Model In step S121A, with respect to the first atomic assembly model, the control unit 12 caused the molecular dynamics simulation program NAMD program to read simulation conditions for energy minimization calculation (the number of calculations of a force applied to each atom, the kind of a potential parameter(s) and a value(s) thereof, a boundary condition, a switching function and a cut-off radius for van der Waals potential and Coulomb potential calculation, a long-distance interaction in Coulomb potential calculation, a condition for a 1-4 interaction and the like), and performed energy minimization calculation using the "minimize" function of NAMD. The control unit 12 caused the storage unit 13 to store data for the first atomic assembly model after the energy minimization calculation (coordinates of each of atoms constituting atomic assembly A, the kind thereof, a mass thereof, a partial charge thereof, an atomic type thereof, interatomic bond information and the like). Here, the kind of an atom means the kind of an element in the periodic table and an atomic type to designate a potential parameter(s) used in computer simulation.

A condition of the energy minimization calculation is as follows.

As the boundary condition, a periodic boundary condition was employed. As for the number of calculations, in the input file of the NAMD program, "minimize" was set to 10000.

As for the switching function and the cut-off radius, in the input file of the NAMD program, a keyword "switching" for the switching function used for van der Waals potential and Coulomb potential calculation was set to 10 angstroms, and a keyword "cutoff" for the cut-off radius was set to 12 angstroms.

As for the long-distance interaction in Coulomb potential calculation, the particle mesh ewald (PME) method in which "PMEGridSpacing" was set to 1.0 angstrom and "PMEInterpOrder" was set to 4 was used.

As for the 1-4 interaction, "exclude" was set to scaled1-4, and "1-4scaling" was set to 1.

Step S122A: Equilibration of First Atomic Assembly Model

In step S122A, the control unit 12 caused the NAMD program to read data for the first atomic assembly model after the energy minimization calculation that is stored in the storage unit 13 (coordinates of each of atoms constituting atomic assembly A, the kind thereof, a mass thereof, a partial charge thereof, interatomic bond information and the like)

and data for a simulation condition (simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a long-distance interaction in Coulomb potential calculation, a condition for a 1-4 interaction, an output condition such as the number of snapshots and the like), performed molecular dynamics simulation with respect to the first atomic assembly model after the energy minimization calculation, and equilibrated the first atomic assembly model. The control unit 12 caused the storage unit 13 to store data for the first atomic assembly model after the equilibration (coordinates of each of atoms constituting atomic assembly A, the kind thereof, a mass thereof, a partial charge thereof, interatomic bond information and the like). Here, the kind of an atom means the kind of an element in the periodic table and an atomic type to designate a potential parameter(s) used in computer simulation.

A condition for molecular dynamics simulation was set as follows.

As the boundary condition, a periodic boundary condition was employed. As for the pressure condition, the pressure was controlled to 1 atm by setting a keyword "langevinPiston" for the pressure control to on and setting "langevinPistonTarget" to 1.01325 in the input file of the NAMD program. As for the temperature condition, the temperature was raised gradually by setting a keyword "langevin" for the temperature control to on and setting "langevinTemp" to a value of 50 Kelvin to 300 Kelvin every 50 Kelvin in the input file of the NAMD program. The each simulation time was 100 picoseconds at 50 Kelvin to 250 Kelvin, and was 1000 picoseconds at 300 Kelvin. A shake method was employed as a numerical solution of an equation of motion, and a time step was set to 2 femtoseconds. As the output condition, coordinates of the first atomic assembly model were output every 200 femtoseconds.

As for the switching function and the cut-off radius, in an input file of the NAMD program, a keyword "switching" for the switching function used for van der Waals potential and Coulomb potential calculation was set to 10 angstroms, and a keyword "cutoff" for the cut-off radius was set to 12 angstroms.

As for the long-distance interaction in Coulomb potential calculation, a particle mesh ewald (PME) method in which "PMEGridSpacing" was set to 1.0 angstrom and "PMEInterpOrder" was set to 4 was used.

As for the 1-4 interaction, "exclude" was set to scaled1-4, and "1-4scaling" was set to 1.

As for the ensemble, an NPT ensemble was constituted by performing the temperature control and the pressure control mounted on the NAMD program.

Step S123A: Acquisition of Coordinates of Atomic Assembly A by Computer Simulation In step S123A, the control unit 12 caused the NAMD program to read data for the first atomic assembly model after the equilibration that is stored in the storage unit 13 (coordinates of each of atoms constituting atomic assembly A, the kind thereof, a mass thereof, a partial charge thereof, interatomic bond information and the like) and data for a simulation condition (simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a 1-4 interaction, an output condition such as the number of snapshots and the like), and performed molecular dynamics simulation with respect to the first atomic assembly model after the equilibration. Here, the kind of an atom means the kind of an element in the periodic table and an atomic type to designate a potential parameter(s) used in computer simulation.

A condition for molecular dynamics simulation was set as follows.

As the boundary condition, a periodic boundary condition was employed. As for the pressure condition, the pressure was controlled to 1 atm by setting a keyword "langevinPiston" for the pressure control to on and setting "langevinPistonTarget" to 1.01325 in an input file of the NAMD program. As for the temperature condition, in an input file of the NAMD program, a keyword "langevin" for the temperature control was set to on, and "langevinTemp" was set to 300 Kelvin. The simulation time was 5000 picoseconds, a shake method was employed as a numerical solution of an equation of motion, and a time step was set to 2 femtoseconds. As for the output condition, coordinates of the first atomic assembly model were output every 50 femtoseconds.

As for the switching function and the cut-off radius, in an input file of the NAMD program, a keyword "switching" for the switching function used for van der Waals potential and Coulomb potential calculation was set to 10 angstroms, and a keyword "cutoff" for the cut-off radius was set to 12 angstroms.

As for the long-distance interaction in Coulomb potential calculation, the particle mesh ewald (PME) method in which "PMEGridSpacing" was set to 1.0 angstrom and "PMEInterpOrder" was set to 4 was used.

As for the 1-4 interaction, "exclude" was set to scaled1-4, and "1-4scaling" was set to 1.

As for the ensemble, an NPT ensemble was constituted by performing the temperature control and the pressure control mounted on the NAMD program.

The control unit 12 acquired coordinates of atomic assembly A every 50 femtoseconds after start of molecular dynamics simulation, that is, after 50 femtoseconds (time $T_1$), after 100 femtoseconds (time $T_2$), . . . , and after 5000 picoseconds (time $T_{100000}$)). Coordinates $R_A(F_i)$ of atomic assembly A in state $F_i$ at time $T_i$ (i=1, 2, . . . , 100000) were thereby acquired. The acquired coordinates of atomic assembly A were 100000 sets of coordinates $R_A(F_1)$, $R_A(F_2)$, . . . , and $R_A(F_{100000})$ in total.

The control unit 12 caused the storage unit 13 to store the coordinates $R_A(F_1)$ to $R_A(F_{100000})$ of atomic assembly A to be arranged along a time axis. That is, the control unit 12 caused the storage unit 13 to store coordinates $R_A(F_i)$ of atomic assembly A in state $F_i$ at time $T_i$ (i=1, 2, . . . , 100000) in association with time $T_i$.

Step S130A: Acquisition of Coordinates of Atomic Assembly AB

In step S130A, the control unit 12 performed steps S131A to S134A.

Step S131A: Creation of Third Atomic Assembly Model

Ligand $L_1$ formed of structure a and fragment B connected to the structure a was selected as atomic assembly C. In atomic assembly C, surrounding of ligand $L_1$ was in vacuum.

In step S131A, the control unit 12 caused the NAMD program to read data for the third atomic assembly model stored in the storage unit 13 (coordinates of each of atoms constituting ligand $L_1$, the kind thereof, a mass thereof, a partial charge thereof, interatomic bond information and the like) and simulation conditions for energy minimization calculation (the number of calculations of a force applied to each atom, the kind of a potential parameter(s) and a value(s) thereof, a boundary condition, a switching function and a cut-off radius for van der Waals potential and Coulomb potential calculation, a long-distance interaction in Coulomb potential calculation, a condition for a 1-4 interaction and the like), and performed energy minimization calculation with respect to the third atomic assembly model. The control unit 12 caused the storage unit 13 to store data for the third atomic assembly model after the energy minimization calculation (coordinates of each of atoms constituting ligand $L_1$, the kind thereof, a mass thereof, a partial charge thereof, interatomic bond information and the like). Here, the kind of an atom means the kind of an element in the periodic table and an atomic type to designate a potential parameter(s) used in computer simulation.

A condition of the energy minimization calculation is as follows.

As for the boundary condition, in step S131A, energy minimization calculation of ligand $L_1$ in vacuum was performed, and therefore the boundary condition and a condition for a long-distance interaction in Coulomb potential calculation was not particularly designated. As the number of calculations of a force applied to each atom, in an input file of the NAMD program, "minimize" was set to 1000.

As for the switching function and the cut-off radius, in the input file of the NAMD program, a keyword "switching" for the switching function used for van der Waals potential and Coulomb potential calculation was set to 10 angstroms, and a keyword "cutoff" for the cut-off radius was set to 12 angstroms.

As for the 1-4 interaction, "exclude" was set to scaled1-4, and "1-4scaling" was set to 1.

Step S132A: Acquisition of Coordinates of Atomic Assembly C by Computer Simulation In step S132A, the control unit 12 performed molecular dynamics simulation with respect to the third atomic assembly model after the energy minimization calculation.

A condition for molecular dynamics simulation was set as follows.

As for the temperature condition, in the input file of the NAMD program, a keyword "langevin" for the temperature control was set to on, and "langevinTemp" was set to 300 Kelvin. The simulation time was 10 nanoseconds, a shake method was employed as a numerical solution of an equation of motion, and a time step was set to 2 femtoseconds. As for the output condition, coordinates of the third atomic assembly model were output every 100 femtoseconds, and 100000 sets of coordinates of atomic assembly C were generated.

As for the switching function and the cut-off radius, in the input file of the NAMD program, a keyword "switching" for the switching function used for van der Waals potential and Coulomb potential calculation was set to 10 angstroms, and a keyword "cutoff" for the cut-off radius was set to 12 angstroms.

As for the 1-4 interaction, "exclude" was set to scaled1-4, and "1-4scaling" was set to 1.

The control unit 12 acquired coordinates of atomic assembly C every 100 femtoseconds after start of molecular dynamics simulation, that is, after 100 femtoseconds (time $T_1$), after 200 femtoseconds (time $T_2$), . . . , and after 10 nanoseconds (time $T_{10000}$). Coordinates $R_C(H_k)$ of atomic assembly C in state $H_k$ corresponding to time $T_k$ (k=1, 2, . . . , 100000) were thereby acquired. The acquired coordinates of atomic assembly C were 100000 sets of coordinates $R_C(H_1)$, $R_C(H_2)$, . . . , and $R_C(H_{100000})$ in total.

The control unit 12 caused the storage unit 13 to store the coordinates $R_C(H_1)$ to $R_C(H_{100000})$ of atomic assembly C to be arranged along a time axis. That is, the control unit 12 caused the storage unit 13 to store coordinates $R_C(H_k)$ of atomic assembly C in state $H_k$ corresponding to time $T_k$ (k=1, 2, . . . , 100000) in association with time $T_k$.

Step S133A: Fitting of Coordinates of Atomic Assembly C with Respect to Coordinates of Atomic Assembly A in State $F_x$ In step S133A, the control unit 12 constituted 100000 sets of a pair Q ($F_1$, $H_1$) formed of coordinates $R_A(F_1)$ of atomic assembly A and coordinates $R_C(H_1)$ of atomic assembly C, a pair Q ($F_2$, $H_2$) formed of coordinates $R_A(F_2)$ of atomic assembly A and coordinates $R_C(H_2)$ of atomic assembly C, . . . , and a pair Q ($F_{100000}$, $H_{100000}$) formed of coordinates $R_A(F_{100000})$ of atomic assembly A and coordinates $R_C(H_{100000})$ of atomic assembly C in total.

In each of the pairs, all the atoms constituting structure a (ligand $L_0$) were selected, and were referred to as a "selected atomic group".

While maintaining relative coordinates (internal coordinates) between each of atoms in coordinates of atomic assembly C for each of pairs Q ($F_1$, $H_1$) to Q($F_{100000}$, $H_{100000}$), the control unit 12 performed fitting of atoms constituting a selected atomic group of atomic assembly C with respect to atoms constituting a selected atomic group of atomic assembly A using numerical formula (7), and superimposed atomic assembly C on atomic assembly A. At this time, Cn set for each atom in numerical formula (7) is as follows.

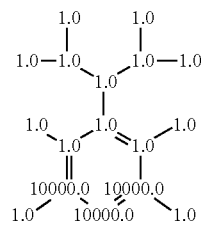

Step S134A: Acquisition of Coordinates of Atomic Assembly AB

In step S134A, the control unit 12 acquired coordinates of fragment B contained in atomic assembly C (however, excluding coordinates of a point charge that is a virtual atom) from coordinates of atomic assembly C superimposed on atomic assembly A for each of pairs Q ($F_1$, $H_1$) to Q($F_{100000}$, $H_{100000}$), added the coordinates to coordinates of atomic assembly A, and acquired coordinates $R_{AB}(F_i)$ of atomic assembly AB. Coordinates $R_{AB}(F_1)$ to $R_{AB}(F_{100000})$ of atomic assembly AB were thereby acquired.

Step S140A: Calculation of Interaction Energy $\phi$

In step S140A, the control unit 12 calculated interaction energy $\phi$ between structure a and fragment B connected to the structure a for each of coordinates $R_{AB}(F_1)$ to $R_{AB}(F_{100000})$ of atomic assembly AB. At this time, the control unit 12 performed the following steps.

The control unit 12 performed processing to extract coordinates $R_{L1}(F_i)$ of each of atoms constituting structure aB (ligand $L_1$) formed of structure a and fragment B connected to the structure a from coordinates $R_{AB}(F_i)$ of atomic assembly AB repeatedly at i=1, 2, . . . , 100000, and acquired coordinates $R_{L1}(F_1)$ to $R_{L1}(F_{100000})$ of atoms constituting structure aB (ligand $L_1$), extracted from coordinates $R_{AB}(F_1)$ to $R_{AB}(F_{100000})$ of atomic assembly AB.

The control unit 12 caused NAMD to read coordinates of each of atoms constituting structure aB (ligand $L_1$), the kind thereof, a mass thereof, a partial charge thereof, the kind of a potential parameter(s) and a value(s) thereof, interatomic bond information and the like, performed processing to calculate energy $E_{L1}(F_i)$ of structure aB (ligand $L_1$) at coordinates $R_{L1}(F_i)$ repeatedly at i=1, 2, . . . , 100000, and calculated energies of structure aB (ligand $L_1$) $E_{L1}(F_1)$ to $E_{L1}(F_{100000})$ for each of coordinates $R_{L1}(F_1)$ to $R_{L1}(F_{100000})$. Here, $E_{L1}(F_i)$ is an energy caused by an interaction between atoms of structure aB (ligand $L_1$), and an internal energy of ligand $L_1$.

The control unit 12 performed processing to extract coordinates $R_a(F_i)$ of each of atoms constituting structure a (ligand $L_0$) from coordinates $R_{AB}(F_i)$ of atomic assembly AB repeatedly at i=1, 2, . . . , 100000, and acquired coordinates of atoms constituting structure a $R_a(F_1)$ to $R_a(F_{100000})$, extracted from coordinates $R_{AB}(F_1)$ to $R_{AB}(F_{100000})$ of atomic assembly AB.

The control unit 12 caused NAMD to read coordinates of each of atoms constituting structure a, the kind thereof, a mass thereof, a partial charge thereof, the kind of a potential parameter(s) and a value(s) thereof, interatomic bond information and the like, performed processing to calculate energy $E_a(F_i)$ of structure a at coordinates $R_a(F_i)$ repeatedly at i=1, 2, . . . , 100000, and calculated energies of structure a $E_a(F_1)$ to $E_a(F_{100000})$ for each of coordinates $R_a(F_1)$ to $R_a(F_{100000})$. Here, $E_a(F_i)$ is an energy caused by an interaction between atoms of structure a, and an internal energy of structure a.

The control unit 12 performed processing to acquire coordinates $R_d(F_i)$ of an atom(s) constituting fragment B except for a virtual atom (a hydrogen atom in a case of the present Example in which structure aB is ligand $L_1$) from coordinates $R_{AB}(F_i)$ of atomic assembly AB repeatedly at i=1, 2, . . . , 100000, and acquired coordinates $R_d(F_1)$ to $R_d(F_{100000})$ of an atom constituting fragment B except for a virtual atom(s), extracted from coordinates $R_{AB}(F_1)$ to $R_{AB}(F_{100000})$ of atomic assembly AB.

The control unit 12 caused NAMD to read coordinates of an atom(s) constituting fragment B except for a virtual atom(s), the kind thereof, a mass thereof, a partial charge thereof, the kind of a potential parameter(s) and a value(s) thereof, interatomic bond information and the like, performed processing to calculate energy $E_d(F_i)$ of an atom(s) constituting fragment B except for a virtual atom(s) and a Coulomb potential $EC_d(F_i)$ thereof for coordinates $R_d(F_i)$ repeatedly at i=1, 2, . . . , 100000, and acquired energies $E_d(F_1)$ to $E_d(F_{100000})$ of an atom(s) constituting fragment B except for a virtual atom(s) and Coulomb potentials thereof $EC_d(F_1)$ to $EC_d(F_{100000})$ for each of coordinates $R_d(F_1)$ to $R_d(F_{100000})$. Here, $E_d(F_i)$ is an energy caused by an interaction between atoms constituting fragment B except for a virtual atom(s), and $EC_d(F_i)$ is an energy caused by an electrostatic interaction between atoms constituting fragment B except for a virtual atom(s). When structure aB was ligand $L_1$, an atom constituting fragment B except for a virtual atom was only one atom of a hydrogen atom, and therefore both of the above values were zero.

The control unit 12 performed processing to calculate an energy $E_e(F_i)$ by subtracting a Coulomb potential $EC_d(F_i)$ from an energy $E_d(F_i)$ of an atom(s) constituting fragment B except for a virtual atom(s) for coordinates $R_d(F_i)$ repeatedly at i=1, 2, . . . , 100000, and calculated energies $E_e(F_1)$ to $E_e(F_{100000})$.

The control unit 12 performed processing to acquire coordinates $R_f(F_i)$ of each of atoms (that is, atoms constituting fragment B including a virtual atom(s)) constituting structure f formed of an atom(s) constituting fragment B except for a virtual atom(s) and an atom(s) having a partial charge(s) of a point charge(s) constituting fragment B among atoms constituting structure aB (ligand $L_1$) (a carbon atom having a bond with a hydrogen atom constituting fragment B among carbon atoms constituting a benzene ring of ligand $L_1$) from coordinates $R_{AB}(F_i)$ of atomic assembly AB repeatedly at i=1, 2, . . . , 100000, and acquired coordinates $R_f(F_1)$ to $R_f(F_{100000})$ of each of atoms constituting structure f, extracted from coordinates $R_{AB}(F_1)$ to $R_{AB}(F_{100000})$ of atomic assembly AB.

The control unit 12 caused NAMD to read coordinates of each of atoms constituting structure f, the kind thereof, a mass thereof, a partial charge thereof, the kind of a potential parameter(s) and a value(s) thereof, interatomic bond information and the like, performed processing to calculate a Coulomb potential $EC_f(F_i)$ for coordinates $R_f(F_i)$ repeatedly at i=1, 2, . . . , 100000, and acquired Coulomb potentials $EC_f(F_1)$ to $EC_f(F_{100000})$. Here, $EC_f(F_i)$ is an energy caused by an electrostatic interaction between atoms constituting structure f. Note that in the present Example in which structure aB was ligand $L_1$, when it was assumed that there was a covalent bond between a hydrogen atom constituting fragment B and a point charge, there was no other atom between the atoms, and therefore $EC_f(F_i)$ was zero.

The control unit 12 performed processing to calculate an energy $E_B(F_i)$ by adding a Coulomb potential $EC_f(F_i)$ to an energy $E_e(F_i)$ repeatedly at i=1, 2, . . . , 100000, and calculated energies $E_B(F_1)$ to $E_B(F_{100000})$.

The control unit 12 performed processing to calculate interaction energy φ between structure a and fragment B repeatedly at i=1, 2, . . . , 100000, based on the following formula:

$$\phi(F_i) = E_{L1}(F_i) - E_a(F_i) - E_B(F_i) \qquad (8).$$

Step S150A: Creation of Frequency Distribution in Each Class of Interaction Energy φ

In step S150A, the control unit 12 created a histogram in which the horizontal axis indicated each class of interaction energy φ and the vertical axis indicated a frequency in each class of interaction energy φ. Note that in the histogram for interaction energy φ, the class interval Δφ was set such that the product of Δφ and the frequency thereof $H_0(\phi)$ in each class interval Δφ was constant, and the number of division of interaction energy φ, that is, the number of class intervals Δφ was set to 100.

Step S160A: Calculation of Appearance Probability $P_0(\phi)$ in Each Class of Interaction Energy φ

In step S160A, the control unit 12 normalized the histogram created in step S150A, and calculated an appearance probability $P_0(\phi)$ in each class of interaction energy φ.

Step S170A: Calculation of Interaction Energy ε

The input unit 11 input various files required for calculation and created by using the gen structure program or the gen_input program as a part of the energy representation method program group such as parameter files, in the control unit 12. The control unit 12 caused the storage unit 13 to store the input files. The energy representation method program group version 0.2.3 was used.

As for a SltInfo file in which parameters for a partial charge of each of atoms constituting structure aB (ligand $L_1$)

and van der Waals of each of atoms constituting structure aB (ligand $L_1$) were input, and that was created by the gen_input program, a parameter(s) for van der Waals of an atom(s) constituting structure a was changed to zero. In addition, a partial charge(s) other than a partial charge(s) of an atom(s) constituting fragment B including a virtual atom(s) was changed to zero.

The control unit 12 performed processing to calculate interaction energy $\varepsilon p$ (i) between fragment B and protein R (in the present Example, one protein) and interaction energy $\varepsilon w$ (i) between fragment B and each water molecule (in the present Example, each of 9492 water molecules) for coordinates $R_{AB}(F_i)$ of atomic assembly AB using the ermod program as a part of the energy representation method program group repeatedly at i=1, 2, . . . , 100000. Here, each $\varepsilon w(i)$ is a set of 9492 interaction energy values between fragment B and each water molecule in total.

Step S180A: Creation of Frequency Distribution in Each Class of Interaction Energy $\varepsilon$ in Each Class of Interaction Energy $\phi$ The control unit 12 selected $\varepsilon p$ and $\varepsilon w$ calculated using coordinates belonging to each class of interaction energy $\phi$ in the histogram created in step S150A from $\varepsilon p(1)$ to $\varepsilon p(100000)$ and $\varepsilon w(1)$ to $\varepsilon w(100000)$ calculated in step S170A, and created histograms $H_0'(\varepsilon p;\phi)$ and $H_0'(\varepsilon w;\phi)$ for the selected $\varepsilon p$ and $\varepsilon w$.

Step S190A: Calculation of Appearance Probability $P_0'(\varepsilon;\phi)$ in Each Class of Interaction Energy $\varepsilon$ in Each Class of Interaction Energy $\phi$ The control unit 12 calculated appearance probabilities $P_0'(\varepsilon p;\phi)$ and $P_0'(\varepsilon w;\phi)$ in each class of the histograms $H_0'(\varepsilon p;\phi)$ and $H_0'(\varepsilon w;\phi)$.

Here, the histograms $H_0'(\varepsilon p;\phi)$ and $H_0'(\varepsilon w;\phi)$ and appearance probabilities $P_0'(\varepsilon p;\phi)$ and $P_0'(\varepsilon w;\phi)$ in steps S180A and S190A were created by the ermod program as a part of the energy representation method program group. Note that as for a parameter of the ermod program, in creation of the histogram $H_0'(\varepsilon p;\phi)$ and the appearance probability $P_0'(\varepsilon p;\phi)$, in a parameter_er file in which parameters of the ermod program were input, setting of ecfbin and ec0bin was changed to 0.05, setting of engdiv was changed to 10, and setting of maxins was changed to 1 from a default condition. In addition, $H_0'(\varepsilon w;\phi)$ and $P_0'(\varepsilon w;\phi)$ were created by changing setting of engdiv to 10 and changing setting of maxins to 1 from a default condition.

The control unit 12 performed steps S180A to S190A in each class of interaction energy $\phi$ in the histogram created in step S150A, and calculated appearance probabilities $P_0'(\varepsilon p;\phi)$ and $P_0'(\varepsilon w;\phi)$ of interaction energy $\varepsilon$ for each class of interaction energy $\phi$.

Step S210A: Creation of Second Atomic Assembly Model
Step S220A: Acquisition of Coordinates of Atomic Assembly AB by Computer Simulation In steps S210A and S220A, the control unit 12 performed steps S210A and S220A in a similar manner to steps S110A and S120A except that atomic assembly A was changed to atomic assembly AB, and acquired coordinates of atomic assembly AB every 50 femtoseconds after start of molecular dynamics simulation in step S223A, that is, after 50 femtoseconds (time $T_1$), after 100 femtoseconds (time $T_2$), . . . , and after 5000 picoseconds (time $T_{100000}$). Coordinates $R_{AB}(G_j)$ of atomic assembly AB in state $G_j$ at time $T_j$ (j=1, 2, . . . , 100000) was thereby acquired. The acquired coordinates of atomic assembly AB were 100000 sets of coordinates $R_{AB}(G_1)$, $R_{AB}(G_2)$, . . . , and $R_{AB}(G_{100000})$ in total.

The control unit 12 caused the storage unit 13 to store coordinates $R_{AB}(G_1)$ to $R_{AB}(G_{100000})$ of atomic assembly AB to be arranged along a time axis. That is, the control unit 12 caused the storage unit 13 to store coordinates $R_{AB}(G_j)$ of atomic assembly AB in state $G_j$ at time $T_j$ (j=1, 2, . . . , 100000) in association with time $T_j$.

Step S230A: Calculation of Interaction Energy $\phi$

In step S230A, the control unit 12 performed step S230A in a similar manner to step S140A, and calculated interaction energy $\phi$ between structure a and fragment B connected to the structure a for each of coordinates $R_{AB}(G_1)$ to $R_{AB}(G_{100000})$ of atomic assembly AB.

Step S240A: Creation of Frequency Distribution in Each Class of Interaction Energy $\phi$ In step S240A, the control unit 12 created a histogram in which the horizontal axis indicated each class of interaction energy $\phi$ and the vertical axis indicated a frequency in each class of interaction energy $\phi$. Each class interval $\Delta\phi$ was set to be the same as each $\Delta\phi$ set in step S150A, and the number of division of interaction energy $\phi$, that is, the number of class intervals $\Delta\phi$ was set to 100.

Step S250A: Calculation of Appearance Probability $P(\phi)$ in Each Class of Interaction Energy $\phi$ In step S250A, the control unit 12 normalized the histogram created in step S240A, and calculated an appearance probability $P(\phi)$ in each class of interaction energy $\phi$.

Step S260A: Calculation of Interaction Energy $\varepsilon$

In step S260A, the control unit 12 performed processing to calculate interaction energy $\varepsilon p$ (i) between fragment B and protein R (in the present Example, one protein) and interaction energy $\varepsilon w$ (i) between fragment B and each water molecule (in the present Example, each of 9492 water molecules) for coordinates $R_{AB}(G_i)$ of atomic assembly AB using the ermod program as a part of the energy representation method program group repeatedly at i=1, 2, . . . , 100000. Here, each $\varepsilon w(i)$ is a set of 9492 interaction energy values between fragment B and each water molecule in total. At this time, various files required for calculation were created, and the SltInfo file was changed in a similar manner to step S170A.

Step S270A: Creation of Frequency Distribution in Each Class of Interaction Energy $\varepsilon$ In step S270A, the control unit 12 created histograms H'($\varepsilon p$) and H'($\varepsilon w$) for $\varepsilon p(1)$ to $\varepsilon p(100000)$ and $\varepsilon w(1)$ to $\varepsilon w(100000)$ calculated in step S260A.

Step S280A: Calculation of Appearance Probability P'($\varepsilon$) in Each Class of Interaction Energy $\varepsilon$ In step S280A, the control unit 12 calculated appearance probabilities P'($\varepsilon p$) and P'($\varepsilon w$) in each class of the histograms H'($\varepsilon p$) and H'($\varepsilon w$).

Here, the histograms H'($\varepsilon p$) and H'($\varepsilon w$) and appearance probabilities P'($\varepsilon p$) and P'($\varepsilon w$) in steps S270A and S280A were created by the ermod program as a part of the energy representation method program group. As for a parameter of the ermod program, in creation of the histogram H'($\varepsilon p$) and P'($\varepsilon p$), in a parameter_er file in which a parameter of the ermod program was input, setting of ecfbin and ec0bin was changed to 0.05 from a default condition. In addition, H'($\varepsilon w$) and P'($\varepsilon w$) were created under a default condition.

The control unit 12 calculated appearance probabilities P'($\varepsilon p$) and P'($\varepsilon w$) in each class of interaction energy $\varepsilon$ through steps S260A to S280A.

Step S300A: Calculation of Free Energy Change Amount $\int\Delta v(\phi)P(\phi)d\phi$ Caused by Interaction Energy $\varepsilon$ In Step S300A, the control unit 12 calculated a free energy change amount $\int\Delta v(\phi)P(\phi)d\phi$ caused by interaction energy $\varepsilon$ through the following steps.

The control unit 12 calculated $\int \Delta vp(\phi)P(\phi)d\phi$ using an appearance probability $P(\phi)$ in each class of interaction energy $\phi$, calculated in step S250A, an appearance probability $P_0'(\varepsilon p:\phi)$ in each class of interaction energy $\varepsilon p$ in each class of interaction energy $\phi$, calculated in step S190A, an appearance probability $P'(\varepsilon p)$ in each class of interaction energy $\varepsilon p$, calculated in step S280A, and a slvfe program as a part of the energy representation method program group.

The control unit 12 calculated $\int \Delta vw(\phi)P(\phi)d\phi$ using an appearance probability $P(\phi)$ in each class of interaction energy $\phi$, calculated in step S250A, an appearance probability $P_0'(\varepsilon w:\phi)$ in each class of interaction energy $\varepsilon w$ in each class of interaction energy $\phi$, calculated in step S190A, an appearance probability $P'(\varepsilon w)$ in each class of interaction energy $\varepsilon w$, calculated in step S280A, and the slvfe program as a part of the energy representation method program group.

The control unit 12 calculated a free energy change amount $\int \Delta v(\phi)P(\phi)d\phi$ caused by interaction energy $\varepsilon$ using self-energy (Eself) of fragment B, obtained as an output of the slvfe program, and $\int \Delta vp(\phi)P(\phi)d\phi$ and $\int \Delta vw(\phi)P(\phi)d\phi$ calculated above according to numerical formula (9). Eself is a value calculated as a correction term in the energy representation method when molecular dynamics simulation on which a periodic boundary condition is imposed is performed.

$$\int \Delta v(\phi)P(\phi)d\phi = \int \Delta vp(\phi)P(\phi)d\phi + \int \Delta vw(\phi)P(\phi)d\phi + E\text{self} \quad (9)$$

Step S400A: Calculation of ΔG4a

In step S400A, the control unit 12 calculated ΔG4a' based on an appearance probability $P_0(\phi)$ in each class of interaction energy $\phi$, calculated in step S160A, an appearance probability $P(\phi)$ in each class of interaction energy $\phi$, calculated in step S250A, $\int \Delta v(\phi)P(\phi)d\phi$ calculated in step S300A, and numerical formula (1):

$$\Delta G = \int \phi P(\phi) d\phi + RT \int P(\phi) \log\left(\frac{P(\phi)}{P_0(\phi)}\right) d\phi + \int \Delta v(\phi) P(\phi) d\phi \quad (1)$$

wherein R represents a gas constant, and T represents an absolute temperature (300 Kelvin) set in molecular dynamics simulation, and multiplied the calculated ΔG4a' by a minus to calculate ΔG4a.

Note that the first term in numerical formula (1) was calculated by simply averaging interaction energy $\phi$.

The calculated ΔG4a was 4.18 (kcal/mol).

(2) Calculation of ΔG3a

Regarding change represented by the following reaction formula (9):

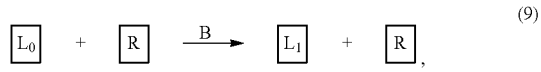

(9)

atomic assembly constituting ligand $L_0$ and water molecules present around the ligand $L_0$ before the change was referred to as "atomic assembly A", atomic assembly constituting ligand $L_1$ and water molecules present around the ligand $L_1$ after the change was referred to as "atomic assembly AB", and a difference ΔG3a' between the sum of free energy of atomic assembly A before the change and free energy of fragment B, and free energy of atomic assembly AB after the change was calculated based on numerical formula (1).

ΔG3a is a free energy change amount regarding change represented by reaction formula (10).

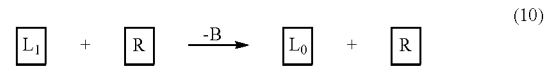

(10)

Therefore, a value obtained by multiplying ΔG3a' calculated based on numerical formula (1) by a minus corresponds to ΔG3a.

In this Example, ΔG3a' was calculated by performing steps S110B to S190B, S210B to S280B, S300B, and S400B corresponding to steps S110 to S190, S210 to S280, S300, and S400 illustrated in FIG. 2 using the calculation device illustrated in FIG. 1. In step S120B, steps S121B to S123B corresponding to steps S121 to S123 illustrated in FIG. 3 were performed. In step S130B, steps S131B to S134B corresponding to steps S131b to S134b illustrated in FIG. 5 were performed. In step S220B, steps S221B to S223B corresponding to steps S221 to S223 illustrated in FIG. 6 were performed.

Input of Data for Ligand $L_0$ Contained in Atomic Assembly A Before Change and Ligand $L_1$ Contained in Atomic Assembly AB after Change In a preparatory step before performing steps S110B and S210B, the input unit 11 input data for ligand $L_0$ contained in atomic assembly A before the change and ligand $L_1$ contained in atomic assembly AB after the change in the control unit 12. The control unit 12 caused the storage unit 13 to store the input data. The input data was obtained by extracting data for ligand $L_0$ and ligand $L_1$ from data for complexes $L_0R$ and $L_1R$ used in calculation of ΔG4a, and coordinates data thereof exists in the three-dimensional structure files 3PTB_$L_0$ and 3PTB_$L_1$, respectively.

Input of Data for Simulation Condition

In a preparatory step before performing steps S110B and S210B, the input unit 11 input data for a simulation condition in the control unit 12. The control unit 12 caused the storage unit 13 to store the input data. The input data was similar to that used in calculation of ΔG4a except for data for protein R.

Step S110B: Creation of First Atomic Assembly Model

In Step S110B, the control unit 12 read the PDB file (3PTB_$L_0$) stored in the storage unit 13 using visualization software VMD, then generated 815 water molecules with gravity coordinates of atoms constituting ligand $L_0$ as an origin using the "solvate" function mounted on the VMD, created a rectangular type basic cell, and created the first atomic assembly model modeling atomic assembly A before the change. Note that as for potential parameters of each atom, CGenFF was used for each of atoms constituting ligand $L_0$ and ligand $L_1$, and TIP3P was used for each of atoms constituting water molecules. The potential parameters of each of atoms constituting ligand $L_0$ and ligand $L_1$ was determined using the MATCH program.

Step S120B: acquisition of atom of atomic assembly A by computer simulation

Step S130B: acquisition of coordinates of atomic assembly AB

Step S140B: calculation of interaction energy $\phi$

Step S150B: creation of frequency distribution in each class of interaction energy $\phi$ Step S160B: calculation of appearance probability $P_0(\phi)$ in each class of interaction energy $\phi$
Step S170B: calculation of interaction energy $\varepsilon$
Step S180B: creation of frequency distribution in each class of interaction energy $\varepsilon$ in each class of interaction energy $\phi$
Step S190B: calculation of appearance probability $P_0'(\varepsilon;\phi)$ in each class of interaction energy $\varepsilon$ in each class of interaction energy $\phi$ The control unit 12 performed steps S120B to S190B in a similar manner to steps S120A to S190A.

A condition for molecular dynamics simulation was similar to step S120A except that equilibration by gradual temperature rising was not performed, equilibration simulation whose temperature was set to 300 K and simulation time was set to 100 picoseconds was performed after energy minimization, and coordinates of atomic assembly A was output in a time step of 10 femtoseconds by setting simulation time after equilibration to 1000 picoseconds.

Step S210B: creation of second atomic assembly model
Step S220B: acquisition of coordinates of atomic assembly AB by computer simulation
Step S230B: calculation of interaction energy $\phi$
Step S240B: creation of frequency distribution in each class of interaction energy $\phi$
Step S250B: calculation of appearance probability $P(\phi)$ in each class of interaction energy $\phi$
Step S260B: calculation of interaction energy $\varepsilon$
Step S270B: creation of frequency distribution in each class of interaction energy $\varepsilon$
Step S280B: calculation of appearance probability $P'(\varepsilon)$ in each class of interaction energy $\varepsilon$ The control unit 12 performed steps S210B to S280B in a similar manner to steps S210A to S280A.

A condition for molecular dynamics simulation was similar to step S220A except that equilibration by gradual temperature rising was not performed, equilibration simulation whose temperature was set to 300 K and simulation time was set to 100 picoseconds was performed after energy minimization, and coordinates of atomic assembly AB was output in a time step of 10 femtoseconds by setting simulation time after equilibration to 1000 picoseconds.

Step S300B: Calculation of Free Energy Change Amount $\int \Delta v(\phi) P(\phi) d\phi$ Caused by Interaction Energy $\varepsilon$
Step S400B: Calculation of $\Delta G3a$ The control unit 12 performed steps S300B to S400B in a similar manner to steps S300A to S400A.

The calculated $\Delta G3a$ was 1.59 (kcal/mol).

(3) Calculation of $\Delta G4b$

Regarding change represented by reaction formula (11):

(11)

atomic assembly constituting complex $L_0R$ and water molecules present around the complex $L_0R$ before the change was referred to as "atomic assembly A", atomic assembly constituting complex $L_2R$ and water molecules present around the complex $L_2R$ after the change was referred to as "atomic assembly AB", and a difference $\Delta G4b$ between the sum of free energy of atomic assembly A before the change and free energy of fragment B, and free energy of atomic assembly AB after the change was calculated.

In this Example, $\Delta G4b$ was calculated by performing steps S110C to S190C, S210C to S280C, S300C, and S400C corresponding to steps S110 to S190, S210 to S280, S300, and S400 illustrated in FIG. 2 using the calculation device illustrated in FIG. 1. In step S120C, steps S121C to S123C corresponding to steps S121 to S123 illustrated in FIG. 3 were performed. In step S130C, steps S131C to S134C corresponding to steps S131b to S134b illustrated in FIG. 5 were performed. In step S220C, steps S221C to S223C corresponding to steps S221 to S223 illustrated in FIG. 6 were performed.

A chemical structure of ligand $L_2$ is as follows.

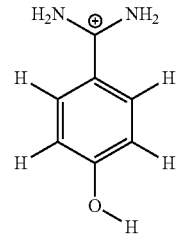

A partial charge of each of atoms constituting ligand $L_2$ is as follows.

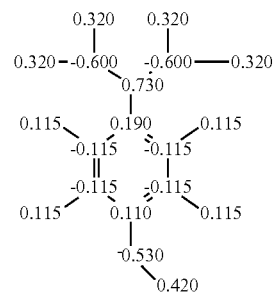

The structure of fragment B is as follows.

Steps S110C to S190C, S210C to S280C, S300C, and S400C were performed in a similar manner to steps S110A to S190A, S210A to S280A, S300A, and S400A in calculation of $\Delta G4a$ except that ligand $L_1$ was changed to ligand $L_2$ and fragment B was changed. The calculated $\Delta G4b$ was $-17.84$ (kcal/mol).

(4) Calculation of $\Delta G3b$

Regarding change represented by reaction formula (12):

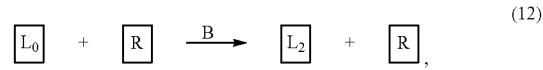
(12)

atomic assembly constituting ligand $L_0$ and water molecules present around the ligand $L_0$ before the change was referred to as "atomic assembly A", atomic assembly constituting ligand $L_2$ and water molecules present around the ligand $L_2$ after the change was referred to as "atomic assembly AB", and a difference $\Delta G3b$ between the sum of free energy of atomic assembly A before the change and free energy of fragment B, and free energy of atomic assembly AB after the change was calculated.

In this Example, ΔG3b was calculated by performing steps S110D to S190D, S210D to S280D, S300D, and S400D corresponding to steps S110 to S190, S210 to S280, S300, and S400 illustrated in FIG. 2 using the calculation device illustrated in FIG. 1. In step S120D, steps S121D to S123D corresponding to steps S121 to S123 illustrated in FIG. 3 were performed. In step S130D, steps S131D to S134D corresponding to steps S131b to S134b illustrated in FIG. 5 were performed. In step S220D, steps S221D to S223D corresponding to steps S221 to S223 illustrated in FIG. 6 were performed.

Steps S110D to S190D, S210D to S280D, S300D, and S400D were performed in a similar manner to steps S110B to S190B, S210B to S280B, S300B, and S400B in calculation of ΔG3a except that ligand $L_1$ was changed to ligand $L_2$ and fragment B was changed. The calculated ΔG3b was −14.91 (kcal/mol).

(5) Calculation of ΔΔG

ΔΔG calculated by

ΔΔ$G$=Δ$G$4−Δ$G$3,

Δ$G$4=Δ$G$4$a$+Δ$G$4$b$, and

Δ$G$3=Δ$G$3$a$+Δ$G$3$b$ was −0.34 (kcal/mol).

ΔΔG determined by an experiment, described in published literatures (Journal of Chemical Theory and Computation, 8, 3686-3695 (2012) and Journal of the American Chemical Society, 99, 2331-2336 (1977)) is −0.10 (kcal/mol). ΔΔG determined by a calculation method had a difference of 1 kcal/mol or less from the ΔΔG determined by an experiment, and was in good agreement therewith.

Example 2

ΔΔG was calculated in a similar manner to Example 1 using ligand $L_3$ in place of ligand $L_2$.

A chemical structure of ligand $L_3$ is as follows.

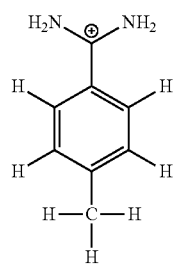

A partial charge of each of atoms constituting ligand $L_3$ is as follows.

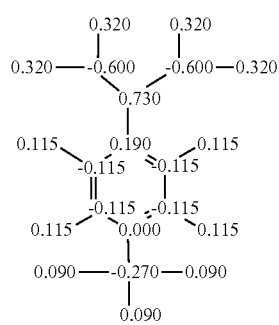

The structure of fragment B is as follows.

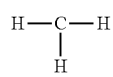

Here, as described below, ΔΔG was calculated in a similar manner to Example 1 by handling a point charge (partial charge; 0.000) as an atom constituting fragment B for convenience.

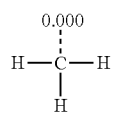

As ΔG4a and ΔG3a, the same values as those in Example 1 were used.
The calculated ΔG4b was −8.12 (kcal/mol).
The calculated ΔG3b was −5.45 (kcal/mol).
The calculated ΔΔG was −0.08 (kcal/mol).

ΔΔG determined by an experiment, described in published literatures (Journal of Chemical Theory and Computation, 8, 3686-3695 (2012) and Journal of the American Chemical Society, 99, 2331-2336 (1977)) is 0.27 (kcal/mol). ΔΔG determined by a calculation method had a difference of 1 kcal/mol or less from the ΔΔG determined by an experiment, and was in good agreement therewith.

Example 3

ΔΔG was calculated in a similar manner to Example 1 using ligand $L_4$ in place of ligand $L_2$.
A chemical structure of ligand $L_4$ is as follows.

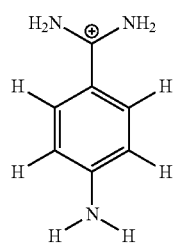

A partial charge of each of atoms constituting ligand $L_4$ is as follows.

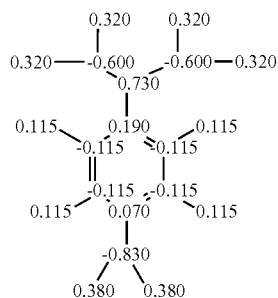

The structure of fragment B is as follows.

As ΔG4a and ΔG3a, the same values as those in Example 1 were used.

The calculated ΔG4b was −23.00 (kcal/mol).

The calculated ΔG3b was −19.88 (kcal/mol).

The calculated ΔΔG was −0.53 (kcal/mol).

ΔΔG determined by an experiment, described in published literatures (Journal of Chemical Theory and Computation, 8, 3686-3695 (2012) and Journal of the American Chemical Society, 99, 2331-2336 (1977)) is −0.40 (kcal/mol). ΔΔG determined by a calculation method had a difference of 1 kcal/mol or less from the ΔΔG determined by an experiment, and was in good agreement therewith.

Example 4

ΔΔG was calculated in a similar manner to Example 1 using ligand $L_5$ in place of ligand $L_2$.

A chemical structure of ligand $L_5$ is as follows.

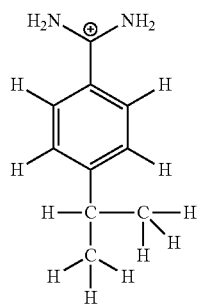 [SMILES: CC(C)c1ccc([C+](N)N)cc1]

A partial charge of each of atoms constituting ligand $L_5$ is as follows.

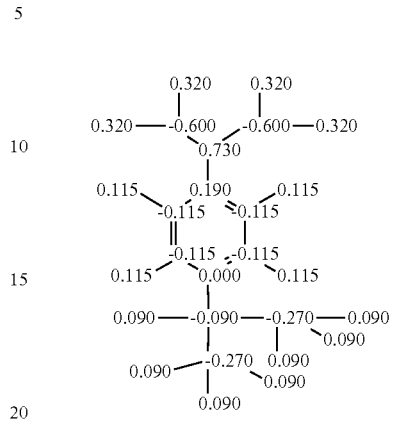

The structure of fragment B is as follows.

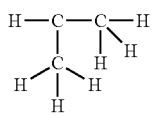

Here, as described below, ΔΔG was calculated in a similar manner to Example 1 by handling a point charge (partial charge; 0.000) as an atom constituting fragment B for convenience.

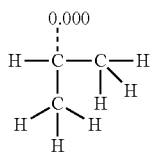

As ΔG4a and ΔG3a, the same values as those in Example 1 were used.

The calculated ΔG4b was 1.78 (kcal/mol).

The calculated ΔG3b was 3.55 (kcal/mol).

The calculated ΔΔG was 0.82 (kcal/mol).

ΔΔG determined by an experiment, described in a published literature (Journal of the American Chemical Society, 125, 10570-10579 (2003)) is 0.93 (kcal/mol). ΔΔG determined by a calculation method had a difference of 1 kcal/mol or less from the ΔΔG determined by an experiment, and was in good agreement therewith.

Example 5

ΔΔG was calculated in a similar manner to Example 1 using ligand $L_6$ in place of ligand $L_2$.

A chemical structure of ligand $L_6$ is as follows.

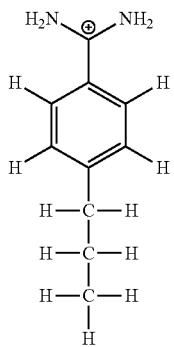 [SMILES: CCCc1ccc([C+](N)N)cc1]

A partial charge of each of atoms constituting ligand $L_6$ is as follows.

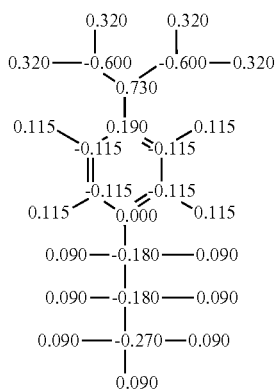

The structure of fragment B is as follows.

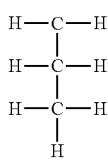

Here, as described below, ΔΔG was calculated in a similar manner to Example 1 by handling a point charge (partial charge; 0.000) as an atom constituting fragment B for convenience.

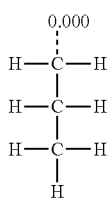

As ΔG4a and ΔG3a, the same values as those in Example 1 were used.

The calculated ΔG4b was −3.79 (kcal/mol).
The calculated ΔG3b was −0.95 (kcal/mol).
The calculated ΔΔG was −0.25 (kcal/mol).

ΔΔG determined by an experiment, described in a published literature (Journal of the American Chemical Society, 125, 10570-10579 (2003)) is 0.25 (kcal/mol). ΔΔG determined by a calculation method had a difference of 1 kcal/mol or less from the ΔΔG determined by an experiment, and was in good agreement therewith.

The invention claimed is:

1. A calculation device comprising a control unit that predicts a difference ΔG between free energy of first molecules, and free energy of second molecules, based on the formula: $\Delta G = (-\Delta G_1) + \Delta G_2$, by calculating, with respect to change represented by reaction formula (1-1):

$$A + B_1 \rightarrow AB_1 \quad (1\text{-}1)$$

wherein A represents an atomic assembly consisting of structure a or comprising structure a, $B_1$ represents a fragment consisting of one or more atoms, and $AB_1$ represents an atomic assembly constituting the first molecules and consisting of atomic assembly A and fragment $B_1$ connected to structure a of the atomic assembly A, a difference $\Delta G_1$ between a sum of free energy of atomic assembly A before the change and free energy of fragment $B_1$, and free energy of atomic assembly $AB_1$ after the change, and with respect to change represented by reaction formula (1-2):

$$A + B_2 \rightarrow AB_2 \quad (1\text{-}2)$$

wherein A is defined as above, $B_2$ represents a fragment consisting of one or more atoms and differing from fragment $B_1$, and $AB_2$ represents an atomic assembly constituting the second molecules and consisting of atomic assembly A and fragment $B_2$ connected to structure a of the atomic assembly A, a difference $\Delta G_2$ between a sum of free energy of atomic assembly A before the change and free energy of fragment $B_2$, and free energy of atomic assembly $AB_2$ after the change, wherein the first molecules comprise a ligand(s), a protein(s) to which the ligand(s) may be bound, and a solvent molecule(s), wherein the second molecules comprise a ligand(s), a protein(s) to which the ligand(s) may be bound, and a solvent molecule(s), and wherein the control unit comprises:

a first atomic assembly model creation unit that creates a first atomic assembly model modeling atomic assembly A before the change;

a first coordinates acquisition unit that causes molecular dynamics simulation program to read as data for the first atomic assembly model created by the first atomic assembly model creation unit, coordinates of each of atoms constituting atomic assembly A, the kind thereof, a mass thereof, a partial charge thereof, and interatomic bond information, and as data for a simulation condition, simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a condition for a 1-4 interaction, and an output condition including the number of snapshots, performs molecular dynamics simulation with respect to the first atomic assembly model created by the first atomic assembly model creation unit, and acquires coordinates of atomic assembly A in each of first to i th states $F_1$ to $F_i$ (wherein i is an integer of two or more) by a snapshot output as a result of molecular dynamics simulation with respect to the first atomic assembly model created by the first atomic assembly model creation unit, wherein the snapshot in each of states $F_1$ to $F_i$ includes coordinates of all the atoms constituting atomic assembly in each of states $F_1$ to $F_i$;

a second coordinates acquisition unit that acquires coordinates of atomic assembly $AB_1$ or $AB_2$ generated by connection of fragment $B_1$ or $B_2$ to atomic assembly A in each of states $F_1$ to $F_i$ based on the coordinates of atomic assembly A acquired by the first coordinates acquisition unit, wherein the coordinates of atomic assembly $AB_1$ or $AB_2$ acquired by the second coordinates acquisition unit contain coordinates of all the atoms constituting atomic assembly $AB_1$ or $AB_2$;

a first interaction energy $\phi$ frequency distribution creation unit that calculates interaction energy $\phi$ between structure a and fragment $B_1$ or $B_2$ connected to the structure a based on the coordinates of atomic assembly $AB_1$ or $AB_2$ acquired by the second coordinates acquisition unit, and creating a frequency distribution indicating a frequency in each class of interaction energy $\phi$;

a first interaction energy $\phi$ appearance probability calculation unit that calculates an appearance probability $P_0(\phi)$ in each class of interaction energy $\phi$ based on the frequency distribution created by the first interaction energy $\phi$ frequency distribution creation unit;

a first interaction energy $\varepsilon$ frequency distribution creation unit that calculates interaction energy $\varepsilon$ between a part or the whole of an atomic assembly generated by removing structure $aB_1$ or $aB_2$ consisting of structure a and fragment $B_1$ or $B_2$ connected to the structure a from atomic assembly $AB_1$ or $AB_2$, and fragment $B_1$ or $B_2$ based on the coordinates of atomic assembly $AB_1$ or $AB_2$ acquired by the second coordinates acquisition unit, and creating a frequency distribution indicating a frequency in each class of interaction energy $\varepsilon$ in each class of interaction energy $\phi$ in the frequency distribution created by the first interaction energy $\phi$ frequency distribution creation unit;

a first interaction energy $\varepsilon$ appearance probability calculation unit that calculates an appearance probability $P_0'(\varepsilon;\phi)$ in each class of interaction energy $\varepsilon$ in each class of interaction energy $\phi$ based on the frequency distribution created by the first interaction energy $\varepsilon$ frequency distribution creation unit;

a second atomic assembly model creation unit that creates a second atomic assembly model modeling atomic assembly $AB_1$ or $AB_2$ after the change;

a third coordinates acquisition unit that causes molecular dynamics simulation program to read as data for the second atomic assembly model created by the second atomic assembly model creation unit, coordinates of each of atoms constituting atomic assembly $AB_1$ or $AB_2$, the kind thereof, a mass thereof, a partial charge thereof, and interatomic bond information, and as data for a simulation condition, simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a condition for a 1-4 interaction, and an output condition including the number of snapshots, performs molecular dynamics simulation with respect to the second atomic assembly model created by the second atomic assembly model creation unit, and acquires coordinates of atomic assembly $AB_1$ or $AB_2$ in each of first to j th states $G_1$ to $G_j$ (wherein j is an integer of two or more) by a snapshot output as a result of molecular dynamics simulation with respect to the second atomic assembly model created by the second atomic assembly model creation unit, wherein the snapshot in each of states $G_1$ to $G_j$ includes coordinates of all the atoms constituting atomic assembly $AB_1$ or $AB_2$ in each of states $G_1$ to $G_j$;

a second interaction energy $\phi$ frequency distribution creation unit that calculates interaction energy $\phi$ between structure a and fragment $B_1$ or $B_2$ connected to the structure a based on the coordinates of atomic assembly $AB_1$ or $AB_2$ acquired by the third coordinates acquisition unit, and creating a frequency distribution indicating a frequency in each class of interaction energy $\phi$;

a second interaction energy $\phi$ appearance probability calculation unit that calculates an appearance probability $P(\phi)$ in each class of interaction energy $\phi$ based on the frequency distribution created by the second interaction energy $\phi$ frequency distribution creation unit;

a second interaction energy $\varepsilon$ frequency distribution creation unit that calculates interaction energy $\varepsilon$ between a part or the whole of an atomic assembly generated by removing structure $aB_1$ or $aB_2$ consisting of structure a and fragment $B_1$ or $B_2$ connected to the structure a from atomic assembly $AB_1$ or $AB_2$, and fragment $B_1$ or $B_2$ based on the coordinates of atomic assembly $AB_1$ or $AB_2$ acquired by the third coordinates acquisition unit, and creating a frequency distribution indicating a frequency in each class of interaction energy $\varepsilon$;

a second interaction energy $\varepsilon$ appearance probability calculation unit that calculates an appearance probability $P'(\varepsilon)$ in each class of interaction energy $\varepsilon$ based on the frequency distribution created by the second interaction energy $\varepsilon$ frequency distribution creation unit;

a $\int \Delta v(\phi) P(\phi) d\phi$ calculation unit that calculates a free energy change amount $\int \Delta v(\phi) P(\phi) d\phi$, wherein $\Delta v(\phi)$ represents a free energy change amount caused by interaction energy $\varepsilon$ in each class of interaction energy $\phi$, caused by interaction energy $\varepsilon$ based on $P(\phi)$ calculated by the second interaction energy $\phi$ appearance probability calculation unit, $P_0'(\varepsilon;\phi)$ calculated by the first interaction energy $\varepsilon$ appearance probability calculation unit, and $P'(\varepsilon)$ calculated by the second interaction energy $\varepsilon$ appearance probability calculation unit; and a $\Delta G_1$ or $\Delta G_2$ calculation unit that calculates $\Delta G_1$ or $\Delta G_2$ based on $P_0(\phi)$ calculated by the first interaction energy $\phi$ appearance probability calculation unit, $P(\phi)$ calculated by the second interaction energy $\phi$ appearance probability calculation unit, $\int \Delta v(\phi) P(\phi) d\phi$ calculated by the $\int \Delta v(\phi) P(\phi) d\phi$ calculation unit, and numerical formula (1):

$$\Delta G = \int \phi P(\phi)d\phi + RT\int P(\phi)\log\left(\frac{P(\phi)}{P_0(\phi)}\right)d\phi + \int \Delta v(\phi)P(\phi)d\phi \quad (1)$$

wherein R represents a gas constant, and T represents an absolute temperature at which the change represented by reaction formula (1) occurs.

2. The calculation device according to claim 1, wherein the second coordinates acquisition unit creates a third atomic assembly model modeling atomic assembly C consisting of structure a and fragment $B_1$ or $B_2$ connected to the structure a or comprising structure a and fragment $B_1$ or $B_2$ connected to the structure a, acquires coordinates of atomic assembly C in each of first to k th states $H_1$ to $H_k$ (wherein k is an integer of two or more) by molecular dynamics simulation with respect to the created third atomic assembly model, and selects a selected atomic group consisting of one or more atoms selected from atoms constituting structure a, rotates and/or translates coordinates of a selected atomic group of atomic assembly C in one or more states selected from states $H_1$ to $H_k$ with respect to coordinates of a selected atomic group of atomic assembly A in each of states $F_1$ to $F_i$, thereby creates coordinates of atomic assembly C having the minimum sum of squares of distances between corresponding atoms between the selected atomic group of atomic assembly A and the selected atomic group of atomic assembly C, superimposes atomic assembly C in one or more states selected from states $H_1$ to $H_k$ on atomic assembly A based on the created coordinates of atomic assembly C, and acquires one or more coordinates of atomic assembly $AB_1$ or $AB_2$ generated by connection of fragment $B_1$ or $B_2$ to atomic assembly A based on coordinates of atomic assembly A and one or more coordinates of fragment $B_1$ or $B_2$ of atomic assembly C superimposed on atomic assembly A.

3. The calculation device according to claim 1, wherein the $\int\Delta v(\phi)P(\phi)d\phi$ calculation unit calculates a free energy change amount $\int\Delta v(\phi)P(\phi)d\phi$ caused by interaction energy $\varepsilon$ based on $P(\phi)$ calculated by the second interaction energy $\phi$ appearance probability calculation unit, $P_0'(\varepsilon;\phi)$ calculated by the first interaction energy $\varepsilon$ appearance probability calculation unit, and $P'(\varepsilon)$ calculated by the second interaction energy $\varepsilon$ appearance probability calculation unit by the energy representation method.

4. The calculation device according to claim 3, wherein fragment $B_1$ or $B_2$ is constituted of an atom(s) containing a point charge(s) as a virtual atom(s), and the second coordinates acquisition unit adds the point charge(s) of fragment $B_1$ or $B_2$ to a charge parameter(s) of an atom(s) constituting structure a of atomic assembly A.

5. The calculation device according to claim 1, wherein fragment $B_1$ or $B_2$ is constituted of an atom(s) containing a point charge(s) as a virtual atom(s), and the second coordinates acquisition unit adds the point charge(s) of fragment $B_1$ or $B_2$ to a charge parameter(s) of an atom(s) constituting structure a of atomic assembly A.

6. A calculation method that predicts a difference $\Delta G$ between free energy of first molecules, and free energy of second molecules, based on the formula: $\Delta G=(-\Delta G_1)+\Delta G_2$, by calculating using a computer, with respect to change represented by reaction formula (1-1):

$$A+B_1\rightarrow AB_1 \quad (1\text{-}1)$$

wherein A represents an atomic assembly consisting of structure a or comprising structure a, $B_1$ represents a fragment consisting of one or more atoms, and $AB_1$ represents an atomic assembly constituting the first molecules and consisting of atomic assembly A and fragment $B_1$ connected to structure a of the atomic assembly A, a difference $\Delta G_1$ between a sum of free energy of atomic assembly A before the change and free energy of fragment $B_1$, and free energy of atomic assembly $AB_1$ after the change, and with respect to change represented by reaction formula (1-2):

$$A+B_2\rightarrow AB_2 \quad (1\text{-}2)$$

wherein A is defined as above, $B_2$ represents a fragment consisting of one or more atoms and differing from fragment $B_1$, and $AB_2$ represents an atomic assembly constituting the second molecules and consisting of atomic assembly A and fragment $B_2$ connected to structure a of the atomic assembly A, a difference $\Delta G_2$ between a sum of free energy of atomic assembly A before the change and free energy of fragment $B_2$, and free energy of atomic assembly $AB_2$ after the change, wherein the first molecules comprise a ligand(s), a protein(s) to which the ligand(s) may be bound, and a solvent molecule(s), wherein the second molecules comprise a ligand(s), a protein(s) to which the ligand(s) may be bound, and a solvent molecule(s), and wherein a control unit of the computer performs:

a first atomic assembly model creation step of creating a first atomic assembly model modeling atomic assembly A before the change;

a first coordinates acquisition step of causing molecular dynamics simulation program to read as data for the first atomic assembly model created by the first atomic assembly model creation unit, coordinates of each of atoms constituting atomic assembly A, the kind thereof, a mass thereof, a partial charge thereof, and interatomic bond information, and as data for a simulation condition, simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a condition for a 1-4 interaction, and an output condition including the number of snapshots, performing molecular dynamics simulation with respect to the first atomic assembly model created by the first atomic assembly model creation unit, and acquiring coordinates of atomic assembly A in each of first to i th states $F_1$ to $F_i$, wherein i is an integer of two or more, by a snapshot output as a result of molecular dynamics simulation with respect to the first atomic assembly model created by the first atomic assembly model creation step, wherein the snapshot in each of the states $F_1$ to $F_i$ incudes coordinates of all the atoms constituting atomic assembly A in each of states $F_1$ to $F_i$;

a second coordinates acquisition step of acquiring coordinates of atomic assembly $AB_1$ or $AB_2$ generated by connection of fragment $B_1$ or $B_2$ to atomic assembly A in each of states $F_1$ to $F_i$ based on the coordinates of atomic assembly A acquired by the first coordinates acquisition step, wherein the coordinates of atomic assembly $AB_1$ or $AB_2$ acquired by the second coordinates acquisition step contain coordinates of all the atoms constituting atomic assembly $AB_1$ or $AB_2$;

a first interaction energy $\phi$ frequency distribution creation step of calculating interaction energy $\phi$ between structure a and fragment $B_1$ or $B_2$ connected to the structure a based on the coordinates of atomic assembly $AB_1$ or $AB_2$ acquired by the second coordinates acquisition step, and creating a frequency distribution indicating a frequency in each class of interaction energy $\phi$;

a first interaction energy $\phi$ appearance probability calculation step of calculating an appearance probability $P_0(\phi)$ in each class of interaction energy $\phi$ based on the frequency distribution created by the first interaction energy $\phi$ frequency distribution creation step;

a first interaction energy $\varepsilon$ frequency distribution creation step of calculating interaction energy $\varepsilon$ between a part or the whole of an atomic assembly generated by removing structure $aB_1$ or $aB_2$ consisting of structure a and fragment $B_1$ or $B_2$ connected to the structure a from atomic assembly $AB_1$ or $AB_2$, and fragment $B_1$ or $B_2$ based on the coordinates of atomic assembly $AB_1$ or $AB_2$ acquired by the second coordinates acquisition step, and creating a frequency distribution indicating a frequency in each class of interaction energy $\varepsilon$ in each class of interaction energy $\phi$ in the frequency distribution created by the first interaction energy $\phi$ frequency distribution creation step;

a first interaction energy $\varepsilon$ appearance probability calculation step of calculating an appearance probability $P_0'(\varepsilon;\phi)$ in each class of interaction energy $\varepsilon$ in each class of interaction energy $\phi$ based on the frequency distribution created by the first interaction energy $\varepsilon$ frequency distribution creation step;

a second atomic assembly model creation step of creating a second atomic assembly model modeling atomic assembly $AB_1$ or $AB_2$ after the change;

a third coordinates acquisition step of causing molecular dynamics simulation program to read as data for the second atomic assembly model created by the second atomic assembly model creation unit, coordinates of each of atoms constituting atomic assembly $AB_1$ or $AB_2$, the kind thereof, a mass thereof, a partial charge thereof, and interatomic bond information, and as data for a simulation condition, simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a condition for a 1-4 interaction, and an output condition including the number of snapshots, performs molecular dynamics simulation with respect to the second atomic assembly model created by the second atomic assembly model creation unit, and acquiring coordinates of atomic assembly $AB_1$ or $AB_2$ in each of first to j th states $G_1$ to $G_j$ (wherein j is an integer of two or more) by a snapshot output as a result of molecular dynamics simulation with respect to the second atomic assembly model created by the second atomic assembly model creation step, wherein the snapshot in each of states $G_1$ to $G_j$ includes coordinates of all the atoms constituting atomic assembly $AB_1$ or $AB_2$ in each of states $G_1$ to $G_j$;

a second interaction energy $\phi$ frequency distribution creation step for calculating interaction energy $\phi$ between structure a and fragment $B_1$ or $B_2$ connected to the structure a based on the coordinates of atomic assembly $AB_1$ or $AB_2$ acquired by the third coordinates acquisition step, and creating a frequency distribution indicating a frequency in each class of interaction energy $\phi$;

a second interaction energy $\phi$ appearance probability calculation step of calculating an appearance probability $P(\phi)$ in each class of interaction energy $\phi$ based on the frequency distribution created by the second interaction energy $\phi$ frequency distribution creation step;

a second interaction energy $\varepsilon$ frequency distribution creation step of calculating interaction energy $\varepsilon$ between a part or the whole of an atomic assembly generated by removing structure $aB_1$ or $aB_2$ consisting of structure a and fragment $B_1$ or $B_2$ connected to the structure a from atomic assembly $AB_1$ or $AB_2$, and fragment $B_1$ or $B_2$ based on the coordinates of atomic assembly $AB_1$ or $AB_2$ acquired by the third coordinates acquisition step, and creating a frequency distribution indicating a frequency in each class of interaction energy $\varepsilon$;

a second interaction energy $\varepsilon$ appearance probability calculation step of calculating an appearance probability $P'(\varepsilon)$ in each class of interaction energy $\varepsilon$ based on the frequency distribution created by the second interaction energy $\varepsilon$ frequency distribution creation step;

a $\int \Delta v(\phi)P(\phi)d\phi$ calculation step for calculating a free energy change amount $\int \Delta v(\phi)P(\phi)d\phi$, wherein $\Delta v(\phi)$ represents a free energy change amount caused by interaction energy $\varepsilon$ in each class of interaction energy $\phi$, caused by interaction energy $\varepsilon$ based on $P(\phi)$ calculated by the second interaction energy $\phi$ appearance probability calculation step, $P_0'(\varepsilon;\phi)$ calculated by the first interaction energy $\varepsilon$ appearance probability calculation step, and $P'(\varepsilon)$ calculated by the second interaction energy $\varepsilon$ appearance probability calculation step; and a $\Delta G_1$ or $\Delta G_2$ calculation step of calculating $\Delta G_1$ or $\Delta G_2$ based on $P_0(\phi)$ calculated by the first interaction energy $\phi$ appearance probability calculation step, $P(\phi)$ calculated by the second interaction energy $\phi$ appearance probability calculation step, $\int \Delta v(\phi)P(\phi)d\phi$ calculated by the $\int \Delta v(\phi)P(\phi)d\phi$ calculation step, and numerical formula (1):

$$\Delta G = \int \phi P(\phi)d\phi + RT \int P(\phi)\log\left(\frac{P(\phi)}{P_0(\phi)}\right)d\phi + \int \Delta v(\phi)P(\phi)d\phi \quad (1)$$

wherein R represents a gas constant, and T represents an absolute temperature at which the change represented by reaction formula (1) occurs.

7. The calculation method according to claim 6, wherein in the second coordinates acquisition step, the control unit of the computer creates a third atomic assembly model modeling atomic assembly C consisting of structure a and fragment $B_1$ or $B_2$ connected to the structure a or comprising structure a and fragment $B_1$ or $B_2$ connected to the structure a, acquires coordinates of atomic assembly C in each of first to k th states $H_1$ to $H_k$ (wherein k is an integer of two or more) by molecular dynamics simulation with respect to the created third atomic assembly model, and selects a selected atomic group consisting of one or more atoms selected from atoms constituting structure a, rotates and/or translates coordinates of a selected atomic group of atomic assembly C in one or more states selected from states $H_1$ to $H_k$ with respect to coordinates of a selected atomic group of atomic assembly A in each of states $F_1$ to $F_i$, thereby creates coordinates of atomic assembly C having the minimum sum of squares of distances between corresponding atoms between the selected atomic group of atomic assembly A and the selected atomic group of atomic assembly C, superimposes atomic assembly C in one or more states selected from states $H_1$ to $H_k$ on atomic assembly A based on the created coordinates of atomic assembly C, and acquires one or more coordinates of atomic assembly $AB_1$ or $AB_2$ generated by connection of fragment $B_1$ or $B_2$ to atomic assembly A based on coordinates of atomic assembly A and one or more coordinates of fragment $B_1$ or $B_2$ of atomic assembly C superimposed on atomic assembly A.

8. The calculation method according to claim 6, wherein in the $\int \Delta v(\phi) P(\phi) d\phi$ calculation step, the control unit of the computer calculates a free energy change amount $\int \Delta v(\phi) P(\phi) d\phi$ caused by interaction energy $\varepsilon$ based on $P(\phi)$ calculated by the second interaction energy $\phi$ appearance probability calculation step, $P_0'(\varepsilon;\phi)$ calculated by the first interaction energy $\varepsilon$ appearance probability calculation step, and $P'(\varepsilon)$ calculated by the second interaction energy $\varepsilon$ appearance probability calculation step by the energy representation method.

9. The calculation method according to claim 8, wherein fragment $B_1$ or $B_2$ is constituted of an atom(s) containing a point charge(s) as a virtual atom(s), and the control unit of the computer adds the point charge(s) of fragment $B_1$ or $B_2$ to a charge parameter(s) of an atom(s) constituting structure a of atomic assembly A in the second coordinates acquisition step.

10. The calculation method according to claim 6, wherein fragment $B_1$ or $B_2$ is constituted of an atom(s) containing a point charge(s) as a virtual atom(s), and the control unit of the computer adds the point charge(s) of fragment $B_1$ or $B_2$ to a charge parameter(s) of an atom(s) constituting structure a of atomic assembly A in the second coordinates acquisition step.

11. A non-transitory computer-readable recording medium with a program recorded thereon, wherein the program predicts a difference $\Delta G$ between free energy of first molecules, and free energy of second molecules, based on the formula: $\Delta G=(-\Delta G_1)+\Delta G_2$, by calculating, with respect to change represented by reaction formula (1-1):

$$A+B_1 \rightarrow AB_1 \qquad (1\text{-}1)$$

wherein A represents an atomic assembly consisting of structure a or comprising structure a, $B_1$ represents a fragment consisting of one or more atoms, and $AB_1$ represents an atomic assembly constituting the first molecules and consisting of atomic assembly A and fragment $B_1$ connected to structure a of the atomic assembly A, a difference $\Delta G_1$ between a sum of free energy of atomic assembly A before the change and free energy of fragment $B_1$, and free energy of atomic assembly $AB_1$ after the change, and with respect to change represented by reaction formula (1-2):

$$A+B_2 \rightarrow AB_2 \qquad (1\text{-}2)$$

wherein A is defined as above, $B_2$ represents a fragment consisting of one or more atoms and differing from fragment $B_1$, and $AB_2$ represents an atomic assembly constituting the second molecules and consisting of atomic assembly A and fragment $B_2$ connected to structure a of the atomic assembly A, a difference $\Delta G_2$ between a sum of free energy of atomic assembly A before the change and free energy of fragment $B_2$, and free energy of atomic assembly $AB_2$ after the change, wherein the first molecules comprise a ligand(s), a protein(s) to which the ligand(s) may be bound, and a solvent molecule(s), wherein the second molecules comprise a ligand(s), a protein(s) to which the ligand(s) may be bound, and a solvent molecule(s), and wherein the program causes a control unit of a computer to function as:

a first atomic assembly model creation unit that creates a first atomic assembly model modeling atomic assembly A before the change;

a first coordinates acquisition unit that causes molecular dynamics simulation program to read as data for the first atomic assembly model created by the first atomic assembly model creation unit, coordinates of each of atoms constituting atomic assembly A, the kind thereof, a mass thereof, a partial charge thereof, and interatomic bond information, and as data for a simulation condition, simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a condition for a 1-4 interaction, and an output condition including the number of snapshots, performs molecular dynamics simulation with respect to the first atomic assembly model created by the first atomic assembly model creation unit, and acquires coordinates of atomic assembly A in each of first to i th states $F_1$ to $F_i$ (wherein i is an integer of two or more) by a snapshot output as a result of molecular dynamics simulation with respect to the first atomic assembly model created by the first atomic assembly model creation unit, wherein the snapshot in each of states $F_1$ to $F_i$ includes coordinates of all the atoms constituting atomic assembly A in each of states $F_1$ to $F_i$;

a second coordinates acquisition unit that acquires coordinates of atomic assembly $AB_1$ or $AB_2$ generated by connection of fragment $B_1$ or $B_2$ to atomic assembly A in each of states $F_1$ to $F_i$ based on the coordinates of atomic assembly A acquired by the first coordinates acquisition unit, wherein the coordinates of atomic assembly $AB_1$ or $AB_2$ acquired by the second coordinates acquisition unit contain coordinates of all the atoms constituting atomic assembly $AB_1$ or $AB_2$;

a first interaction energy $\phi$ frequency distribution creation unit that calculates interaction energy $\phi$ between structure a and fragment $B_1$ or $B_2$ connected to the structure a based on the coordinates of atomic assembly $AB_1$ or $AB_2$ acquired by the second coordinates acquisition unit, and creating a frequency distribution indicating a frequency in each class of interaction energy $\phi$;

a first interaction energy $\phi$ appearance probability calculation unit that calculates an appearance probability $P_0(\phi)$ in each class of interaction energy $\phi$ based on the frequency distribution created by the first interaction energy $\phi$ frequency distribution creation unit;

a first interaction energy $\epsilon$ frequency distribution creation unit that calculates interaction energy $\epsilon$ between a part or the whole of an atomic assembly generated by removing structure $aB_1$ or $aB_2$ consisting of structure a and fragment $B_1$ or $B_2$ connected to the structure a from atomic assembly $AB_1$ or $AB_2$, and fragment $B_1$ or $B_2$ based on the coordinates of atomic assembly $AB_1$ or $AB_2$ acquired by the second coordinates acquisition unit, and creating a frequency distribution indicating a frequency in each class of interaction energy $\epsilon$ in each class of interaction energy $\phi$ in the frequency distribution created by the first interaction energy $\phi$ frequency distribution creation unit;

a first interaction energy $\epsilon$ appearance probability calculation unit that calculates an appearance probability $P_0'(\epsilon;\phi)$ in each class of interaction energy $\epsilon$ in each class of interaction energy $\phi$ based on the frequency distribution created by the first interaction energy $\epsilon$ frequency distribution creation unit;

a second atomic assembly model creation unit that creates a second atomic assembly model modeling atomic assembly $AB_1$ or $AB_2$ after the change;

a third coordinates acquisition unit that causes molecular dynamics simulation program to read as data for the second atomic assembly model created by the second atomic assembly model creation unit, coordinates of each of atoms constituting atomic assembly $AB_1$ or $AB_2$, the kind thereof, a mass thereof, a partial charge thereof, and interatomic bond information, and as data for a simulation condition, simulation time, a temperature condition, a pressure condition, the kind of a potential parameter(s) and a value(s) thereof, the kind of an ensemble generated, a boundary condition, a numerical solution of an equation of motion, a time step of numerical integration, a switching function and a cut-off radius for van der Waals potential and Coulomb potential calculation, a condition for a long-distance interaction in Coulomb potential calculation, a condition for a 1-4 interaction, and an output condition including the number of snapshots, performs molecular dynamics simulation with respect to the second atomic assembly model created by the second atomic assembly model creation unit, and acquires coordinates of atomic assembly $AB_1$ or $AB_2$ in each of first to j th states $G_1$ to $G_j$ (wherein j is an integer of two or more) by a snapshot output as a result of molecular dynamics simulation with respect to the second atomic assembly model created by the second atomic assembly model creation unit, wherein the snapshot in each of states $G_1$ to $G_j$ includes coordinates of all the atoms constituting atomic assembly $AB_1$ or $AB_2$ in each of states $G_1$ to $G_j$;

a second interaction energy $\phi$ frequency distribution creation unit that calculates interaction energy $\phi$ between structure a and fragment $B_1$ or $B_2$ connected to the structure a based on the coordinates of atomic assembly $AB_1$ or $AB_2$ acquired by the third coordinates acquisition unit, and creating a frequency distribution indicating a frequency in each class of interaction energy $\phi$;

a second interaction energy $\phi$ appearance probability calculation unit that calculates an appearance probability $P(\phi)$ in each class of interaction energy $\phi$ based on the frequency distribution created by the second interaction energy $\phi$ frequency distribution creation unit;

a second interaction energy $\epsilon$ frequency distribution creation unit that calculates interaction energy $\epsilon$ between a part or the whole of an atomic assembly generated by removing structure $aB_1$ or $aB_2$ consisting of structure a and fragment $B_1$ or $B_2$ connected to the structure a from atomic assembly $AB_1$ or $AB_2$, and fragment $B_1$ or $B_2$ based on the coordinates of atomic assembly $AB_1$ or $AB_2$ acquired by the third coordinates acquisition unit, and creating a frequency distribution indicating a frequency in each class of interaction energy $\epsilon$;

a second interaction energy $\epsilon$ appearance probability calculation unit that calculates an appearance probability $P'(\epsilon)$ in each class of interaction energy $\epsilon$ based on the frequency distribution created by the second interaction energy $\epsilon$ frequency distribution creation unit;

a $\int \Delta v(\phi) P(\phi) d\phi$ calculation unit that calculates a free energy change amount $\int \Delta v(\phi) P(\phi) d\phi$, wherein $\Delta v(\phi)$ represents a free energy change amount caused by interaction energy $\epsilon$ in each class of interaction energy $\phi$, caused by interaction energy $\epsilon$ based on $P(\phi)$ calculated by the second interaction energy $\phi$ appearance probability calculation unit, $P_0'(\epsilon;\phi)$ calculated by the first interaction energy $\epsilon$ appearance probability calculation unit, and $P'(\epsilon)$ calculated by the second interaction energy $\epsilon$ appearance probability calculation unit; and a $\Delta G_1$ or $\Delta G_2$ calculation unit that calculates $\Delta G_1$ or $\Delta G_2$ based on $P_0(\phi)$ calculated by the first interaction energy $\phi$ appearance probability calculation unit, $P(\phi)$ calculated by the second interaction energy $\phi$ appearance probability calculation unit, $\int \Delta v(\phi) P(\phi) d\phi$ calculated by the $\int \Delta v(\phi) P(\phi) d\phi$ calculation unit, and numerical formula (1):

$$\Delta G = \int \phi P(\phi) d\phi + RT \int P(\phi) \log\left(\frac{P(\phi)}{P_0(\phi)}\right) d\phi + \int \Delta v(\phi) P(\phi) d\phi \quad (1)$$

wherein R represents a gas constant, and T represents an absolute temperature at which the change represented by reaction formula (1) occurs.

12. The computer-readable recording medium according to claim 11, wherein the second coordinates acquisition unit creates a third atomic assembly model modeling atomic assembly C consisting of structure a and fragment $B_1$ or $B_2$ connected to the structure a or comprising structure a and fragment $B_1$ or $B_2$ connected to the structure a, acquires coordinates of atomic assembly C in each of first to k th states $H_1$ to $H_k$ (wherein k is an integer of two or more) by molecular dynamics simulation with respect to the created third atomic assembly model, and selects a selected atomic group consisting of one or more atoms selected from atoms constituting structure a, rotates and/or translates coordinates of a selected atomic group of atomic assembly C in one or more states selected from states $H_1$ to $H_k$ with respect to coordinates of a selected atomic group of atomic assembly A in each of states $F_1$ to $F_i$, thereby creates coordinates of atomic assembly C having the minimum sum of squares of distances between corresponding atoms between the selected atomic group of atomic assembly A and the selected atomic group of atomic assembly C, superimposes atomic assembly C in one or more states selected from states $H_1$ to $H_k$ on atomic assembly A based on the created coordinates of atomic assembly C, and acquires one or more coordinates of atomic assembly $AB_1$ or $AB_2$ generated by connection of fragment $B_1$ or $B_2$ to atomic assembly A based on coordinates of atomic assembly A and one or more coordinates of fragment $B_1$ or $B_2$ of atomic assembly C superimposed on atomic assembly A.

13. The computer-readable recording medium according to claim 11, wherein the $\int \Delta v(\phi) P(\phi) d\phi$ calculation unit calculates a free energy change amount $\int \Delta v(\phi) P(\phi) d\phi$ caused by interaction energy $\varepsilon$ based on $P(\phi)$ calculated by the second interaction energy $\phi$ appearance probability calculation unit, $P_0'(\varepsilon;\phi)$ calculated by the first interaction energy $\varepsilon$ appearance probability calculation unit, and $P'(\varepsilon)$ calculated by the second interaction energy $\varepsilon$ appearance probability calculation unit by the energy representation method.

14. The computer-readable recording medium according to claim 13, wherein fragment $B_1$ or $B_2$ is constituted of an atom(s) containing a point charge(s) as a virtual atom(s), and the second coordinates acquisition unit adds the point charge(s) of fragment $B_1$ or $B_2$ to a charge parameter(s) of an atom(s) constituting structure a of atomic assembly A.

15. The computer-readable recording medium according to claim 11, wherein fragment $B_1$ or $B_2$ is constituted of an atom(s) containing a point charge(s) as a virtual atom(s), and the second coordinates acquisition unit adds the point charge(s) of fragment $B_1$ or $B_2$ to a charge parameter(s) of an atom(s) constituting structure a of atomic assembly A.

\* \* \* \* \*